United States Patent
Field et al.

(10) Patent No.: US 11,104,913 B2
(45) Date of Patent: Aug. 31, 2021

(54) PHOTOSYNTHETIC ORGANISMS THROUGH THE MODULATION OF GUANOSINE TETRAPHOSPHATE HOMEOSTATIS

(71) Applicants: CENTRE NATIONAL DE LA RECHERCHE SCIENTIFIQUE (CNRS), Paris (FR); UNIVERSITÉ D'AIX MARSEILLE, Marseilles (FR)

(72) Inventors: Benjamin Field, Marseilles (FR); Matteo Sugliani, Marseilles (FR); Christophe Robaglia, Marseilles (FR); Hela Abdelkefi, Ariana (TN)

(73) Assignees: CENTRE NATIONAL DE LA RECHERCHE SCIENTIFIQUE (CNRS), Paris (FR); UNIVERSITÉ D'AIX MARSEILLE, Marseilles (FR)

( * ) Notice: Subject to any disclaimer, the term of this patent is extended or adjusted under 35 U.S.C. 154(b) by 22 days.

(21) Appl. No.: 16/076,303

(22) PCT Filed: Feb. 7, 2017

(86) PCT No.: PCT/EP2017/052600
§ 371 (c)(1),
(2) Date: Aug. 7, 2018

(87) PCT Pub. No.: WO2017/137374
PCT Pub. Date: Aug. 17, 2017

(65) Prior Publication Data
US 2019/0169630 A1 Jun. 6, 2019

Related U.S. Application Data

(60) Provisional application No. 62/292,580, filed on Feb. 8, 2016.

(51) Int. Cl.
*C12N 15/00* (2006.01)
*C12N 15/82* (2006.01)

(52) U.S. Cl.
CPC ......... *C12N 15/8266* (2013.01); *C12N 15/00* (2013.01); *C12N 15/8261* (2013.01); *C12N 15/8269* (2013.01); *Y02A 40/146* (2018.01)

(58) Field of Classification Search
None
See application file for complete search history.

(56) References Cited

U.S. PATENT DOCUMENTS

2013/0206155 A1* 8/2013 Davenport .......... C07K 14/415
131/352

FOREIGN PATENT DOCUMENTS

WO    WO-01/05952 A2    1/2001
WO    WO-2008/021543 A2    2/2008

OTHER PUBLICATIONS

Japan a Decision of Rejection dated Feb. 12, 2020.
Uchida, Hiroshi et al; "Resent technical trend of the alicyclic epoxy resins" Network polymers, Japan, 2010, vol. 31, No. 4 pp. 177-190.
Maekawa et al., "Impact of the plastidial stringent response in plant growth and stress responses", Nature Plants, vol. 1, No. 15167, Nov. 9, 2015, pp. 1-7.
Sato et al., "Overexpression of RelA/SpoT homologs, PpRSH2a and PpRSH2b, induces the growth suppression of the moss Physcomitrella patens", Bioscience, Biotechnology, and Biochemistry, vol. 79, No. 1, 2016, pp. 36-44.
Mizusawa et al., "Expression profiling of four RelA/SpoT-like proteins, homologues of bacterial stringent factors, in *Arabidopsis thaliana*", Planta (Berlin), vol. 228, No. 4, Sep. 2008, pp. 553-562.
Tozawa et al., "Signalling by the global regulatory molecule ppGpp in bacteria and chloroplasts of land plants", Plant Biology (Stuttgart), vol. 13, No. 5, Sep. 2011, pp. 699-709.
Masuda et al., "The Bacterial Stringent Response, Conserved in Chloroplasts, Controls Plant Fertilization", Plant and Cell Physiology, vol. 49, No. 2, Feb. 2008, pp. 135-141.
International Search Report issued in corresponding International Patent Application No. PCT/EP2017/052600, dated May 10, 2017.
Reyes-Prieto et al., "The Origin and Establishment of the Plastid in Algae and Plants", The Annual Review of Genetics, vol. 41, 2007, pp. 147-168.
Green, "Chloroplast genomes of photosynthetic eukaryotes", The Plant Journal, vol. 66, 2011, pp. 34-44.
Jarvis et al., "Biogenesis and homeostasis of chloroplasts and other plastids", Nature Reviews Molecular Cell Biology, vol. 14, Dec. 2013, pp. 787-802.
Puthiyaveetil et al., "The ancestral symbiont sensor kinase CSK links photosynthesis with gene expression in chloroplasts", PNAS, vol. 105, No. 29, Jul. 22, 2008, pp. 10061-10066.
Masuda, "The Stringent Response in Phototrophs", Advances in Photosynthesis—Fundamental Aspects, 2012, ISBN: 978-953-307-928-8, Available from: http://www.intechopen.com/books/advances-in-photosynthesis-fundamental-aspects/the-stringent-responsein-phototrophs.
Dalebroux et al., "ppGpp: magic beyond RNA polymerase", Nature Reviews Microbiology, vol. 10, Mar. 2012, pp. 203-212.
Biezen et al., "*Arabidopsis* RelA/SpoT homologs implicate (p)ppGpp in plant signaling", PNAS, vol. 97, No. 7, Mar. 28, 2000, pp. 3747-3752.
Arkinson et al., "The RelA/SpoT Homolog (RSH) Superfamily: Distribution and Functional Evolution of ppGpp Synthetases and Hydrolases across the Tree of Life", PLoS One, vol. 6, Issue 8, e23479, Aug. 2011.

(Continued)

*Primary Examiner* — Phuong T Bui
(74) *Attorney, Agent, or Firm* — Foley & Lardner LLP; Sunit Talapatra

(57) ABSTRACT

The present invention concerns methods and approaches for modifying guanosine tetraphosphate (ppGpp) homeostasis in photosynthetic eukaryotes, in particular plants or algae, in order to modulate senescence for the remobilisation of nitrogen and other nutrients from the chloroplast, and modified photosynthetic eukaryotes thus produced.

2 Claims, 17 Drawing Sheets
Specification includes a Sequence Listing.

(56) References Cited

OTHER PUBLICATIONS

Tozawa et al., "Signaling by the global regulatory molecule ppGpp in bacteria and chloroplasts of land plants", Plant Biology, vol. 13, 2011, pp. 699-709.
Takahashi et al., "Identification of the bacterial alarmone guanosine 5'-diphosphate 3'-diphosphate (ppGpp) in plants", PNAS, vol. 101, No. 12, Mar. 23, 2004, pp. 4320-4324.
Ihara et al., "A highly sensitive quantification method for the accumulation of alarmone ppGpp Arabidopsis thaliana using UPLC-ESI-qMS/MS", The Botanical Society of Japan and Springer, 2015.
Sato et al., "Bacterial Alarmone, Guanosine 5'-Diphosphate 3'-Diphosphate (ppGpp), Predominantly Binds the β' Subunit of Plastid-Encoded Plastid RNA Polymerase in Chloroplasts", ChemBioChem, vol. 10, 2009, pp. 1227-1233.
Nomura et al., "ppGpp inhibits pepride elongation cycle of chloroplast translation system in vitro", Plant Mol Biol, vol. 78, 2012, pp. 185-196.
Nomura et al., "Diversity in Guanosine 3', 5'-Bisdiphosphate (ppGpp) Sensitivity among Guanylate Kinases of Bacteria and Plants," vol. 289, No. 22, May 30, 2014, pp. 15631-15641.
Tozawa et al., "Enzyme Catalysis and Regulation: Calcium-activated (p)ppGpp Synthetase in Chloroplasts of Land Plants", The Journal of Biological Chemistry, vol. 282, No. 49, Dec. 7, 2007, pp. 35536-35545.
Mizusawa et al., "Expression profiling of four RelA/SpoT-like proteins, homologues of bacterial stringent factors, in *Arabidopsis thaliana*" Planta, vol. 228, No. 4, Sep. 2008, pp. 553-562.
Masuda et al. "The Bacterial Stringent Response, Conserved in Chloroplasts, Controls Plant Fertilization", Plant Cell Physiol. vol. 49, No. 2, 2008, pp. 135-141.
Chen et al., "AtObgC-AtRSH1 interaction may play a vital role in stress response signal transduction in *Arabidopsis*", Plant Physiology and Biochemistry, vol. 74, 2014, pp. 176-184.
Earley et al., "Gateway-compatible vectors for plant functional genomics and proteomics", The Plant Journal, vol. 45, 2006, pp. 616-629.
Field et al., "Metabolic Diversification—Independent Assembly of Operon-Like Gene Clusters in Different Plants", Science, vol. 320, No. 543, 2008.
Schreiber et al., "Overexpression of the relA Gene in *Escherichia coli*", The Journal of Biological Chemistry, vol. 266, No. 6, Feb. 25, 1991, pp. 3760-3767.
Hogg et al, "Conformational Antagonism between Opposing Active Sites in a Bifunctional RelA/SpoT Homolog Modulates (p)ppGpp Metabolism during the Stringent Response", Cell, vol. 117, Apr. 2, 2004, pp. 57-68.
Craft et al., "New pOp/LhG4 vectors for stringent glucocorticoid-dependent transgene expression in *Arabidopsis*", The Plant Journal, vol. 41, 2005, p. 899-918.
Liu et al., "High-efficiency thermal asymmetric interlaced PCR for amplification of unknown flanking sequences", BioTechniques, vol. 43, No. 5, 2007, pp. 649-656.
Sun et al., "A metazoan ortholog of SpoT hydrolyzes ppGpp and functions in starvation responses", Nature Structual & Molecular Biology, vol. 17, No. 10, Oct. 2010, pp. 1188-1195.
Schwab et al., "Highly Specific Gene Silencing by Artificial MicroRNAs in *Arabidopsis*", The Plant Cell, vol. 18, No. 5, May 2006, pp. 1121-1133.
Guzman et al., "Tight Regulation, Modulation, and High-Level Expression by Vectors Containing the Arabinose $P_{BAD}$ Promoter", vol. 177, No. 14, Jul. 1995, pp. 4121-4130.
Zhao et al., "Comprehensive Algorithm for Quantitative Real-Time Polymerase Chain Reaction", Journal of Computational Biology, vol. 12, No. 8, 2005, pp. 1047-1064.
Jarvis, "Chloroplast Research in *Arabidopsis*", Methods and Protocols, vol. 1, ISBN 978-1-61779-233-5, DOI 10.1007/978-1-61779-234-2, Springer New York Dordrecht Heidelberg London, 2011.
Croce et al., "Chromophore Organization in the Higher-Plant Photosystem II Antenna Protein CP26", Biochemistry, vol. 41, 2002, pp. 7334-7343.

Yoo et al., "*Arabidopsis* mesophyll protoplasts: a versatile cell system for transient gene expression analysis", Nature Protocols, vol. 2, No. 7, 2007, pp. 1565-1572.
Pyke et al., "Rapid Image Analysis Screening Procedure for Identifying Chloroplast Number Mutants in Mesophyll Cells of *Arabidopsis thaliana* (L.) Heynh", Plant Physiol, vol. 96, 1991, pp. 1193-1195.
Wahl et al., "Antagonistic regulation of dgkA and plsB genes of phospholipid synthesis by multiple stress responses in *Escherichia coli*", Molecular Microbiology, vol. 80, No. 5, 2011, pp. 1260-1275.
Battesti et al., "Acyl carrier protein/SpoT interaction, the switch linking SpoT-dependent stress response to fatty acid metabolism", Molecular Microbiology, 2006.
My et al., "Transcription of the *Escherichia coli* Fatty Acid Synthesis Operon fabHDG Is Directly Activated by FadR and Inhibited by ppGpp", Journal of Bacteriology, vol. 195, No. 16, Aug. 2013.
Maekawa et al., "Impact of the plastidial stringent response in plant growth and stress responses", Nature Plants, published Nov. 9, 2015, article No. 15167, http://dx.doi.org/10.1038/nplants.2015.167.
Belgio et al., "Higher Plant Photosystem II Light-Harvesting Antenna, Not the Reaction Center, Determines the Excited-State Lifetime—Both the Maximum and the Nonphotochemically Quenched" Biophysical Journal, vol. 102, Jun. 2012, pp. 2761-2771.
Robertson et al., "arc6, an extreme chloroplast division mutant of *Arabidopsis* also alters proplastid proliferation and morphology in shoot and root apices", Journal of Cell Science, vol. 108, pp. 2937-2944, 1995.
Diray-Arce et al., "The *Arabidopsis* At1g30680 gene encodes a homologue to the phage T7 gp4 protein that has both DNA primase and DNA helicase activities", BMC Plant Biology, vol. 13, No. 36, 2013.
Kriel et al., "Direct Regulation of GTP Homeostasis by (p)ppGpp: A Critical Component of Viability and Stress Resistance", Molecular Cell, vol. 48, Oct. 26, 2012, pp. 231-241.
Krasny et al., "An alternative strategy for bacterial ribosome synthesis: Bacillus subtilis rRNA transcription regulation", The EMBO Journal, vol. 23, 2004, pp. 4473-4483.
Borner et al.,"Chloroplast RNA polymerases: Role in chloroplast biogenesis", Biochim. Biophys. Acta, 2015, http://dx.doi.org/10.1016/j.bbabio.2015.02.004.
Sidaway-Lee et al., "Direct measurement of transcription rates reveals multiple mechanisms for configuration of the *Arabidopsis* ambient temperature response", Genome Biology, 2014, vol. 15:R45, http://genomebiology.com/2014/15/3/R45.
Cahoon et al., "Analysis of developing maize plastids reveals two mRNA stability classes correlating with RNA polymerase type", EMBO reports, vol. 5, No. 8, 2004, pp. 801-806.
Rapp et al., "Quantitative Analysis of Transcription and RNA Levels of 15 Barley Chloroplast Genes", The Journal of Biological Chemistry, vol. 267, No. 30, Oct. 25, 1992, pp. 21404-21411.
Gerhardt et al., "Subcellular Metabolite Levels in Spinach Leaves Regulation of Sucrose Synthesis During Diurnal Alterations in Photosynthetic Partitioning", Plant Physiol,, vol. 83, 1987, pp. 399-407.
Suzuki et al., "Unique Architecture of the Plastid Ribosomal RNA Operon Promoter Recognized by the Multisubunit RNA Polymerase in Tobacco and Other Higher Plants", The Plant Cell, vol. 15, Jan. 2003, pp. 195-205.
Swiatecka-Hagenbruch et al., "High diversity of plastidial promoters in *Arabidopsis thaliana*", Mol Genet Genomics, vol. 277, 2007, pp. 725-734.
Schmidt et al., "SUnSET, a nonradioactive method to monitor protein synthesis", Nature Methods, vol. 6, No. 4, Apr. 2009, pp. 275-277.
Engelmann et al., "The effect of outer antenna complexes on the photochemical trapping rate in barley thylakoid Photosystem II", Biochimica et Biophysica Acta, vol. 1706, 2005, pp. 276-286.
Ito et al., Enzymatic and Molecular Characterization of *Arabidopsis* ppGpp Pyrophosphohydrolase, AtNUDX26, Biosci. Biotechnol. Biochem., vol. 76, No. 12, 2012, pp. 2236-2241.
Schmid et al., "A gene expression map of *Arabidopsis thaliana* development", Nature Genetics, vol. 37, No. 5, May 2005, pp. 501-506.

(56) References Cited

OTHER PUBLICATIONS

Breeze et al., "High-Resolution Temporal Profiling of Transcripts during *Arabidopsis* Leaf Senescence Reveals a Distinct Chronology of Processes and Regulation", The Plant Cell, vol. 23: 873-894, Mar. 2011.
Lim et al., "Leaf Senescence", Annu. Rev. Plant Biol. 2007. 58:115-36.
Buchanan-Wollaston et al., "Comparative transcriptome analysis reveals significant differences in gene expression and signalling pathways between developmental and dark/starvation-induced senescence in *Arabidopsis*", The Plant Journal (2005) 42, 567-585.
Liere et al., "The transcription machineries of plant mitochondria and chloroplasts: Composition, function, and regulation", dx.doi.org/10.1016/j.jplph.2011.01.005.
Rochaix, "Redox regulation of thylakoid protein kinases and photosynthetic gene expression", Forum Review Article, 2012, pp. 1-68.
Biswal et al., "Plastid Development in Leaves during Growth and Senescence", ISSN 1572-0233 ISBN 978-94-007-5723-3 ISBN 978-94-007-5724-0 (eBook) DOI 10.1007/978-94-007-5724-0, 2013.
Tiller et al., "The Translational Apparatus of Plastids and Its Role in Plant Development", Molecular Plant, vol. 7, No. 7, Jul. 2014, pp. 1105-1120.
Kindgren et al., "The plastid redox insensitive 2 mutant of *Arabidopsis* is impaired in PEP activity and high light-dependent plastid redox signalling to the nucleus", The Plant Journal, vol. 70, 2012, pp. 279-291.
Feller et al., "Rubiscolytics: fate of Rubisco after its enzymatic function in a cell is terminated", Journal of Experimental Botany, vol. 59, No. 7, pp. 1615-1624, 2008.
Ishida et al., "Roles of autophagy in chloroplast recycling", Biochimica et Biophysica Acta, vol. 1837, 2014, pp. 512-521.
Potrykus et al., "(p)ppGpp: Still Magical?", Annu. Rev. Microbiol. 2008. 62:35-51.
Bang et al., "Functional characterization of ObgC in ribosome biogenesis during chloroplast development", The Plant Journal, 2012.
David et al., "Nuclear translation visualized by ribosome-bound nascent chain puromycylation", J. Cell Biol., vol. 197, No. 1, pp. 45-57, 2015.
Zimmermann et al., "Genevestigator. *Arabidopsis* Microarray Database and Analysis Toolbox", Plant Physiology, vol. 136, Sep. 2004, pp. 2621-2632.
Kasai et al., "A RelA-SpoT homolog (Cr-RSH) identified in Chlamydomonas reinhardtii generates stringent factor in vivo and localizes to chloroplasts in vitro", Nucleic Acids Research, vol. 30, No. 22, May 20, 2002, pp. 4985-4992.
Lee et al., "In vivo Import Experiments in Protoplasts Reveal the Importance of the Overall Context but Not Specific Amino Acid Residues of the Transit Peptide during Import into Chloroplasts", Molecules and Cells, vol. 14, No. 3, Aug. 26, 2002, pp. 388-397.
Yamburenko et al., "Abscisic acid affects transcription of chloroplast genes via protein phosphatase 2C-dependent activation of nuclear genes: repression by guanosine-3'-5'-bisdiphosphate and activation by sigma factor 5", The Plant Journal, 2015, vol. 82, pp. 1030-1041.

* cited by examiner

SEQUENCE LISTING

```
<160> NUMBER OF SEQ ID NOS: 132

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggggacaagt ttgtacaaaa aagcaggcct tcctctgctt cttcttcttc ac          52

<210> SEQ ID NO 2
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggggacaagt ttgtacaaaa aagcaggctt catgtgttct gtgtattcat gtggca      56

<210> SEQ ID NO 3
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggggaccact ttgtacaaga aagctgggtt taaacactca agaacttgag cattc       55

<210> SEQ ID NO 4
<211> LENGTH: 53
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4
ggggacaagt ttgtacaaaa aagcaggcaa agattaattt cgtccttaa agc              53

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggggacaagt ttgtacaaaa aagcaggctt catggcttct tcatcttctt cctc             54

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggggaccact ttgtacaaga aagctgggtt taagcttccc catccgacc                   49

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggggacaagt ttgtacaaaa aagcaggcga ttggtttatt tctagtttct tc               52

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggggacaagt ttgtacaaaa aagcaggcag aatcatccct ggttgtgtca aa               52

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggggacaagt ttgtacaaaa aagcaggctt catggcttct tcctcttctt cctc             54

<210> SEQ ID NO 10
<211> LENGTH: 49
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 10
ggggaccact tgtacaaga aagctgggtt atagcttccc cagccaacc                49

<210> SEQ ID NO 11
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggggaccact tgtacaaga aagctgggtt agaatgtaag agaatcaaat attaatgacc    60
a                                                                  61

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggggacaagt ttgtacaaaa aagcaggcgc ctcaattttc aaaatcaatc tc           52

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggggacaagt ttgtacaaaa aagcaggctt catgtcgacg gctcggtct               49

<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggggaccact ttgtacaaga aagctgggtt taaatgggtt gagagacgat cc           52

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caccatggct tcctctatgc tctcttc                                      27

<210> SEQ ID NO 16
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 16
gtgcacttct taccgcaact tcggaatcgg taaggtcagg                              40

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cctgacctta ccgattccga agttgcggta agaagtgcac                              40

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttaatggtga tggtgatggt gtccacctcc ctcttcctgc cacgcaat                     48

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgtttggtg tgcgtgcggt                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acgcacacca aacagctcat                                                    20

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caccatggct tcctctatgc tctcttc                                            27

<210> SEQ ID NO 22
<211> LENGTH: 24
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 22
ttcggaatcg gtaaggtcag gaag                                            24

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgaccttacc gattccgaag ccacatatcc atctg                                35

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atcgtatggg tatccctcca aaaggccgcg ttg                                  33

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tggcaggaag agggataccc atacgatgtt cctgactatg c                         41

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttaagcagcg taatctggaa c                                               21

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgcacttctg ttcgatgtcg tgg                                             23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ccacgacatc gaacagaagt gca                                              23

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gatattatcg ctttaagccg ctgtctctct tttgtattcc                            40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gacagcggct taaagcgata atatcaaaga gaatcaatga                            40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gacaacggct taaagggata atttcacagg tcgtgatatg                            40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaaattatcc ctttaagccg ttgtctacat atatattcct                            40

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttcaacatgt gttctgtgta ttcatgtggc                                       30

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttcactgcag ttaacactca agaacttgag cattctctg                39

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttcaacatgt cttcatcttc ttcctcttgc tca                      33

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttcactgcag ttagcttccc catccgacca                          30

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttcaacatgt cttcctcttc ttcctcatcg c                        31

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttcactgcag ttagcttccc cagccaacca                          30

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttcaacatgt cgacggctcg gtct                                24

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttcactgcag ttaatgggtt gagagacgat cctca                                    35

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttcactgcag tcacacgtgg tggtggtgg                                           29

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgggaattca tggccacata tccatctgcc                                          30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccgctcgagt tacaaaaggc cgcgttggcg                                          30

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcacatcatg gtcaaaaggc acgtagtggg gaaccattc                                39

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gaatggttcc ccactacgtg cctttttgacc atgatgtgc                               39

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
attcatggca ttcatgggtt acgtt                                                25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atgaatgcca tgaatttcat ccact                                                25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggatgaaatt catggtattc atggc                                                25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gccatgaata ccatgaattt catcc                                                25

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tacctcccac aatgtttcga c                                                    21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tttcatgttc gtttcaaagg c                                                    21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctcacacacc ctcttgtctc c                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tggtatcatg aagaaggcca g                                              21

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gacctcgatc tgaactctag atcttc                                         26

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aaagcatata gagtcatcat gttgtgtaac                                     30

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggaactaatg gaagtgatgg aag                                            23

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ttccttaatc aataagatgg gagtag                                         26

<210> SEQ ID NO 58
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tagcatctga atttcataac caatctcgat acac                                34

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtagctggtc cgagaggatg                                             20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgcttattcc ccagataccg                                             20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
actgggctct ttcgagtctg                                             20

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gaccaatgca caccaaagg                                              19

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
actcataggc agtggcttgg                                             20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tttcaacatc agtcggttcg                                             20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
tgtggattca atgcgacaat                                           20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ttttgcgcag agtcaatacg                                           20

<210> SEQ ID NO 67
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
gttgaatgtg cttgcg                                               16

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ctttagcccc tgttgg                                               16

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
ggatcgctta accgtagcaa g                                         21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
agccttcgca gtagcttcat c                                         21

```
<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggccaagagg ttgataccga                                                    20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cgggtcgcac aaattgcata                                                    20

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gctctcgatt ccgattttac ag                                                 22

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aagcagcagt ttcatcgtct aac                                                23

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gaagaagaag tacccgggag g                                                  21

<210> SEQ ID NO 76
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcaagccgcc cgttct                                                        16

<210> SEQ ID NO 77
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cggaaagtga gccaagttct                                                    20

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgaaagtctc taccatccac ca                                                 22

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
aacgcctggt cttacgctac                                                    20

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtcatgtgat tttgactctt gcca                                               24

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
agagacgcga aagcgaaag                                                     19

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ctggaggagc agcaatgaa                                                     19

<210> SEQ ID NO 83
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
attgggcggt caaaattgta                                                    20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
agacggccgt aagaagaggt                                                    20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tacaacgccc aaggaagagt                                                    20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
aagaccacca tggagcatca                                                    20

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tgtctgtgga tctctctagt gc                                                 22

<210> SEQ ID NO 88
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tgagattttg tcacttcact tcaac                                              25

<210> SEQ ID NO 89
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 89
cggcgggtat ttttcttgta                                          20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ggctaaaccc cgcttaatgt                                          20

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cagtatcgct tctcgctcca g                                        21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gttctccaca accgcttggt c                                        21

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggaccccact actcgtcgta                                          20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
attgctaatt gcccgaaatg                                          20

<210> SEQ ID NO 95
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 95
gagcatgccc tacagacgta                                                 20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
caggcggatt cacatctctt                                                 20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gagcagcaat gaatgcgata                                                 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cctatggggt cgcttctgta                                                 20

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tcatggtata ctcatggatt gg                                              22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gaccacctaa ttgacaccaa cg                                              22

<210> SEQ ID NO 101
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 101
aggcctacgc ctttttgaat                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cgaaaactta cagcggcttg                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gtgttgggtt caaagctggt                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
catcggtcca cacagttgtc                                              20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gcgatgcgaa gagctttact                                              20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ccaggacctt ggacacaaat                                              20

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
cctccgattg gaaagaagaa gtttg                                         25

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tacacaaatc cgtgctccaa ctcg                                          24

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
aaaaagcacg gatacggatg                                               20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cttcttgaat gccccgatta                                               20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
atggttggtg gacgccaata                                               20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
caaccggctt gccaatgtaa                                               20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aatccccacc gcgtaatagt                                        20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
aacatgcctg aaccatttcc                                        20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
caagcgatct tttcgtaggc                                        20

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
aaagtcactc tattcacccg tct                                    23

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gcagaaatgg aagaaagagc ag                                     22

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
acggggtaga taagatattg atgg                                   24

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 119
acgccgtatt gttctctcta gc                                           22

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
tgatcaaagc ttttatgaa gcag                                          24

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ggcatctctt accatgttgt ctc                                          23

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
atttgaactt ccagcggaat ag                                           22

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gcttgtagct cagaggatta gagca                                        25

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ttgtgggcga ggagggat                                                18

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
```
tacccagtaa tccgtcttgc tc                                           22

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
atcccatgga aataaagcgg gt                                           22

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
cttctgggag gtcatgaaag g                                            21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ctccaatagc agcccaaaga g                                            21

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tttcggaaga aggggaagat                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ttcgaacgtg gaattcatca                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131

```
tagccctcgg tctattggtg                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
ggatccactt tttggggaat                                              20
```

PHOTOSYNTHETIC ORGANISMS THROUGH THE MODULATION OF GUANOSINE TETRAPHOSPHATE HOMEOSTATIS

CROSS-REFERENCE TO RELATED APPLICATIONS

This application is the National Phase of International Patent Application No. PCT/EP2017/052600, filed Feb. 7, 2017, published on Aug. 17, 2017 as WO 2017/137374 A1, which claims priority to U.S. Provisional Patent Application No. 62/292,580, filed Feb. 8, 2016. The contents of these applications are herein incorporated by reference in their entirety.

SEQUENCE LISTING

The instant application contains a Sequence Listing which has been filed electronically in ASCII format and is hereby incorporated by reference in its entirety. Said ASCII copy, created on Jan. 4, 2019, is named 065691-3600_SL.txt and is 30,412 bytes in size.

FIELD OF THE INVENTION

The present invention concerns methods and approaches for modifying guanosine tetraphosphate (ppGpp) homeostasis in photosynthetic eukaryotes, in particular plants or algae, in order to modulate senescence for the remobilisation of nitrogen and other nutrients from chloroplast, and modified photosynthetic eukaryoets thus obtained.

More particularly, the present invention may be useful in domains such as agriculture, horticulture and bioenergy (biomass, biofuel).

BACKGROUND OF THE INVENTION

More than one billion years ago a eukaryotic cell engulfed and assimilated a cyanobacterium to give rise to a new organelle, the chloroplast, and so to all the photosynthetic eukaryotes, a vast complex of primary producing organisms (algae and plants) (Reyes-Prieto et al., 2007) [1]. Following endosymbiosis many of the original cyanobacterial genes migrated to the nucleus, and the gene products were directed to the chloroplast. The ~100 genes that remained on the chloroplast genome are involved in photosynthesis, metabolism and organellar transcription and translation (Green, 2011; Jarvis and Lopez-Juez, 2013) [2, 3]. These processes involve proteins encoded by both the chloroplast and nuclear genomes. Tight co-ordination between chloroplastic and nuclear gene expression is therefore required for the biogenesis, operation and differentiation of the chloroplast (Jarvis and Lopez-Juez, 2013) [3]. Chloroplast gene expression changes dramatically during development and in response to environmental signals such as light or temperature (Liere et al., 2011; Rochaix, 2013; Pfannschmidt and Munné-Bosch, 2013; Tiller and Bock, 2014) [60-63]. Numerous mechanisms regulating the expression of specific chloroplast genes at the transcriptional and post-transcriptional levels have been identified (Liere et al., 2011; Rochaix, 2013; Pfannschmidt and Munné-Bosch, 2013; Tiller and Bock, 2014; Kindgren et al., 2012) [60-64]. However, few factors are known that control global chloroplast gene expression from within the chloroplast. Strikingly, chloroplasts have retained core elements of bacterial signaling pathways that are now thought to be involved in regulating chloroplast function (Puthiyaveetil et al., 2008; Masuda, 2012) [4, 5]. One of these pathways is the stringent response, which is probably the most important stress signaling pathway in bacteria (Dalebroux and Swanson, 2012) [6]. In bacteria the stringent response is characterized by the stress-induced accumulation of two nucleotides, guanosine penta- and tetra-phosphate (hereafter referred to as ppGpp), that directly and indirectly modulate enzymes involved in proliferative processes such as transcription, translation, and replication to ensure the safe arrest of growth and the activation of adaptive responses (Dalebroux and Swanson, 2012) [6]. Over the last ten years it has become clear that chloroplasts possess the factors necessary for a stringent-like response: ppGpp has been detected in plants and algae, and the nuclear-genomes of photosynthetic eukaryotes have been discovered to encode chloroplast-targeted RelA and SpoT homologues (RSHs), named after the enzymes responsible for ppGpp homeostasis in $E.$ $coli$ (van der Biezen et al., 2000; Atkinson et al., 2011; Tozawa and Nomura, 2011; Masuda, 2012, Takahashi et al., 2004) [7-9, 5, 10].

The nucleotide guanosine tetraphosphate (ppGpp) mediates what is probably the most important nutrient and stress signaling pathway in bacteria. Thanks to just a handful papers over recent years it is now clear that plants are also able to make ppGpp. In plants ppGpp has been proposed to play a role during stress responses because it accumulates following environmental stress and the application of stress-related plant hormones such as abcisic acid (ABA) and jasmonic acid (JA) (Takahashi et al., 2004; Ihara et al., 2015) [10, 11]. Studies using purified chloroplast enzymes and chloroplast extracts suggest that ppGpp may function in planta by inhibiting translation and/or transcription in a manner analogous to the bacterial stringent response (Sato et al., 2009, Masuda, 2012, Nomura et al., 2012, Nomura et al., 2014) [12, 5, 13, 14]. However, there remains much uncertainty about both the principal targets and effects of ppGpp in the plant under physiological conditions.

In the photosynthetic eukaryotes the RSH enzymes have diverged out into several broadly conserved families with distinct domain structures (Atkinson et al., 2011) [8]. Members of certain families are able to complement ppGpp deficient mutants of $E.$ $coli$ (Kasai et al., 2002; Tozawa et al., 2007; Mizusawa et al., 2008; Masuda et al., 2008) [15-18]. The four RSH genes found in $Arabidopsis$ show diurnal expression rhythms in photosynthetic tissues, and their expression can be regulated by application of the jasmonate precursor 2-oxo-phytodienoic acid, ABA and during environmental stress (Mizusawa et al., 2008; Chen et al., 2014; Yamburenko et al., 2015) [17, 19, 20]. However, despite their potential importance, the contribution of the different RSH genes to plant growth and development and to plant stress responses has so far received surprisingly little attention. In $Arabidopsis$, CRSH, encoding a member of calcium-binding RSH family, has been proposed to be involved in flower development, although the mechanism is not yet clear (Masuda et al., 2008) [18]. RSH2 and RSH3 have also been implicated in the ABA-mediated downregulation of chloroplast transcription (Yamburenko et al., 2015) [20].

SUMMARY OF THE INVENTION

Now, using the model plant $Arabidopsis$ $thaliana$, the inventors have found that ppGpp directly suppresses the accumulation of chloroplast transcripts and proteins in vivo, and is thus a potent controller of global chloroplast gene expression in vivo that directly reduces the quantity of chloroplast transcripts and chloroplast-encoded proteins.

Then the Inventors have demonstrated that the antagonistic functions of different plant RelA SpoT homologues (RSHs) together control ppGpp levels to regulate chloroplast function and unexpectedly are required for optimal plant growth, chloroplast volume and chloroplast breakdown and remobilization during dark-induced and developmental senescence.

PpGpp appears to act principally through the inhibition of chloroplast transcription to reduce the quantities of individual transcript available for translation, and also the total translational capacity of the chloroplast by reducing rRNA and tRNA transcript levels (FIG. 4A, B). These results are broadly in agreement with previous in vitro data and a recent study with the phytohormone ABA that suggested a link between RSH gene function and chloroplast gene transcription (Sato et al., 2009; Nomura et al., 2012; Yamburenko et al., 2015) [12, 13, 20]. A less extensive study that lead to similar conclusions was also published during the final preparation of this manuscript (Maekawa et al., 2015) [40]. Notably the inventors did not detect a major direct effect on translation, suggesting that direct inhibition of the translation apparatus does not contribute significantly to the suppression of plastid gene expression that they observed in the presence of ppGpp. Their results also indicate that, although the effect of ppGpp appears to be global, the chloroplast does not respond monotonically and that the expression of rRNA and tRNA genes may be more affected than others (FIG. 4A, 4B and FIG. 12). This shows that the main characteristics of the stringent response are conserved between plants and bacteria. They also propose on the basis of the data that they present here, the in vitro sensitivity of plant GKs to ppGpp (Nomura et al., 2014), and the GTP initiation of plant rRNA genes (Swiatecka-Hagenbruch et al., 2007; Suzuki et al., 2003) [52, 51]. that ppGpp is most likely to inhibit transcription by a similar mechanism to that found in *B. subtilis*.

The conditional expression of SYN has also allowed the inventors to uncouple the action of ppGpp from other signaling pathways and effects on chloroplast volume. This is relevant for the hormones ABA and methyl jasmonate which induce the accumulation of ppGpp but which also have large effects on nuclear gene expression that can extensively modify chloroplast function. This is apparent for PsbA which the inventors show to be downregulated at the transcriptional and steady-state levels by ppGpp (FIG. 4A, B), but which is little affected at the transcriptional level in response to ABA treatment (Yamburenko et al., 2015) [20].

In addition to its effects on the chloroplast gene expression machinery the inventors also found that, although ppGpp over accumulation strongly constrains chloroplast size and volume per cell, it does not inhibit DNA replication as in bacteria (FIG. 2). This is likely to be because, in plants, the cyanobacterial DNA primase has been replaced by a eukaryotic TWINKLE-homologue (Diray-Arce et al., 2013) [43]. This event has important implications for chloroplast evolution because it resulted in the transfer of the control of replication and division from the chloroplast to the nucleo-cytoplasmic compartment.

The inventors also reveal new roles for ppGpp and RSH enzymes during plant growth and development. They first show an unexpected role for ppGpp in regulating chloroplast function during vegetative growth (FIG. 5, 6). Although small quantities of ppGpp have previously been detected in vegetative tissues (Takahashi et al., 2004; Ihara et al., 2015) [10, 11], ppGpp is usually thought to be involved in stress responses in plants, as it is in bacteria. However, they show that the antagonistic activity of RSH enzymes is required for maintaining ppGpp levels in vegetatively growing plants (FIG. 5, 6). The resulting ppGpp pool appears to be involved in fine-tuning chloroplast gene expression and alteration of the pool by mutations in RSH genes or overexpression of the RSH1 hydrolase perturbs chloroplast transcription and can negatively affect plant growth (FIG. 5, 6). Growth may be affected by imbalances in chloroplast volume to cell volume (FIG. 6B) as well as in the composition of protein complexes and metabolic pathways that involve proteins of nuclear and chloroplast origin. Indeed, the inventors show that one of the major functions of ppGpp is in regulating the stoichiometry of the chloroplast-encoded RC subunits with the nucleus-encoded LHCII subunits of the PSII complex. This suggests that PSII assembly may be coupled to the regulation of RSH function in an autoregulatory feedback loop within the chloroplast.

Chloroplasts contain 70% of leaf nitrogen, mostly as photosynthetic proteins. During senescence chloroplasts reduce in size and activity and are then broken down as part of a tightly regulated process that remobilizes nutrients to the developing seeds (Lim et al., 2007; Pfannschmidt and Munné-Bosch, 2013) [58, 62]. Here the inventors show that ppGpp synthesis by RSH2, RSH3 and CRSH is constrained by the ppGpp hydrolase activity of RSH1, and is required for the timely initiation of senescence and for the breakdown of chlorophyll and RuBisCO (FIG. 7). RuBisCO, which is the most abundant protein in the cell and alone accounts for 20% to 30% of total nitrogen (Feller et al., 2008) [65] is subject to a complex degradation pathway during senescence that involves intra-organellar degradation as well as the intervention of extra-plastidic pathways such as autophagy (Lim et al., 2007, Ishida et al., 2014) [58, 66]. The retention of RuBisCO by plants lacking the RSH2/RSH3 ppGpp synthases or over-expressing the ppGpp hydrolase RSH1 is therefore remarkable, and indicates that ppGpp is specifically involved in the regulation of the progression of senescence, and is therefore a key player in nitrogen remobilization.

The expression level of RSH genes in the nucleus appears to govern the capacity of chloroplasts to synthesize ppGpp (FIG. 1, FIG. 18). Intriguingly, regulation of RSH expression may also modulate ppGpp homeostasis during the circadian period and in response to abiotic stress and phytohormones (Takahashi et al., 2004; Mizusawa et al., 2008; Yamburenko et al., 2015) [10, 17, 20]. The C-terminal regions of bacterial RSH enzymes are involved in the regulation of enzyme activity (Potrykus and Cashel, 2008) [67]. Recent evidence suggests that the *Arabidopsis* RSH enzymes are controlled in a similar manner: the C-terminal domain of RSH1 has a conserved TGS domain that was shown to interact with the small GTPase ObgC in a yeast two hybrid assay (Bang et al., 2012; Chen et al., 2014) [68, 19], and calcium binding at the C-terminal EF-hand domain of CRSH activates ppGpp synthase activity in vitro (Masuda et al., 2008) [18]. RSH2 and RSH3 also have extended C-terminal domains that are highly conserved in plants, and so may also be involved in regulatory interactions. Thus, RSH enzymes are likely to be able to receive signals generated during chloroplast biogenesis, operation and differentiation. In this way ppGpp levels could be rapidly modulated by changes in chloroplast status, for example in response to redox conditions, hormone signaling, temperature or changes in nutrient availability as occurs in bacteria.

PpGpp signaling is likely to operate in a similar manner in all photosynthetic eukaryotes due to the broad conservation of both ppGpp targets and RSH genes (Atkinson et al., 2011) [8]. Indeed, ppGpp signaling may have been critical for taming the bacterial ancestor of the chloroplast by preventing its growth rate from outstripping the capacity of the eukaryotic host to provide nutrients.

The results therefore show that ppGpp signaling is not only linked to stress responses in plants but is also an important mediator of cooperation between the chloroplast and the nucleocytoplasmic compartment during plant growth and development. Thus it appears that the modification of a photosynthetic eukaryote (e.g. plant or algae), for example by trangenesis, gene-editing technologies, or introgression from a wild species, can be used to alter the level of guanosine tetraphosphate (ppGpp) thereby altering nitrogen remobilization and/or senescence compared to that of a non-modified photosynthetic eukaryote, wherein said modified photosynthetic eukaryote (e.g. transgenic plant or algae) displays a delayed or accelerated nitrogen remobilization and/or senescence relative to a non-modified photosynthetic eukaryote.

Thus the present invention concerns a modified photosynthetic enkaryote (e.g. transgenic plant or algae) having a modified level of guanosine tetraphosphate (ppGpp) capable of altering nitrogen remobilization and/or senescence in a photosynthetic eukaryote, compared to that of a non-modified photosynthetic enkaryote (e.g. non-transgenic plant or algae), wherein said modified photosynthetic eukaryote displays a delayed or accelerated nitrogen remobilization and/or senescence relative to a non-modified photosynthetic eukaryote.

A "photosynthetic eukaryote" as used in the present invention is an eukaryote organism (i.e. an organism whose cells contain complex structures enclosed with membranes) which is able to perform photosynthesis (i.e. synthesis of glucose directly from carbon dioxide and water using energy from light) taking place in chloroplasts. Comprised by the term photosynthetic eukaryote are plants and most algae.

"Senescence" as used in the present invention is the organized process that eventually leads to the death of the whole or part of a photosynthetic organism. For example, during the progression of senescence, a plant reclaims and reallocates the valuable cellular building blocks that have been deposited in the leaves (and in particular the chloroplasts) and other parts of the plant during growth. Senescence can be induced by external factors (light flux, nutrient availability, water stress, temperature etc) as well as internal factors (such as by plant growth regulators: ethylene, abcissic acid, cytokinins, auxins etx) and during the course of development. Maintaining an efficient senescence process is essential for survival of an organism or its future generations.

According to a particular embodiment of the present invention, the claimed modified photosynthetic enkaryote displaying delayed nitrogen remobilization and/or senescence is transformed with a nucleic acid molecule effective in reducing levels of ppGpp. Preferably, said nucleic acid molecule encodes RSH1 or MESH hydrolase, or comprises an antisense form of a nucleic acid molecule encoding RSH2 and/or RSH3.

According to a particular embodiment of the present invention, the claimed transgenic plant displaying accelerated nitrogen remobilization and/or senescence is transformed with a nucleic acid molecule effective in increasing levels of ppGpp. Preferably, said acid nucleic molecule encodes RSH2, RSH3 and/or the bacterial RelA (SYN), or comprises an antisense form of a nucleic acid molecule encoding RSH1.

Another means for modifying levels of ppGpp in a photosynthetic eukaryote and obtaining a modified photosynthetic eukaryote comprise, for example, gene editing technologies to mutate RSH1 or RSH2/RSH3 or introgression to introduce more/less active alleles of RSH1 or RSH2/RSH3 in said photosynthetic eukaryote; using well-known methods from the art.

The present invention also concerns a seed with altered nitrogen remobilization and/or senescence characteristics produced from the modified photosynthetic eukaryote of the present invention displaying an accelerated nitrogen remobilization and/or senescence, wherein said seed comprises the nucleic acid molecule.

The present invention also concerns a seed with altered nitrogen remobilization and/or senescence characteristics, wherein said seed is transformed with a nucleic acid molecule effective in increasing levels of ppGpp. Preferably, said nucleic acid molecule encodes RSH2, RSH3 and/or the bacterial RelA (SYN), or comprises an antisense form of a nucleic acid molecule encoding RSH1.

The present invention also concerns a method for delaying nitrogen remobilization and/or senescence in a photosynthetic eukaryote, said method comprising providing a photosynthetic eukaryote transformed with a nucleic acid molecule effective in reducing ppGpp levels. Preferably, said nucleic acid molecule encodes RSH1 or MESH hydrolase, or comprises an antisense form of a nucleic acid molecule encoding RSH2 and/or RSH3.

The present invention also concerns a method for accelerating nitrogen remobilization and/or senescence in a photosynthetic eukaryote, said method comprising providing a modified photosynthetic eukaryote transformed with a nucleic acid molecule effective in increasing levels of ppGpp. Preferably, said acid nucleic molecule encodes RSH2, RSH3 and/or the bacterial RelA (SYN), or comprises an antisense form of a nucleic acid molecule encoding RSH1.

Another means for modifying levels of ppGpp in a photosynthetic eukaryote and obtaining a modified photosynthetic eukaryote comprise, for example, gene editing technologies to mutate RSH1 or RSH2/RSH3 or introgression to introduce more/less active alleles of RSH1 or RSH2/RSH3 in said photosynthetic eukaryote; using well-known methods from the art.

The present invention also concerns a method for producing a modified photosynthetic eukaryote, e.g. transgenic plant or algae, with altered nitrogen remobilization and/or senescence characteristics which comprises transformation of said photosynthetic eukaryote with a DNA construct adapted to modify ppGpp homeostasis, and subsequent selection of said modified photosynthetic eukaryote in which the nitrogen remobilization and/or senescence is either delayed or accelerated.

According to a particular embodiment of the present invention, the claimed method for producing a photosynthetic eukaryote with delayed nitrogen remobilization and/or senescence, comprises transformation of said plant with a DNA construct encoding RSH1 or MESH hydrolase, or with an antisense form of a nucleic acid molecule encoding RSH2 and/or RSH3.

According to a particular embodiment of the present invention, the claimed method for producing a photosynthetic eukaryote with accelerated nitrogen remobilization and/or senescence, comprises transformation of said plant with a DNA construct encoding RSH2, RSH3 and/or the bacterial RelA (SYN), or with an antisense form of a nucleic acid molecule encoding RSH.

Another means for modifying levels of ppGpp in a photosynthetic eukaryote and obtaining a modified photosynthetic eukaryote comprise, for example, gene editing technologies to mutate RSH1 or RSH2/RSH3 or introgression to introduce more/less active alleles of RSH1 or RSH2/RSH3 in said photosynthetic eukaryote; using well-known methods from the art.

EXAMPLES

Example 1: Material and Methods

Plant Materials and Growth

Figure 14:
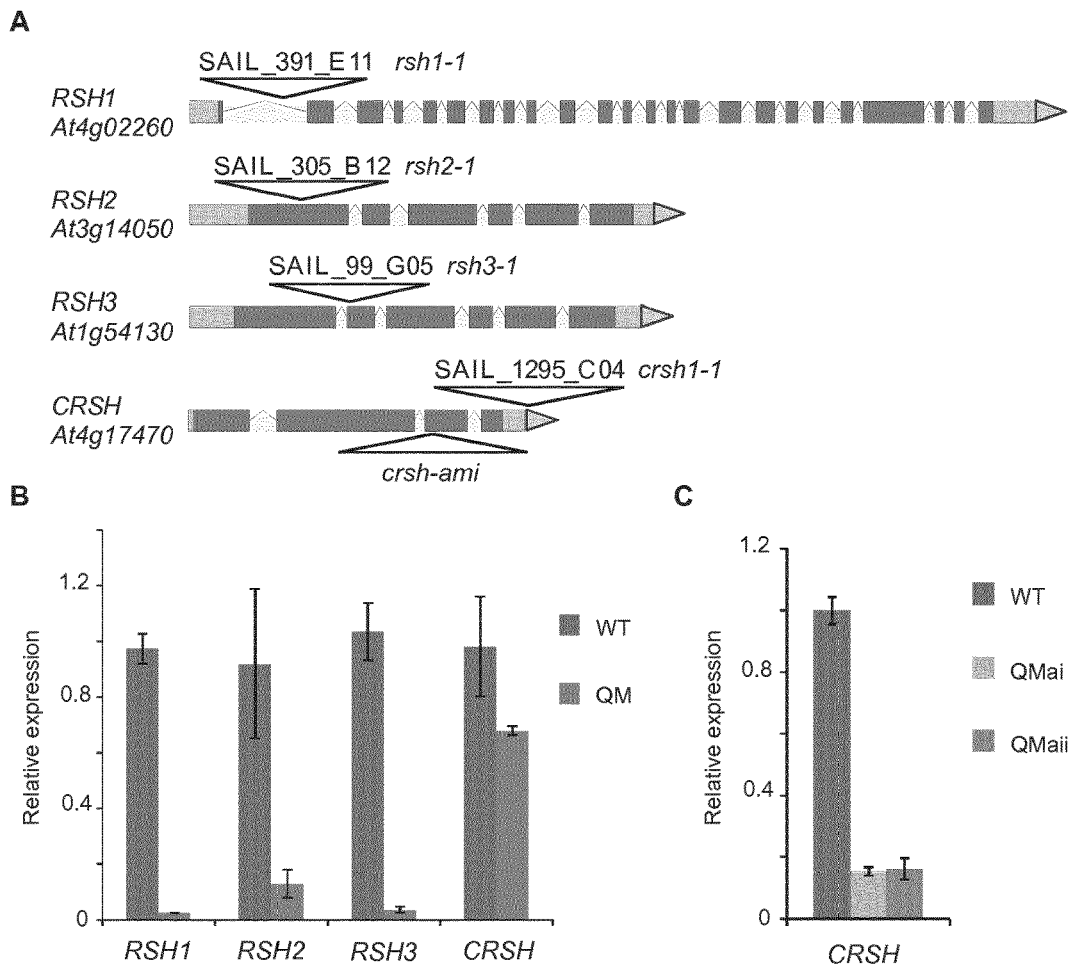
FIG. 14 represents insertion sites and gene expression in the RSH mutants. (A) The insertion sites of the *Arabidopsis* TDNA insertion mutants used in this study. Insertions for RSH1, RSH2 and RSH3 are upstream of the conserved ppGpp synthase and hydrolase domains. The region of the CRSH transcript targeted by the amiRNA in crsh-ami is indicated. qRT PCR analysis of RSH gene expression in seedlings 12 DAS using primers downstream of the insertion sites in (B) the rsh1-1 rsh2-1 rsh3-1 crsh1-1 quadruple mutant (QM) and (C) the rsh1-1 rsh2-1 rsh3-1 crsh-ami quadruple mutants (QMai and QMaii). QMai and QMaii have independent TDNA insertions for crsh-ami. Primers for qRT PCR and mutant genotyping are listed in Table 1. Expression data is normalized to 18S and PP2A reference genes. Error bars, SEM.

*Arabidopsis thaliana* T-DNA insertion mutants were provided by the Signal Insertion Mutant Library (hypertext transfer protocol://sianal.salk.edu/cgi-bin/tdnaexpress/) and were obtained via the Nottingham *Arabidopsis* Stock Centre (hypertext transfer protocol://nasc.life.nott.ac.uk/) (FIG. 14). Homozygous insertion mutants were isolated by PCR genotyping (see Table 1 for primers). Mutant lines were combined by crossing and confirmed by PCR genotyping. qRT-PCR was used to determine the accumulation of transcripts in the mutants (FIG. 14). The arc6 allele was the T-DNA insertion line SAIL_693_G04 (kindly provided by C. Laloi). For a given experiment the seeds for each line to be analyzed were harvested and bulked from multiple individual plants that had grown alongside all the other lines analyzed. For in vitro growth seeds were surface-sterilized with 75% ethanol, dried, plated onto Petri dishes containing growth medium (0.5×MS salts (Sigma-Aldrich, Saint-Quentin-Fallavier, France), 1% sucrose, 0.5 g/l MES, 0.4% phytagel (Sigma-Aldrich), pH 5.7 KOH), and placed at 4° C. for 2 days in the darkness for stratification. Plates were then transferred to a 16 hour light/8 hour dark photoperiod at 22° C./19.5° C. with 80 $\mu mol/m^2 \cdot s$ photosynthetically active radiation (PAR) fluorescent lighting. For growth in soil seeds were germinated in soil and then pricked out into pots at 4 days after germination. The plants were then grown under a 16 hour light/8 hour dark photoperiod at 18/22° C. with 115 $\mu mol/m^2 \cdot s$ PAR fluorescent lighting and a weekly application of Cotc-Lesaint fertilizer solution.

Cloning and Plant Transformation
RSH Overexpression Lines

RSH1, RSH2, and RSH3 sequences were amplified from *Arabidopsis* genomic or cDNA using Phusion polymerase (New England Biolabs, Evry, France) (see Table 1 for primers). The PCR products were then introduced by Invitrogen BP GATEWAY recombination (Life Technologies, Saint Aubin, France) into pDONR207. The entry clones were confirmed by sequencing and recombined by Invitrogen LR GATEWAY recombination (Life Technologies) into pEarleyGate103 under the control of the constitutive 35S promoter and with C-terminal GFP tag (Earley et al., 2006) [21]. The resulting constructs were transferred into *Agrobacterium* (strain GV3101) and used to transform wildtype plants by floral dipping. Transgenic plants were then selected by screening the resulting seeds for BASTA resistance. Lines stably expressing RSH genes across multiple generations were then identified by immunoblotting.

Genomic RSH3 Complementation Lines

The genomic RSH3 sequence including the 3' UTR, 5' UTR and 3.4 Kb of upstream sequence containing the promoter was amplified from *Arabidopsis* genomic DNA using Phusion polymerase (New England Biolabs). The PCR product was then introduced by Invitrogen BP GATEWAY recombination into pDONR207. The entry clone was confirmed by sequencing and recombined by Invitrogen LR GATEWAY recombination into pGGW6 (Field and Osbourn, 2008) [22] (kindly provided by Alan Herr). The resulting constructs were transferred into *Agrobacterium* (strain GV3101) and used to transform DM-23 plants by floral dipping.

Inducible SYN and ΔSYN Plants

A fragment corresponding to amino acids 1-386 of RelA was amplified from *E. coli* K-12 MG1655 by PCR. Fragments of RelA that lack the C-terminus have constitutive ppGpp synthase activity in *E. coli* (Schreiber et al., 1991) [23]. The RelA fragment was then fused by PCR to a genomic sequence coding for the 80 amino acid Rubisco small subunit 1A (RBCS1A) target peptide that is able to target chimeric proteins to the chloroplast (Lee et al., 2002) [24]. The fused PCR product (SYN) was then introduced into pENTR/D-Topo (Life Technologies). The entry clone was confirmed by sequencing. ΔSYN was then created by using site directed mutagenesis to convert the codon encoding aspartate 275 of RelA to glycine, thereby inactivating the ppGpp synthase domain (Hogg et al., 2004) [25]. SYN and ΔSYN were then recombined by Invitrogen LR GATEWAY recombination into the plant steroid inducible expression vector pOPOn2.1 (kindly provided by Ian Moore) (Craft et al., 2005) [26]. The resulting constructs were transferred into *Agrobacterium* (strain GV3101) and used to transform wild-type plants by floral dipping to give SYN and ΔSYN inducible plants. Independent lines with stable inducible expression across multiple generations were selected. All SYN lines showed similar phenotypes. One SYN (43A10) and one ΔSYN line (44613) were used in this study. The TDNA insertion sites were identified by HIT PCR (Liu and Chen, 2007) [27]: 43A10 after Chr3 23000651; 44613 after Chr3 23185643.

Inducible MESH and ΔMESH Plants

The *Drosophila melanogaster* MESH1 was PCR amplified from cDNA clone IP06414 (provided by the *Drosophila* Genomics Resource Center). The MESH1 PCR fragment was fused by PCR to a genomic sequence coding for the RBCS1A target peptide and introduced into pENTR/D-Topo. The entry clone (MESH) was confirmed by sequencing. ΔMESH was created by using site directed mutagenesis to convert the codon encoding histidine 62 of MESH to phenylalanine, thereby inactivating the ppGpp hydrolase domain (Sun et al., 2010) [28]. cytMESH was constructed as for MESH but without the Rubisco small subunit target peptide. The resulting clones were then recombined by Invitrogen LR GATEWAY recombination into the plant expression vector pOPOn2, transferred into *Agrobacterium* (strain GV3101) and used to transform wildtype plants by floral dipping to give inducible MESH, ΔMESH and cytMESH plants. Independent lines with stable inducible expression across multiple generations were selected.

Artificial microRNA Lines

An artificial microRNA targeting CRSH was constructed as previously described (Schwab et al., 2006) [29] and introduced into pDONR207. The clones were sequenced, recombined into pEarleyGate 103 under the control of the constitutive 35S promoter, and used to transform TM-123 and wildtype plants by floral dipping to give QMa and crsh-ami plants. Twenty independent lines were selected, and reduction of CRSH expression confirmed by qRT PCR in lines used for further experiments (FIG. 14).

Plasmids for *E. coli* Hydrolase Tests

MESH and ΔMESH sequences were amplified from plasmids pENTR-MESH and pENTR-ΔMESH (see above). The DNA fragments were digested with EcoRI and XhoI enzymes and introduced into pBAD24 (Guzman et al., 1995)

[30] opened with EcoRI and SalI enzymes. The mature RSH1, RSH2, RSH3 and CRSH coding sequences were amplified from *Arabidopsis* cDNA using Phusion polymerase (New England Biolabs), and the mature RSH1-GFP, RSH2-GFP and RSH3-GFP coding sequences were amplified from the pEarleyGate103 constructs described above for plant transformation or constructed by fusion PCR. The PCR fragments were digested with PciI and PstI and introduced into pBAD24 opened with NcoI and PstI. Vectors encoding inactive forms of the enzymes were made by mutating essential residues in the synthase domains in RSH2 (D451G) and RSH3 (D452G), and the hydrolase domain in RSH1 (R166A) (Hogg et al., 2004) [25]. All the introduced sequences were confirmed by sequencing.

RNA Isolation and qRT PCR Analysis

RNA was extracted from plant tissue using TriReagent (Sigma-Aldrich) and treated with DNAse. cDNA was then synthesized using Primescript RT Reagent Kit (Takara) with oligodT and/or random hexamer primers. qRT-PCR was performed using SYBR Premix Ex-Taq II reagent (Takara Bio, Japan) in a BioRad CFX96 Real Time System (see Table 1 for primer pairs). Data was analyzed using the BioRad CFX Manager software. Primer pair efficiency was calculated using PCR Miner (Zhao and Fernald, 2005) [31]. Expression values were normalized to one or more reference genes using the ΔΔCt method adjusted for amplification efficiency. qRT PCR was also used to measure plastid DNA content as described elsewhere (Rowan and Bendich, 2011) [32]. For RNA gels (FIG. 1D and FIG. 2E) total RNA was denatured by heating at 70° C. for 10 minutes in 47.5% formamide, 0.25 mM EDTA, and 0.0125% SDS before loading.

Extraction and Quantification of ppGpp by UPLC-MS/MS ppGpp extraction was performed according to Ihara et al., 2015 [11] with minor modifications. Approximately 100 mg of plant tissue was extracted in 3 ml 2M formic acid on ice. After 30 minutes 3 ml of 50 mM ammonium acetate pH 4.5 was added and the sample split into two portions to one of which was added 25 µl 500 nM ppGpp (Trilink, USA). Samples were then passed through prepared 1 ml Oasis WAX columns (Waters, Guyancourt, France), washed with 1 ml 50 mM ammonium acetate pH 4.5 and 1 ml MeOH, and eluted with 1 ml MeOH/$H_2O$/$NH_4OH$ (20:70:10). The eluate was lyophilized, resuspended in 200 µl water and filtered through a NucleoSpin column (Machery and Nagel, Hoerdt, France). The eluate was then adjusted to 6% acetonitrile and 10 µl injected into an Acquity UPLC system (Waters) and separated on a Kinetex C18 (100×2.10 mm) with 2.6 µm particle size (Phenomenex, Le Pecq, France). Mass spectrometric detection was performed with a SYNAP G2S mass spectrometer (Waters) with the ESI ion source set to negative ion mode. ppGpp was detected in tof MRM mode. The mass of the chosen parent ion (601.95 m/z) was selected by the quadrupole, and fragmented in the collision cell to the target ion (158.95 m/z). The cone voltage was at 30V and the collision energy followed a power ramp from 15 to 40 eV. ppGpp levels were then quantified against a standard curve and adjusted using the recovery rate calculated for individual samples. To avoid positive quantification bias in samples containing little ppGpp (such as the WT) the calibration curve was modified to the form y=ax rather than y=ax+b which was used previously (Ihara et al., 2015) [11]. This approach produced results that corresponded well with ppGpp measurements on more concentrated samples derived from large scale extractions, and also with previous measurements of ppGpp in plants (Takahashi et al., 2004) [10]. Large scale extractions were performed on 500 mg of plant sample using fivefold greater volumes and purification on 5 ml Oasis WAX columns. After lyophilisation samples were suspended in 200 µl volume of water, as above, to give a five-fold increase in analyte concentration.

Metabolic Labelling of Newly Synthesised RNA

Newly synthesised RNA was labelled with 4SU was performed as described previously with some modifications (Sidaway-Lee et al., 2014). 12 DAS seedlings were labelled 15 minutes after dawn by flooding with 1.5 mM 4SU (Carbosynth, Compton, UK) in 0.5×MS salts and 0.01% Silwet. Seedlings were frozen in liquid nitrogen after exactly 45 minutes. Total RNA was then extracted using TriReagent (Life Technologies). 75 ug of total RNA was biotinylated in 10 mM Tris-Cl pH 7.4, 1 mM EDTA, and 0.2 mg/ml in EZ-Link HPDP-Biotin (Life Technologies) for 1.5 hr at room temperature. Unbound biotin was removed by chloroform extraction using phase lock gel (5 Prime, Hilden, Germany) and the RNA was precipitated from the aqueous phase by adding ⅒ volume of 5 M NaCl and 1.1 volumes of isopropanol. Biotinylated RNA was then was separated from unlabelled RNA using streptavidin coated magnetic beads (New England Biolabs, Évry, France). 75-100 µg of biotinylated RNA was added to the beads and the solution incubated for 20 minutes at room temperature. The beads were washed three times with 1 ml of 65° C. washing buffer (1 M NaCl, 100 mM Tris-Cl pH 7.4, 10 mM EDTA) and three times with 1 ml of room temperature washing buffer. Labelled RNA was then eluted by the addition of two portions of 5% β-mercaptoethanol. RNA was precipitated in the presence of glycogen by adding ⅒ volume of 5 M NaCl and 1.1 volumes of isopropanol and quantified using QUBIT RNA HS (Thermo Fisher Scientific, Villebon-sur-Yvette, France).

Metabolic Labeling of Newly Synthesized Proteins with Puromycin

12 DAS in vitro grown plants were treated by flooding plates with 30 µM dexamethasone or 1 mM lincomycin for 3 minutes and then returned to growing conditions. After a fixed time plants were removed from the plates and vacuum infiltrated with the labeling mixture (1 mM $KH_2PO_4$ pH 6.3, 0.1% Tween-20, 50 µg/ml puromycin (Apollo Scientific, Stockport, UK) and 100 µg/ml cycloheximide). Plants were incubated in petri dishes for exactly 1 hr under growing conditions before being frozen in liquid nitrogen. A fraction highly enriched in whole chloroplasts was then extracted from the frozen tissue essentially as previously described by homogenization in homogenization buffer (10 mM tricine KOH pH 7.5, 0.4 M sucrose, 10 mM NaCl, 5 mM $MgCl_2$, 100 mM ascorbate, 0.2 mM PMSF, 1 mM benzamidine, 5 mM aminocaproic acid, 1 mM lincomycin), filtration through a 30 µM mesh, and centrifugation (Pesaresi, 2011) [33]. Purified chloroplasts were then used directly for protein extraction and immunoblotting.

Chlorophyll Quantification

Frozen plant powder or leaf discs were extracted with ice-cold 90% acetone saturated with sodium carbonate. The extract was adjusted to 80% acetone and the absorbance measured between 350 and 750 nm in a Varian Cary 300 spectrophotometer (Agilent, Les Ulis, France). Chlorophyll concentrations and chlorophyll a/b ratios were calculated using a fitting algorithm as described previously (Croce et al., 2002) [34].

Chlorophyll Fluorescence

Plants were dark adapted for 20 minutes and chlorophyll fluorescence measured in an imaging fluorometer Fluorcam FC 800-O (Photon System Instruments, Drasov, Czech Republic). The standard protocol included in the supplied Fluorcam 7 software was used to image F0 and Fm. PSII maximum quantum yield was calculated as (Fm−F0)/Fm.

Protein Separation and Immunoblotting

Proteins were extracted in 2×SDS sample buffer (100 mM Tris-HCl pH 6.8, 25 mM EDTA, 4% SDS, 20% glycerol) by heating at 85° C. for 5 minutes. Protein concentration was measured using the BCA assay (Sigma-Aldrich). Proteins were then reduced with 5% betamercaptoethanol and equal quantities separated by SDS-PAGE and either stained with Coomassie Brilliant Blue or transferred onto nitrocellulose membranes according to the manufacturer's instructions (Bio-Rad, Marnes-La-Coquette, France). Transfer homogeneity was confirmed by Ponceau Red staining. After incubation with 5% nonfat milk in TBST (10 mM Tris, pH 8.0, 150 mM NaCl, 0.1% Tween 20) for 60 min, the membrane was incubated in the same buffer with antibodies against RelA (kindly provided by M. Cashel), PsbA (Agrisera, Vännäs, Sweden; polyclonal), AtpB (Agrisera, polyclonal), PetA (Agrisera, polyclonal), LHCA1 (Agrisera, polyclonal), LHCA4 (Agrisera, polyclonal), LHCB4 (Agrisera, polyclonal), PsaC (Agrisera, polyclonal), GFP (Roche, Boulogne Billancourt, France; clones 7.1 and 13.1), HA (Sigma-Aldrich, clone HA-7) or puromycin (kindly provided by P. Pierre and E. Gatti, clone 12D10) for 1 hr at room temperature. The membrane was washed three times for 5 min in TBST and then incubated with horseradish peroxidase conjugated anti-mouse or anti-rabbit antibodies for 1 hr at room temperature. The membrane was then washed a further three times in TBST, developed using Immobilon ECL substrate (Millipore, Molsheim, France), and imaged with a Fusion FX7 imager (Vilber Lourmat, Collegien, France). For quantitative analysis bands or lanes from the raw 16-bit TIFF images were integrated using ImageJ analysis software (National Institutes of Health, USA).

Chloroplast Number and Volume Analysis

Protoplasts were made from leaves by digestion with cellulase and macerozyme (Yoo et al., 2007) [35], and examined in resuspension solution within 16 hours using a light microscope. Chloroplast volume was approximated to a hemisphere ($\frac{2}{3}\pi r^3$) and the Feret diameter used calculate the radius. Average chloroplast volume was calculated for 300 chloroplasts for each sample within an experiment. This was then used to calculate total chloroplast volume in individual protoplasts. Chloroplast area was also analyzed in fixed cells as described previously (Pyke and Leech, 1991) [36].

Synthase and Hydrolase Tests in E. coli

For testing ppGpp synthase activity plasmids were transformed either into E. coli strain EB425 (MG1655ΔrelAΔspoT) (Wahl et al., 2011) [37] and grown at 37° C. on plates of M9 minimal media without amino acids, or into E. coli strain EB421 (MG1655ΔrelA) (Wahl et al., 2011) [37] and grown at 37° C. on SMG media as described previously (Battesti and Bouveret, 2006) [38].

For testing ppGpp hydrolase activity plasmids were transformed into E. coli strain EB544 (MG1655ΔrelAΔspoT203) (My et al., 2013) [39]. Transformants could not be obtained for plasmids containing RSH2 or RSH3 presumably due to leaky expression and the accumulation of lethal levels of ppGpp. Precultures from independent colonies for each replicate were diluted in 150 μl LB containing ampicillin in a 96 well microplate, and growth was performed in a TECAN automated plate reader (TECAN, Lyon, France) at 37° C. and optical density was measured at 600 nm every 10 minutes.

Senescence Induction

For senescence induction all fully expanded leaves were detached from 3-4 week old long day grown or 6-8 week old short day grown plants and placed together in individual Petri dishes with moistened filter paper. The Petri dishes were then wrapped in foil and placed in the dark at 18-22° C. Leaves were analyzed after 3-6 days. For analysis all the leaves from each plant were ground to a fine powder with liquid nitrogen before measurement of chlorophyll levels. At least three plants were analyzed per line and per treatment.

Statistical Testing

Sample sizes were chosen to identify the smallest effect size that was practically obtainable. The two-way Student t-test was used to compare control samples with treatment samples. ANOVA was used to compare multiple sample means, with the Dunnett test post hoc. For samples with non-normal distributions (Jarque-Bara test) the non-parametric Kruskal-Wallis test was used with the Dunn test post hoc.

Image Processing

Digitally acquired images were processed in Adobe Photoshop or Net.Paint and assembled into figures in Adobe Illustrator. The Adobe Photoshop white point function was used for the images in FIGS. 1A, 2A and 7C. For visualization of immunoblotting results, the levels of raw non-saturated 16-bit TIFF images were adjusted in a linear fashion to accurately reveal the bands, converted to 8-bit, black-to-white inverted and cropped before placing into the figure panels.

Accession Numbers

Sequence data from this article can be found for Arabidopsis genes in The Arabidopsis Information Resource protocol://www.arabidopsis.org/) under the following accession numbers At4g02260 (RSH1), At3g14050 (RSH2), At g54130 (RSH3), At3g17470 (CRSH), AtCg00020 (PsbA), At1g29910-At1g29920-Atg29930 (LHCB1), At2g40100-At3g08940-At5g01530 (LHCB4), AtCg00340 (PsaB), At3g47479 (LHHCA4), AtCg00120 (AtpA), AtCg00540 (PeA), AtCg00490 (RBICL), At1g67090 (RBCS1A), At5g42480 (ARC6); for E. coli genes in EcoCyc (hypertext transfer protocol://ecocyc.org/) under the accession numbers EG10835 (ReA) and EG10966 (SpoT), and for Drosophila genes in Flybase (hypertext transfer protocol://flybase.org/) under accession number FBgn0039650 (Mesh1). Accessions for genes used in qRT-PCR experiments can be found in Table 1.

TABLE 1

| Cloning | Accession No | Primers used | SEQ ID NO: |
|---|---|---|---|
| RSH cloning for plant expression | | | |
| RSH1 B1 F | At4g02260 | ggggacaagtttgtacaaaaaagcaggcCTTCCTCTGCTTCTTCTTCTTCAC | 1 |
| matureRSH1 B1 F | At4g02260 | ggggacaagtttgtacaaaaaagcaggcttcATGTGTTCTGTGTATTCATGTGGCA | 2 |

TABLE 1-continued

| Cloning | Accession No | Primers used | SEQ ID NO: |
|---|---|---|---|
| RSH1 B2 R | At4g02260 | ggggaccactttgtacaagaaagctgggttTAAACACTCAAGAACTTGAGCATTC | 3 |
| RSH2 B1 F | At3g14050 | ggggacaagtttgtacaaaaaagcaggcAAAGATTAATTTTCGTCCTTAAAGC | 4 |
| matureRSH2 B1 F | At3g14050 | ggggacaagtttgtacaaaaaagcaggcTTCATGGCTTCTTCATCTTCTTCCTC | 5 |
| RSH2 B2 R | At3g14050 | ggggaccactttgtacaagaaagctgggttTAAGCTTCCCCATCCGACC | 6 |
| RSH3 B1 F | At1g54130 | ggggacaagtttgtacaaaaaagcaggcGATTGGTTTATTTCTAGTTTCTTC | 7 |
| pRSH3 B1 F | At1g54130 | ggggacaagtttgtacaaaaaagcaggcAGAATCATCCCTGGTTGTGTCAAA | 8 |
| matureRSH3 B1 F | At1g54130 | ggggacaagtttgtacaaaaaagcaggcTTCATGGCTTCTTCCTCTTCTTCCTC | 9 |
| RSH3 B2 R | At1g54130 | ggggaccactttgtacaagaaagctgggttATAGCTTCCCCAGCCAACC | 10 |
| RSH3 II B2 R | At1g54130 | ggggaccactttgtacaagaaagctgggttAGAATGTAAGAGAATCAAATATTAATGACCA | 11 |
| CRSH B1 F | At3g17470 | ggggacaagtttgtacaaaaaagcaggcGCCTCAATTTTCAAAATCAATCTC | 12 |
| matureCRSH B1 F | At3g17470 | ggggacaagtttgtacaaaaaagcaggcttcATGTCGACGGCTCGGTCT | 13 |
| CRSH B2 R | At3g17470 | ggggaccactttgtacaagaaagctgggttTAAATGGGTTGAGAGACGATCC | 14 |
| SYN and ΔSYN for plant expression | | | |
| SYN-1a (TP-F) | | CACCATGGCTTCCTCTATGCTCTCTTC | 15 |
| SYN-1b (TP-R) | | GTGCACTTCTTACCGCAACTTCGGAATCGGTAAGGTCAGG | 16 |
| SYN-1c (ReIA-F) | | CCTGACCTTACCGATTCCGAAGTTGCGGTAAGAAGTGCAC | 17 |
| SYN-1d (ReIA-R) | | TTAATGGTGATGGTGATGGTGTCCACCTCCCTCTTCCTGCCACGCAAT | 18 |
| SYN-D275G-F | | CTGTTTGGTGTGCGTGCGGT | 19 |
| SYN-D275G-R | | ACGCACACCAAACAGCTCAT | 20 |
| MESH, ΔMESH and cytMESH for plant expression | | | |
| MESH-1a (TP-F) | | CACCATGGCTTCCTCTATGCTCTCTTC | 21 |
| MESH-1b (TP-R) | | TTCGGAATCGGTAAGGTCAGGAAG | 22 |
| MESH-1c (MESH-F) | | TGACCTTACCGATTCCGAAGCCACATATCCATCTG | 23 |
| MESH-1d (MESH-R) | | ATCGTATGGGTATCCCTCCAAAAGGCCGCGTTG | 24 |
| MESH-1e (HA-F) | | TGGCAGGAAGAGGGATACCCATACGATGTTCCTGACTATGC | 25 |
| MESH-1f (HA-R) | | TTAAGCAGCGTAATCTGGAAC | 26 |
| MESH-H62F-F | | TGCACTTCTGTTCGATGTCGTGG | 27 |
| MESH-H62F-R | | CCACGACATCGAACAGAAGTGCA | 28 |
| amiRNA for CRSH silencing | | | |
| CRSHaI | At3g17470 | gaTATTATCGCTTTAAGCCGCTGtctctcttttgtattcc | 29 |
| CRSHaII | At3g17470 | gaCAGCGGCTTAAAGCGATAATAtcaaagagaatcaatga | 30 |
| CRSHaIII | At3g17470 | gaCAACGGCTTAAAGGGATAATTtcacaggtcgtgatatg | 31 |
| CRSHaIV | At3g17470 | gaAATTATCCCTTTAAGCCGTTGtctacatatatattcct | 32 |
| RSH cloning for E.coli expression | | | |
| RSH1 PciI F | | TTCAACATGTGTTCTGTGTATTCATGTGGC | 33 |
| RSH1 PstI R | | TTCACTGCAGTTAACACTCAAGAACTTGAGCATTCTCTG | 34 |

TABLE 1-continued

| Cloning | Accession No | Primers used | SEQ ID NO: |
|---|---|---|---|
| RSH2 PciI F | | TTCAACATGTCTTCATCTTCTTCCTCTTGCTCA | 35 |
| RSH2 PstI R | | TTCACTGCAGTTAGCTTCCCCATCCGACCA | 36 |
| RSH3 PciI F | | TTCAACATGTCTTCCTCTTCTTCCTCATCGC | 37 |
| RSH3 PstI R | | TTCACTGCAGTTAGCTTCCCCAGCCAACCA | 38 |
| CRSH PciI F | | TTCAACATGTCGACGGCTCGGTCT | 39 |
| CRSH PstI R | | TTCACTGCAGTTAATGGGTTGAGAGACGATCCTCA | 40 |
| GFP PstI R | | TTCACTGCAGTCACACGTGGTGGTGGTGG | 41 |
| MESH F | | TGGGAATTCATGGCCACATATCCATCTGCC | 42 |
| MESH R | | CCGCTCGAGTTACAAAAGGCCGCGTTGGCG | 43 |
| RSH1 R166A F | | GCACATCATGGTCAAAAGGCACGTAGTGGGGAACCATTC | 44 |
| RSH1 R166A R | | GAATGGTTCCCCACTACGTGCCTTTTGACCATGATGTGC | 45 |
| RSH2 D451G F | | ATTCATGGCATTCATGGGTTACGTT | 46 |
| RSH2 D451G R | | ATGAATGCCATGAATTTCATCCACT | 47 |
| RSH3 D452G F | | GGATGAAATTCATGGTATTCATGGC | 48 |
| RSH3 D452G R | | GCCATGAATACCATGAATTTCATCC | 49 |
| Genotyping | | | |
| rsh1-1-F | At4g02260 | TACCTCCCACAATGTTTCGAC | 50 |
| rsh1-1-R | At4g02260 | TTTCATGTTCGTTTCAAAGGC | 51 |
| rsh2-1-F | At3g14050 | CTCACACACCCTCTTGTCTCC | 52 |
| rsh2-1-R | At3g14050 | TGGTATCATGAAGAAGGCCAG | 53 |
| rsh3-1-F | At1g54130 | GACCTCGATCTGAACTCTAGATCTTC | 54 |
| rsh3-1-R | At1g54130 | AAAGCATATAGAGTCATCATGTTGTGTAAC | 55 |
| crsh-1-F | At3g17470 | GGAACTAATGGAAGTGATGGAAG | 56 |
| crsh-1-R | At3g17470 | TTCCTTAATCAATAAGATGGGAGTAG | 57 |
| SAIL-LB3 | | TAGCATCTGAATTTCATAACCAATCTCGATACAC | 58 |
| qRT PCR | | | |
| 16S f | AtCg00920 AtCg01210 | GTAGCTGGTCCGAGAGGATG | 59 |
| 16S r | AtCg00920 AtCg01210 | TGCTTATTCCCCAGATACCG | 60 |
| 18S f | At2g01010 | ACTGGGCTCTTTCGAGTCTG | 61 |
| 18S r | At2g01010 | GACCAATGCACACCAAAGG | 62 |
| 23S f | AtCg01180 AtCg00950 | ACTCATAGGCAGTGGCTTGG | 63 |
| 23S r | AtCg01180 AtCg00950 | TTTCAACATCAGTCGGTTCG | 64 |
| ACCD f | AtCg00500 | TGTGGATTCAATGCGACAAT | 65 |
| ACCD r | AtCg00500 | TTTTGCGCAGAGTCAATACG | 66 |
| APT1 f | At1g27450 | GTTGAATGTGCTTGCG | 67 |
| APT1 r | At1g27450 | CTTTAGCCCCTGTTGG | 68 |
| ATPB f | AtCg00480 | GGATCGCTTAACCGTAGCAAG | 69 |

TABLE 1-continued

| Cloning | Accession No | Primers used | SEQ ID NO: |
|---|---|---|---|
| ATPB r | AtCg00480 | AGCCTTCGCAGTAGCTTCATC | 70 |
| CLPP1 f | AtCg00670 | GGCCAAGAGGTTGATACCGA | 71 |
| CLPP 1 r | AtCg00670 | CGGGTCGCACAAATTGCATA | 72 |
| CRSH f | At3g17470 | GCTCTCGATTCCGATTTTACAG | 73 |
| CRSH r | At3g17470 | AAGCAGCAGTTTCATCGTCTAAC | 74 |
| LHCA1 f | At3g54890 | GAAGAAGAAGTACCCGGGAGG | 75 |
| LHCA1 r | At3g54890 | GCAAGCCGCCCGTTCT | 76 |
| LHCB1.1 f | At1g29920 | CGGAAAGTGAGCCAAGTTCT | 77 |
| LHCB1.1 r | At1g29920 | TGAAAGTCTCTACCATCCACCA | 78 |
| LHCB2.2 f | At2g05070 | AACGCCTGGTCTTACGCTAC | 79 |
| LHCB2.2 r | At2g05070 | GTCATGTGATTTTGACTCTTGCCA | 80 |
| PDNA f |  | AGAGACGCGAAAGCGAAAG | 81 |
| PDNA r |  | CTGGAGGAGCAGCAATGAA | 82 |
| PETB f | AtCg00720 | ATTGGGCGGTCAAAATTGTA | 83 |
| PETB r | AtCg00720 | AGACGGCCGTAAGAAGAGGT | 84 |
| PETC f | At4g03280 | TACAACGCCCAAGGAAGAGT | 85 |
| PETC r | At4g03280 | AAGACCACCATGGAGCATCA | 86 |
| MAT f | At2g30200 | TGTCTGTGGATCTCTCTAGTGC | 87 |
| MAT r | At2g30200 | TGAGATTTTGTCACTTCACTTCAAC | 88 |
| NDHF f | AtCg01010 | CGGCGGGTATTTTCTTGTA | 89 |
| NDHF r | AtCg01010 | GGCTAAACCCCGCTTAATGT | 90 |
| PP2A f | At1g13320 | CAGTATCGCTTCTCGCTCCAG | 91 |
| PP2A r | At1g13320 | GTTCTCCACAACCGCTTGGTC | 92 |
| PSAB f | AtCg00340 | GGACCCCACTACTCGTCGTA | 93 |
| PSAB r | AtCg00340 | ATTGCTAATTGCCCGAAATG | 94 |
| PSAC f | AtCg01060 | GAGCATGCCCTACAGACGTA | 95 |
| PSAC r | AtCg01060 | CAGGCGGATTCACATCTCTT | 96 |
| PSBA f | AtCg00020 | GAGCAGCAATGAATGCGATA | 97 |
| PSBA r | AtCg00020 | CCTATGGGGTCGCTTCTGTA | 98 |
| PSBD f | AtCg00270 | TCATGGTATACTCATGGATTGG | 99 |
| PSBD r | AtCg00270 | GACCACCTAATTGACACCAACG | 100 |
| PSBK f | AtCg00070 | AGGCCTACGCCTTTTTGAAT | 101 |
| PSBK r | AtCg00070 | CGAAAACTTACAGCGGCTTG | 102 |
| RBCL f | AtCg00490 | GTGTTGGGTTCAAAGCTGGT | 103 |
| RBCL r | AtCg00490 | CATCGGTCCACACAGTTGTC | 104 |
| RPOA f | AtCg00740 | GCGATGCGAAGAGCTTTACT | 105 |
| RPOA r | AtCg00740 | CCAGGACCTTGGACACAAAT | 106 |
| RBCS1A f | At1g67090 | CCTCCGATTGGAAAGAAGAAGTTTG | 107 |

TABLE 1-continued

| Cloning | Accession No | Primers used | SEQ ID NO: |
|---|---|---|---|
| RBCS1A r | At1g67090 | TACACAAATCCGTGCTCCAACTCG | 108 |
| RPOB f | AtCg00190 | AAAAAGCACGGATACGGATG | 109 |
| RPOB r | AtCg00190 | CTTCTTGAATGCCCCGATTA | 110 |
| RPL21C f | At1g35680 | ATGGTTGGTGGACGCCAATA | 111 |
| RPL21C r | At1g35680 | CAACCGGCTTGCCAATGTAA | 112 |
| RPS14 f | AtCg00330 | AATCCCCACCGCGTAATAGT | 113 |
| RPS14 r | AtCg00330 | AACATGCCTGAACCATTTCC | 114 |
| RPS18 f | AtCg00650 | CAAGCGATCTTTTCGTAGGC | 115 |
| RPS18 r | AtCg00650 | AAAGTCACTCTATTCACCCGTCT | 116 |
| RSH 1 f | At4g02260 | GCAGAAATGGAAGAAAGAGCAG | 117 |
| RSH 1 r | At4g02260 | ACGGGGTAGATAAGATATTGATGG | 118 |
| RSH2 f | At3g14050 | ACGCCGTATTGTTCTCTCTAGC | 119 |
| RSH2 r | At3g14050 | TGATCAAAGCTTTTTATGAAGCAG | 120 |
| RSH3 f | At1g54130 | GGCATCTCTTACCATGTTGTCTC | 121 |
| RSH3 r | At1g54130 | ATTTGAACTTCCAGCGGAATAG | 122 |
| TRN R f | AtCg00110 AtCg00980 AtCg01150 | GCTTGTAGCTCAGAGGATTAGAGCA | 123 |
| TRNR r | AtCg00110 AtCg00980 AtCg01150 | TTGTGGGCGAGGAGGGAT | 124 |
| TRNY/D F | AtCg00240 | TACCCAGTAATCCGTCTTGCTC | 125 |
| TRNY/D R | AtCg00240 | ATCCCATGGAAATAAAGCGGGT | 126 |
| UPL7 f | At3g53090 | CTTCTGGGAGGTCATGAAAGG | 127 |
| UPL7 r | At3g53090 | CTCCAATAGCAGCCCAAAGAG | 128 |
| YCF1 f | AtCg01000 AtCg01130 | TTTCGGAAGAAGGGGAAGAT | 129 |
| YCF1 r | AtCg01000 AtCg01130 | TTCGAACGTGGAATTCATCA | 130 |
| YCF2 f | AtCg00860 | TAGCCCTCGGTCTATTGGTG | 131 |
| YCF2 r | AtCg00860 | GGATCCACTTTTTGGGGAAT | 132 |

Table 1 (end)

Example 2: ppGpp Controls Global Chloroplast Function

Figure 8:
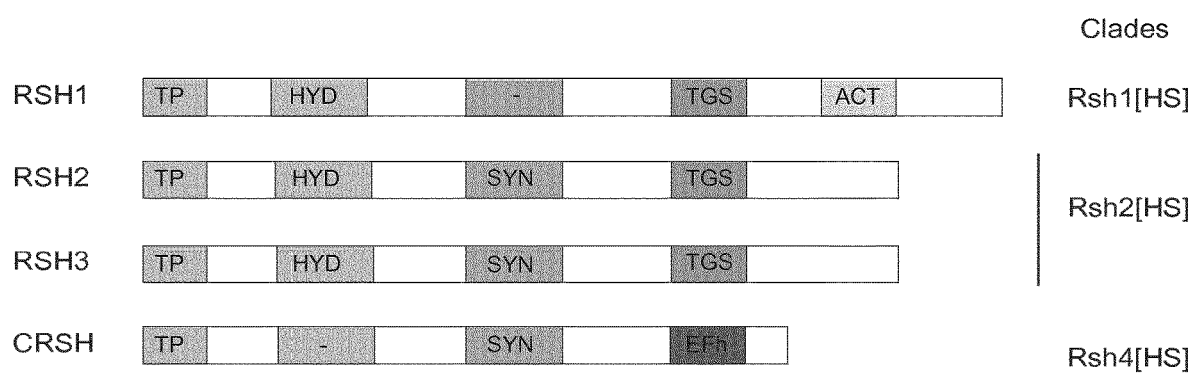
FIG. 8 represents the $Arabidopsis$ RSH domain structure. Schematic representation of the domain structure of the $Arabidopsis$ RSH enzymes, adapted from Atkinson et al., 2011 [8]. Membership of RSH genes clades is indicated to the right using the nomenclature of Atkinson et al., 2011 [8]. TP, chloroplast target peptide; HYD, ppGpp hydrolase domain; SYN, ppGpp synthase domain; TGS, TGS regulatory domain; ACT, ACT regulatory domain; EFh, calcium binding EF hand. RSH1 has a serine substitution in the ppGpp synthase domain that abolishes ppGpp synthase activity (Mizusawa et al., 2008) [17]
Figure 9:
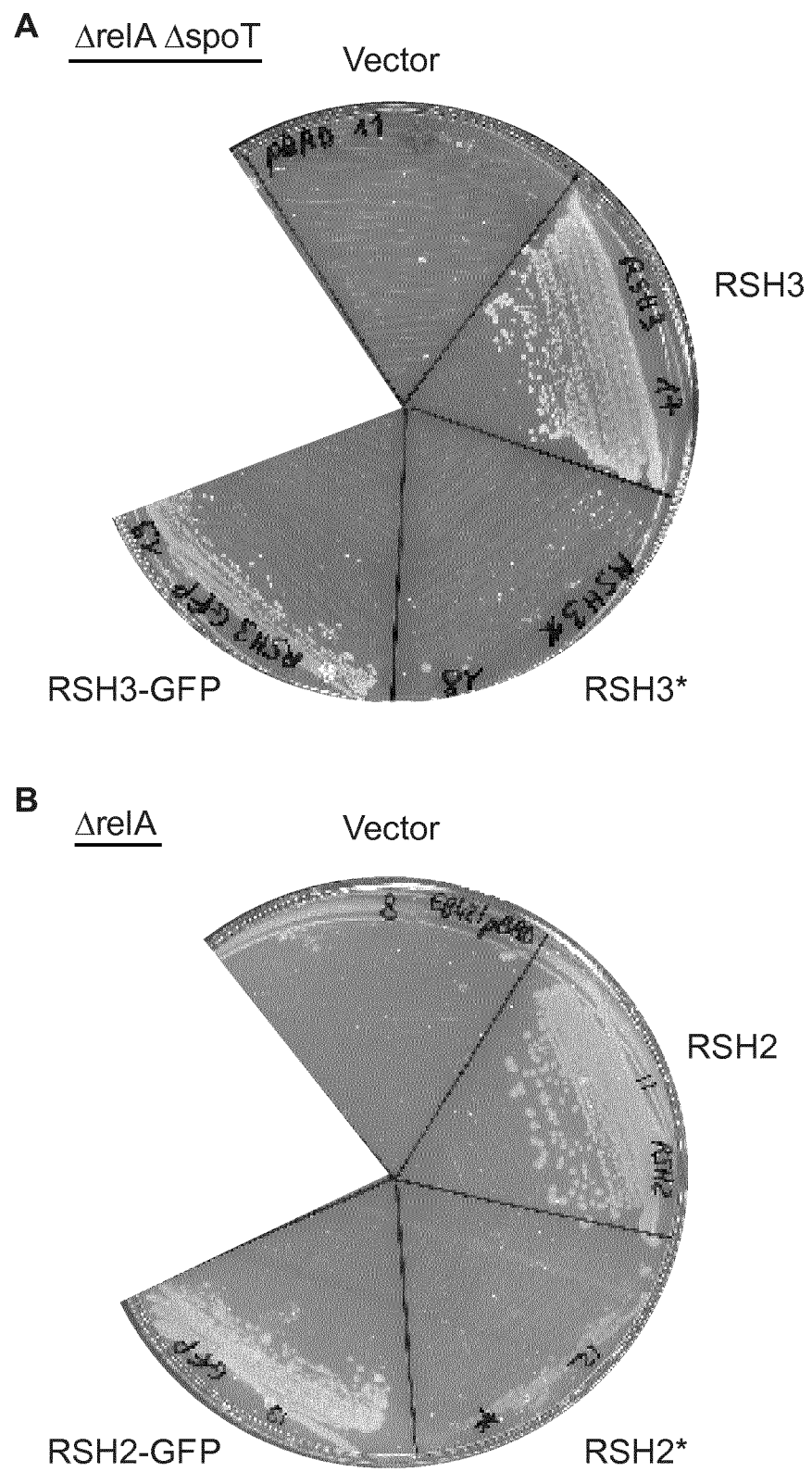
FIG. 9 represents complementation of ppGpp deficient $E.$ $coli$ mutants by the expression of RSH2 and RSH3 GFP fusion proteins (A) Expression of the mature form of RSH3 or an RSH3 GFP fusion complemented the growth of a ppGpp null (ΔrelA ΔspoT) mutant on minimal media without amino acids. Mutation of the ppGpp synthase active site abolished complementation (RSH3*). Bacteria containing the active RSH2 expression constructs could not be recovered in the ppGpp null mutant, as previously described (Mizusawa et al., 2008) [17]. Therefore RSH2 was tested in a ppGpp deficient relA mutant (ΔrelA) on SMG medium (B). Expression of the mature form of RSH2 and an RSH2 GFP fusion complemented ΔrelA, and mutation of the ppGpp synthase active site abolished complementation (RSH2*). In both cases the same GFP fusions were used as those in the OX:RSH2 and OX:RSH3 plant lines.
Figure 10:
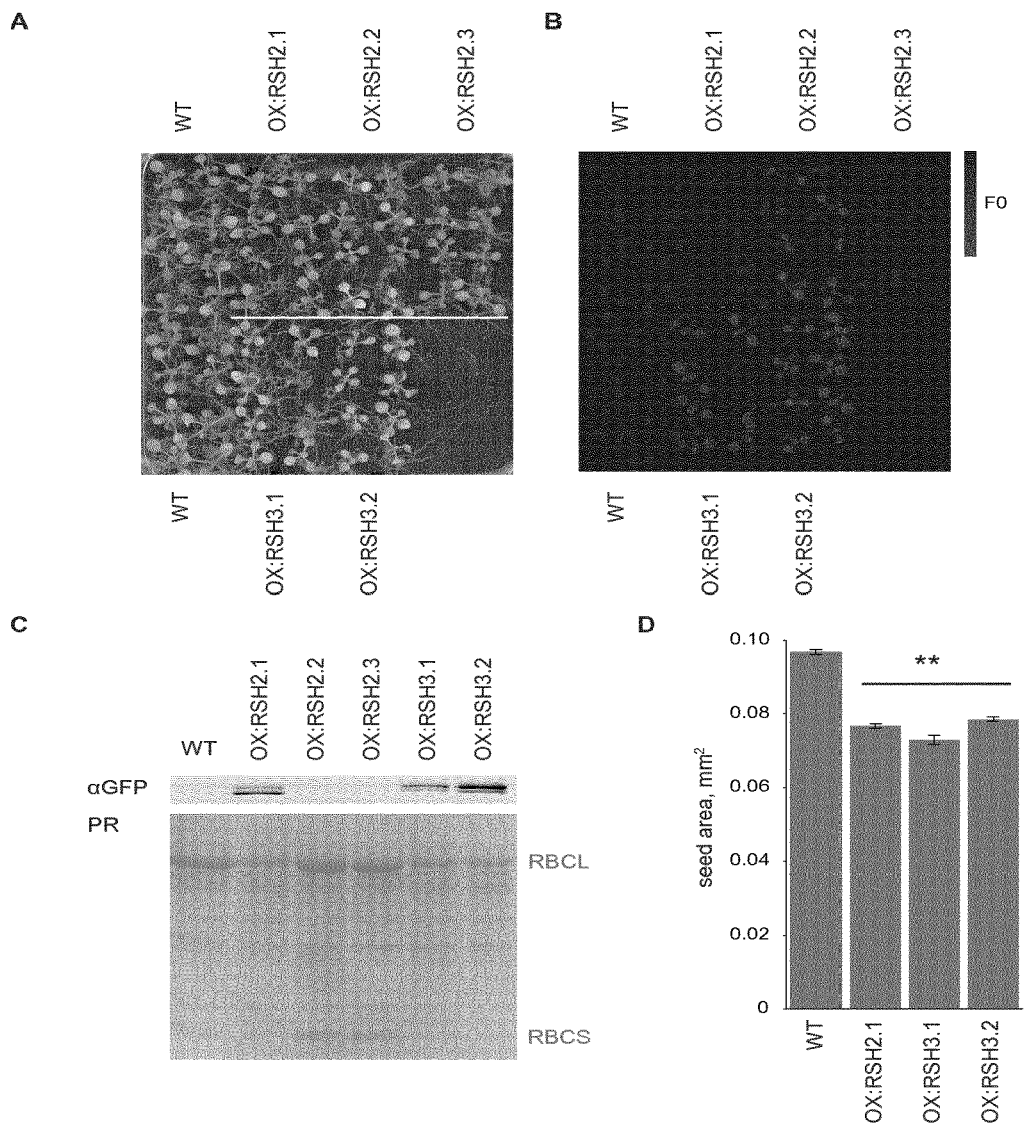
FIG. 10 represents phenotypes of different RSH2 and RSH3 overexpression lines. Wildtype seedlings and different RSH2 and RSH3 overexpression lines were grown in plates for 12 DAS and (A) photographed and (B) imaged for chlorophyll fluorescence. F0 false color scale bar, 50-350 arbitrary units. (C) Immunoblots on equal quantities of total protein extracted from the same seedlings showed that the RSH GFP fusion proteins could be detected in the lines that were small and pale, had a high F0, and a low PSII maximum quantum yield QY. Proteins were also revealed by Ponceau Red (PR). (D) RSH2 and RSH3 overexpression lines produced smaller seeds than wild type plants (**P<0.0001, Kruskal-Wallis test with post hoc Dunn test, n=254-1040). Error bars, SEM

RSH2 and RSH3 are likely to function as the major ppGpp synthases in *Arabidopsis* because they possess conserved ppGpp synthase domains, and are the most highly expressed of the RSH enzymes (Mizusawa et al., 2008) [17]. RSH2 and RSH3 also share 90% amino acid similarity and belong to the same RSH family (Atkinson et al., 2011) [8] (FIG. 8). Therefore, as a first step towards understanding the role of ppGpp in *Arabidopsis* we created plants overexpressing RSH2 and RSH3 with the addition of a C-terminal GFP tag. Because the activity of RSH enzymes can be sensitive to C-terminal tags we verified that the GFP tag did not affect ppGpp synthesis activity by complementing ppGpp deficient *E. coli* strains with the native and fusion RSH proteins (FIG. 9). The selection of transgenic plants overexpressing RSH2 and RSH3 was challenging because of the low viability of transformants obtained and the frequent loss of transgene expression in later generations. At least one stable OX:RSH2 line and two stable OX:RSH3 lines that accumulated high levels of RSH2-GFP and RSH3-GFP were isolated (FIG. 10). These plants were pale and smaller than the wildtype control, and produced small seeds that rapidly lost their ability to germinate (FIG. 1A, FIG. 10). The photosynthetic parameters of the overexpressers were determined using chlorophyll fluorescence analysis. Overexpression lines have strong basal chlorophyll fluorescence, F0 (FIG. 1A, FIG. 10) and a reduction in the maximal efficiency (or quantum yield, QY) of photosystem II (PSII): the average quantum yield was 0.86+/−0.001 SEM in wildtype plants 12 days after stratification (DAS) versus 0.690+/−0.002 in OX:RSH2.1, 0.69+/−0.006 SEM in OX:RSH3.1 and 0.73+/−0.006 in OX:RSH3.2 (n=8). During preparation of this manuscript similar phenotypes were reported for plant lines overexpressing RSH3 (Maekawa et al., 2015) [40]. Now focusing on OX:RSH3.1 plants we confirmed that chlorophyll levels are lower than in wild-type plants, and found that this is accompanied by a reduction in the chlorophyll a/b ratio (FIG. 1B). Previous work has shown that plants grown in the presence of lincomycin, an inhibitor of chloroplast translation, also have a high F0 and a low chlorophyll a/b ratio (Belgio et al., 2012) [41]. This distinctive phenotype is due to the lincomycin-mediated loss of the chloroplast-encoded reaction centre subunits from PSII (RCII), and the retention of unattached nucleus-encoded PSII light harvesting complexes (LHCII), which are rich in chlorophyll b and highly fluorescent (Belgio et al., 2012) [41]. Therefore, we suspected that RSH3 overexpression leads to a reduction of chloroplast gene expression, in a similar manner to lincomycin treatment. In agreement, there were markedly reduced amounts of the majority of the signature chloroplast-encoded proteins that we tested (FIG. 1C, in green). The greatest reduction was for PsbA, a subunit of RCII which is reduced to less than one tenth of wild-type levels. LHCB1, one of the major nuclear-encoded subunits of LHCII, remained at wild-type levels relative to total protein. The resulting >10-fold decrease in the RCII/LHCII ratio strongly suggests that a large fraction of LHCII is no longer attached to RCIIs, and explains the high F0 and low QY of OX:RSH3.1 plants. In addition to reductions in the levels of chloroplast encoded-proteins we also detected a marked reduction in the accumulation of chloroplast ribosomal RNA (rRNA) compared to cytosolic rRNA, indicating that there is a substantial drop in total chloroplast translation capacity (FIG. 1D). Reduced translation and rRNA levels are hallmarks of the bacterial response to ppGpp accumulation (Dalebroux and Swanson, 2012) [6]. We verified that the overexpression of RSH3 increases ppGpp levels using a recently developed method (FIG. 1E) (Ihara et al., 2015) [11]. To exclude the possibility that the observed phenotypes are due to other potential functions of RSH3 or indirect effects of overexpression we introduced an inducible metazoan ppGpp-specific hydrolase, MESH (Sun et al., 2010) [28], into OX:RSH3.1 plants. Expression of a chloroplast targeted MESH was able to restore wildtype F0 and chlorophyll levels to OX:RSH3.1 plants, while RSH3 overexpression was maintained (FIG. 1F, G). Expression of a catalytically inactive chloroplastic MESH (ΔMESH) or an active cytoplasmic MESH was unable to restore a wild-type phenotype (FIG. 1F, G). These findings indicate that the phenotype of OX:RSH3.1 plants is caused by the accumulation of ppGpp within the chloroplast.

Example 3: Chloroplasts in OX:RSH3 Plants are Smaller and More Numerous

Figure 2:
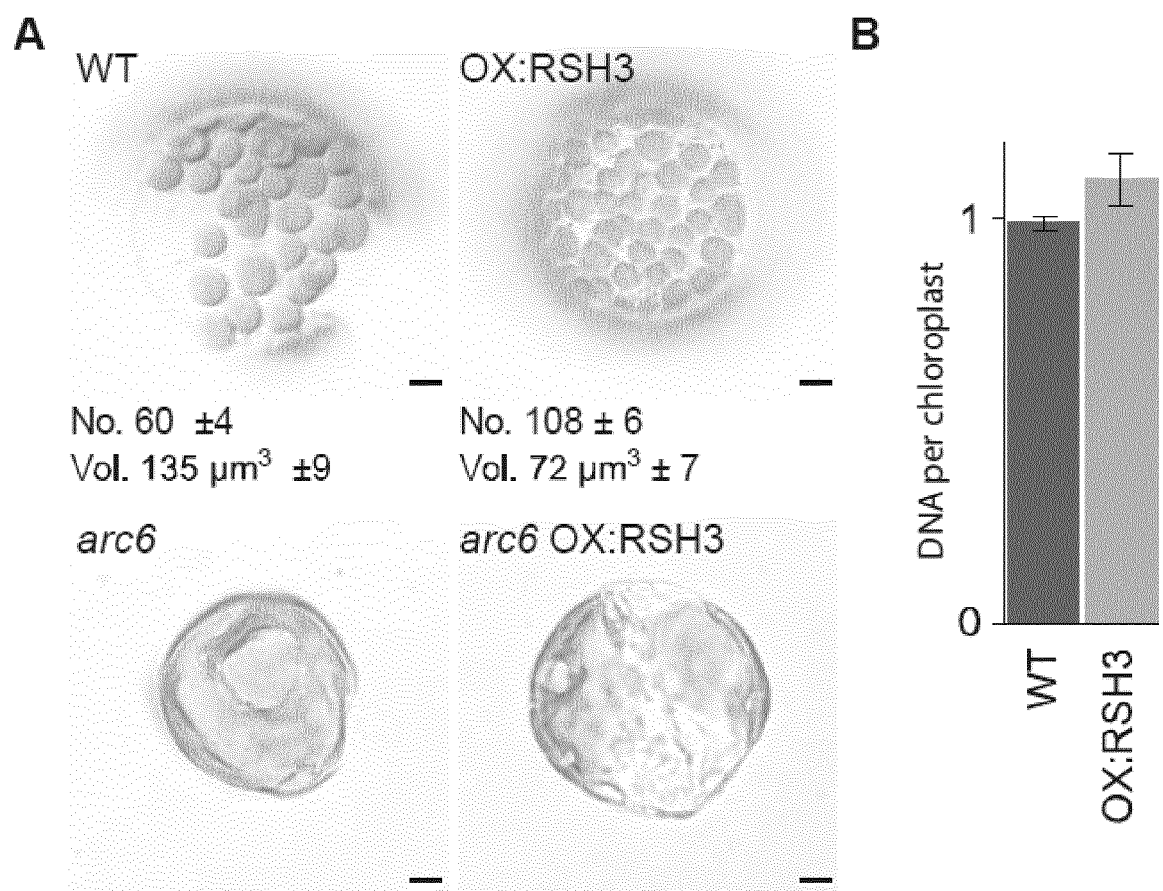
FIG. 2 represents that ppGpp accumulation in OX:RSH3.1 reduces chloroplast volume per cell without repressing chloroplast replication. Mesophyll protoplasts were isolated from soil grown WT and OX:RSH3.1 leaves 35 DAS. Representative protoplasts are shown (A). OXRSH3.1 chloroplasts were smaller than those in WT, and chloroplast number was consistently higher, even when adjusted for protoplast volume (B)(expressed as chloroplasts per 10000 µm$^3$). Despite increased numbers of chloroplasts, the percentage chloroplast volume per protoplast in OXRSH3.1 plants was significantly lower than that in WT plants. Transfer of OX:RSH3.1 into the genetic background of the chloroplast division mutant arc6 suppressed the increased chloroplast number (C). arc6 OX:RSH3.1 plants also had a significantly lower chloroplast plan area per cell than arc6 plants alone (46%±2 versus 62%±3, P<0.0001, n=13-16). (B) Chloroplast DNA content was quantified by qRT PCR on chloroplasts isolated from WT and OX:RSH3.1 plants at 24 DAS. Error bars, SEM. Significance was calculated using the Kruskal-Wallis test with the Dunn test post hoc. 255-323 chloroplasts were measured for chloroplast diameter, and 30-59 protoplasts for chloroplast number and protoplast volume in OX:RSH3.1 and WT.

Chloroplast size and number was analyzed in protoplasts from OX:RSH3.1 and WT plants (FIG. 2). We found that OX:RSH3.1 chloroplasts were significantly smaller and more numerous than WT chloroplasts (FIG. 2A, 2C). The change in chloroplast number could be suppressed by a mutation in the nuclear gene ARC6 that encodes a component of the chloroplast division machinery (FIG. 2B). DNA content per plastid was also constant, indicating that the increase in chloroplast number is due to increased chloroplast replication and division (FIG. 2D) (Robertson et al., 1995) [42]. This contrasts with the situation in bacteria where ppGpp inhibits proliferation by directly targeting the DNA primase, the enzyme that initiates DNA replication (Dalebroux and Swanson, 2012) [6]. The inability of ppGpp to inhibit DNA replication in *Arabidopsis* chloroplasts could be explained by the recent observation that plants lack bacteria-like DNA primases and that chloroplast DNA replication is instead likely to be primed by a eukaryotic TWINKLE homologue (Diray-Arce et al., 2013) [43]. Importantly we also found that, despite the increased chloroplast number, the percentage of total cell volume occupied by chloroplasts was significantly lower than that in WT plants (FIG. 2C).

Example 4: ppGpp Acts on Chloroplast Gene Expression

Figure 11:
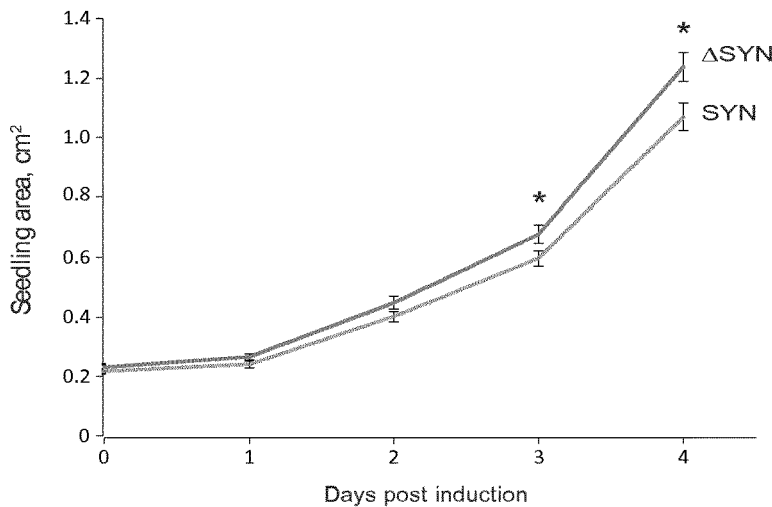
FIG. 11 represents growth of SYN and ΔSYN following induction. 12 DAS seedlings were induced by submersing in 30 μM dexamethasone for 3 minutes and then photographed each day post induction for four days. Seedling size was determined in ImageJ. *P<0.05, two-way Student test, n=30. Error bars, SEM.

The pleiotropic phenotypes of RSH2 and RSH3 overexpressing plants makes it challenging to determine how ppGpp acts within the chloroplast. In particular it is not clear to what extent the reduced chloroplast protein and RNA levels in these lines can be attributed to ppGpp rather than to the reduced total chloroplast volume per cell (FIG. 2C). Therefore we developed an inducible expression system that permits the conditional accumulation of ppGpp in phenotypically wildtype plants. For this approach we created transgenic plants harbouring a T-DNA insertion that encodes a dexamethasone-inducible ppGpp synthase domain from the *E. coli* RelA (SYN) that is targeted to the chloroplast. The truncated RelA synthase domain used has constitutive ppGpp synthase activity in *E. coli* (Schreiber et al., 1991) [23]. Induction of SYN expression by dexamethasone application led to the accumulation of high levels of ppGpp (FIG. 3A). This was accompanied by a reduction in chlorophyll levels, a reduction in the chlorophyll a/b ratio and an increase in F0 in a dose and time dependent manner (FIG. 3B-D). There was also a modest but significant repression of plant growth (FIG. 11). Inducible expression of a catalytically inactivated ppGpp synthase (ΔSYN) had no effect on these parameters, indicating that the SYN phenotypes can be attributed directly to SYN catalyzed ppGpp accumulation. The SYN phenotypes are very similar to those observed in OX:RSH3.1 plants or in plants treated with lincomycin, confirming that ppGpp causes a global suppression of chloroplast gene expression. In agreement we found a reduction in signature chloroplast-encoded proteins and chloroplast rRNAs in plants expressing SYN (FIGS. 3E and 3F). Nucleus-encoded proteins in the chloroplast and cytosolic rRNAs were not affected. Taken together these results indicate that both RSH3 and SYN overexpression cause the accumulation of ppGpp in the chloroplast, and that ppGpp accumulation can rapidly lead to reductions in the amounts of chloroplast-encoded rRNA and protein. In both cases the marked depletion in chloroplast rRNA indicates that ppGpp accumulation severely constrains chloroplast translation capacity.

Example 5: ppGpp Controls Chloroplast Gene Expression by Reducing Steady State Transcript Levels in the Chloroplast In bacteria many of the principal physiological effects of ppGpp are caused by the inhibition of transcription which can occur by at least two distinct mechanisms (Dalebroux and Swanson, 2012) [6]. In *E. coli* ppGpp directly interacts with the RNA polymerase in cooperation with the transcription factor DskA to alter promoter selection. Transcription from rRNA genes is subject to particularly strong inhibition in the presence of ppGpp. In contrast, in *Bacillus subtilis* the RNA polymerase is insensitive to ppGpp (Krasny and Gourse, 2004) [45], and ppGpp instead causes a decrease in the GTP pool by direct inhibition of GTP biosynthesis enzymes such as guanylate kinase (GK) (Kriel et al 2012) [44]. The decrease in GTP levels inhibits gene transcription, and again this effect is particularly strong for the rRNA and tRNA genes where GTP is the initiating nucleotide (Krasny and Gourse, 2004) [45]. In plants ppGpp has also been linked to the control of chloroplast transcription, although so far this has not been directly demonstrated in vivo (Yamburenko et al., 2015, Maekawa et al., 2015) [20, 40]. There is also evidence for both *E. coli*-like and *B. subtilis*-like mechanisms for the inhibition of transcription by ppGpp in plants. Despite the absence of a homologue of DskA, in vitro studies on chloroplast extracts have shown that ppGpp specifically binds to and inhibits the bacterial-like polymerase encoded by the chloroplast genome (Plastid Encoded Polymerase, PEP) (Sato et al., 2009, Takahashi et al., 2004) [12, 10]. However the 50% inhibitory concentrations (1050) are rather high (1 mM, Sato et al. (2009) [12]; 2 mM Takahashi et al. (2004) [10]. Chloroplasts also contain an alternative Nucleus-Encoded Polymerase (NEP), which plays a minor role in green tissues, and which is not inhibited by ppGpp. A recent study also provides support for a *B. subtilis* like mechanism by showing that recombinant chloroplastic GK enzymes from rice and *Arabidopsis* are as sensitive to inhibition by ppGpp in vitro as the *Bacillus subtilis* GK with IC50s of around 30 µM (Nomura et al., 2014) [14].

Figure 3:
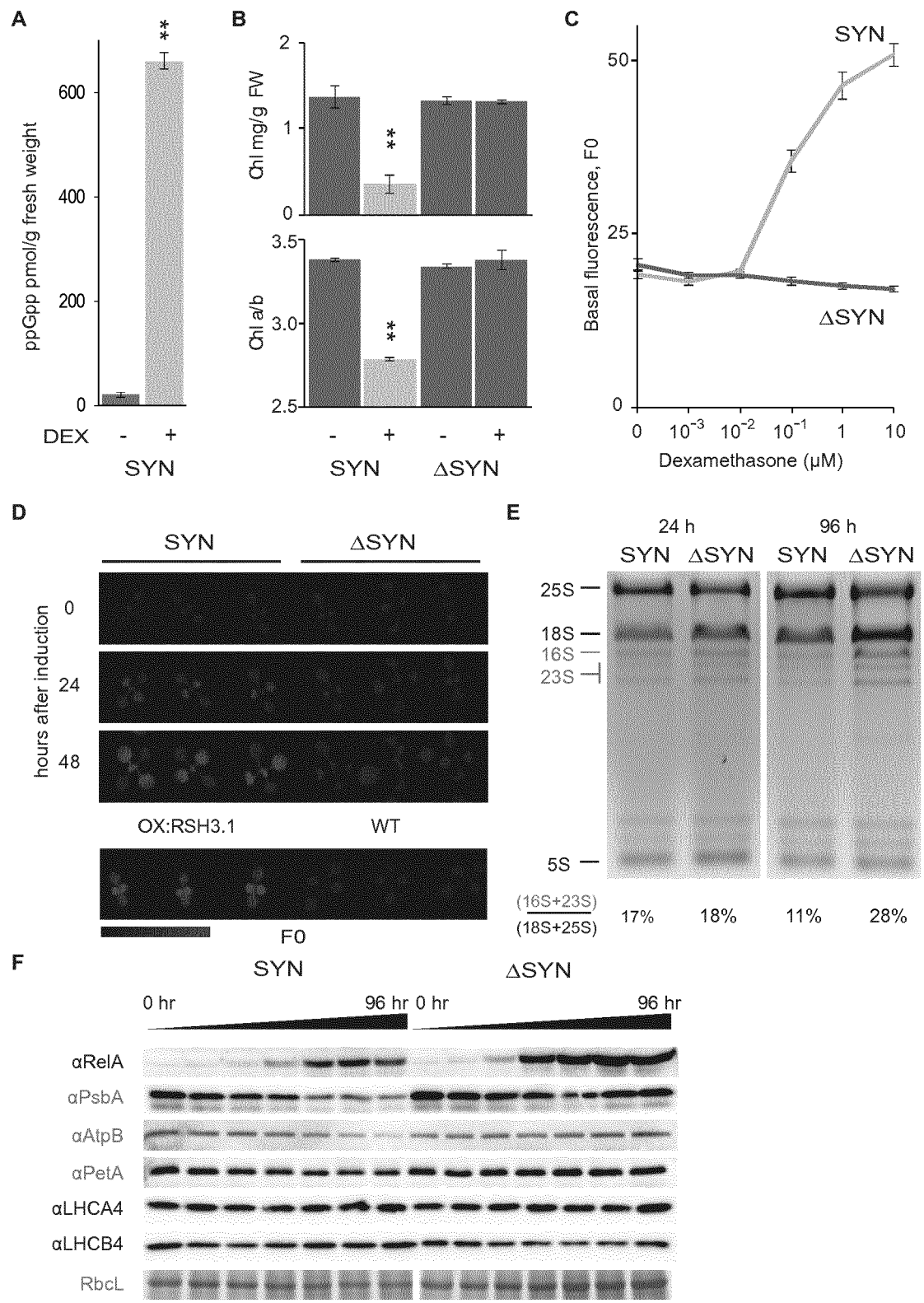
FIG. 3 represents that conditional expression of a bacterial ppGpp synthase (SYN) reduces chloroplast function. SYN plants contain a transgene encoding a chloroplast-targeted ppGpp synthase from bacteria that is under the control of an inducible promoter. ΔSYN plants contain a transgene encoding a catalytically inactive variant of SYN. (A) SYN induction results in a large increase in ppGpp levels, P=0.000003, n=3. ppGpp was extracted and quantified 72 hours after induction of SYN plants grown on plates for 12 DAS by submersing with either the carrier (DMSO) or 30 µM dexamethasone (DEX) for 3 minutes. SYN and ΔSYN seedlings were analyzed for (B) chlorophyll content and chlorophyll a/b ratios 4 days after induction with dexamethasone, **P<0.001 versus DMSO control (n=4), and (C) F0 after 8 days growth on plates containing different concentrations of dexamethasone (n=18). After induction of SYN and ΔSYN plants 12 DAS changes in (D) F0 (F0 false color scale bar, 50-350 units), (E) rRNA and (F) chloroplast proteins were followed. Chloroplast proteins were detected by immunoblot on equal quantities of protein using the indicated antibodies. Anti-RelA detects the SYN and ΔSYN proteins. Samples were taken at 0, 2, 4, 8, 24, 48, 96 hours after induction. RbcL was revealed by Coomassie Brilliant Blue staining. Chloroplast-encoded proteins and rRNAs are in green. Significance was calculated using the two-way Student t-test. Error bars, SEM.
Figure 4:
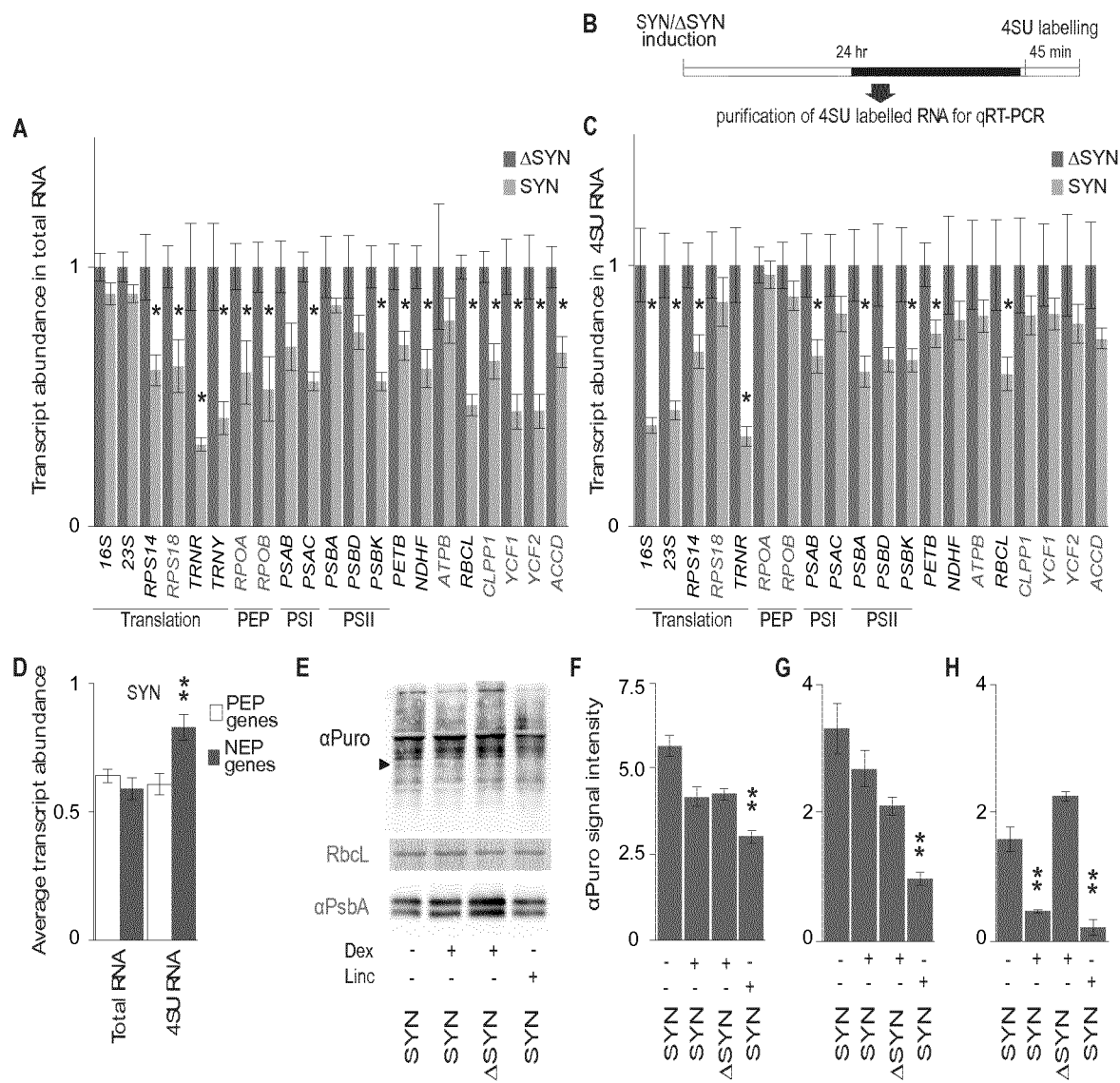
FIG. 4 represents that ppGpp accumulation reduces chloroplast transcript levels but does not have a major direct effect on chloroplast translation. (A) qRT PCR for selected chloroplast-encoded transcripts 24 hrs after the induction of ΔSYN and SYN seedlings grown on plates for 12 DAS as above. Transcripts produced only or significantly by NEP in green tissue (NEP genes) are indicated in purple, *P<0.05 SYN versus ΔSYN for a single transcript, n=4. Transcript abundance was normalized to the nuclear-encoded 18S, APT1, PP2A and ULP7 reference transcripts. The transcription rates of chloroplast genes in induced SYN and ΔSYN plants were measured by labeling new transcripts with 4SU in vivo (B) and quantifying the abundance of purified 4SU transcripts by qRT-PCR (C). Transcript abundance was normalized to 18S, PP2A and ULP7 reference genes. The induction of SYN had significantly less effect on the transcription of NEP genes than it did on PEP genes (D), P=0.0011, ANOVA with post hoc Dunnett test, n=8-11. 24 hrs after induction of SYN and ΔSYN seedlings translation rates were also analyzed by quantifying the incorporation of puromycin into nascent proteins during 1 hour. Puromycin incorporation was assessed by immunoblot analysis on equal quantities of total chloroplast proteins (10 µg) using an antibody against puromycin (E). Plants treated with lincomycin for 24 hrs were used as a control. The black arrow indicates PsbA. RbcL is a loading and transfer control, and is shown by Ponceau red staining on the same membrane used for puromycin detection. Incorporation was quantified across five experimental replicates (F). Lincomycin treated SYN plants showed a significant drop in puromycin incorporation compared to induced SYN plants, P<0.01. No significant difference could be detected in the incorporation of puromycin between induced SYN and ΔSYN plants. Puromycin incorporation into PsbA was also quantified at (G) 24 hours and (H) 72 hours after treatment, P<0.01 versus ΔSYN, n=4. Samples were normalized to total chloroplast protein. Unless stated otherwise significance was calculated using the two-way Student t-test. Error bars, SEM.
Figure 12:
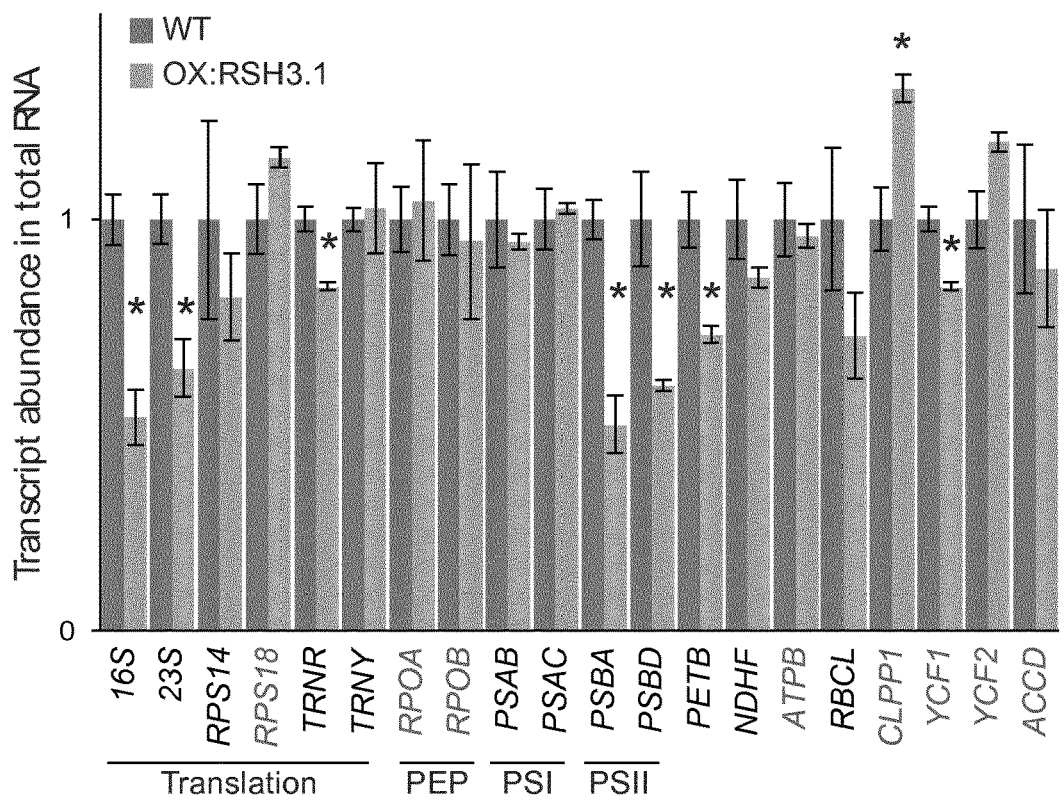
FIG. 12 represents qRT PCR analysis of OX:RSH3.1 plants. qRT PCR for chloroplast transcripts in wildtype (dark green) and OX:RSH3 seedlings (light green) 12 DAS (n=4, normalized to 18S, APT1, PP2A and ULP7 reference transcripts). Transcripts produced principally or partially by NEP are indicated in purple. *P<0.05, two-way Student test. Error bars, SEM.

To assess the role of ppGpp on chloroplast transcription we therefore quantified the steady-state levels of a broad range of chloroplast transcripts at 24 hours after induction of SYN (FIG. 4A). This is an early timepoint when we detect only a small change in F0 and no change in rRNA levels (FIG. 3D, E). Strongly supporting a role for ppGpp in directly regulating plastid transcript accumulation in vivo we observed a significant reduction in the steady-state levels of a broad range of chloroplast transcripts. Interestingly, transcript levels were also reduced for genes that are thought to be exclusively or significantly transcribed by NEP in green tissues such as RPS18, RPOA, RPOB, PETB, YCF1, YCF2 and ACCD (Borner et al., 2015) [46]. In OX:RSH3.1 plants, where ppGpp levels are somewhat lower and at equilibrium, there was also a significant reduction in the accumulation of chloroplast transcripts (FIG. 12). However, in contrast to the situation in induced SYN plants the reduction in transcript accumulation was limited to a subset of PEP dependent genes, and NEP dependent genes were not significantly affected. This may suggest that ppGpp levels are not sufficient for the effects seen in SYN plants, or that constitutive accumulation of ppGpp can lead to the activation of compensatory mechanisms.

Steady-state transcript levels are a function of the transcription and degradation rate. To test whether ppGpp specifically downregulates transcription under in vivo conditions we used a metabolic labelling strategy with the base analogue 4-thio uridine (4SU). Efficient and non-toxic labeling of total RNA, including plastid RNA, was recently demonstrated using this approach in *Arabidopsis* (Sidaway-Lee et al., 2014) [47]. We labelled newly synthesized RNA 24 hours after SYN and ΔSYN induction. Labeled RNA was then isolated and the quantity of newly synthesized chloroplast transcripts from SYN and ΔSYN plants was analyzed by qRT-PCR using nucleus-encoded reference genes (FIG. 4B). Consistent with ppGpp-mediated transcriptional downregulation we found that the quantity of newly synthesized RNA was significantly lower in SYN plants for the majority of those genes that are principally transcribed by PEP (FIG. 4C). In contrast, we found that SYN induction had significantly less effect on the transcription of genes that are principally transcribed by NEP (FIG. 4D). This would suggest that the accumulation of certain transcripts may also be regulated post-transcriptionally. Similar differential regulation of the turnover for PEP and NEP derived transcripts has also been observed in maize (Cahoon et al., 2004) [48]. In a manner strikingly reminiscent to bacteria, the effect of ppGpp was strongest on the transcription of the chloroplast rRNAs (16S and 23S) and the arginine tRNA (TRNR). The very slight reduction in steady state levels of chloroplast rRNA 24 hours after induction can be explained by its high stability, and we indeed do see a large drop in steady state levels after 96 hrs (FIG. 3E) (Rapp et al., 1992) [49]. While we demonstrate that ppGpp is directly involved in the inhibition of plastidial transcription, our data do not allow us to clearly discern whether this is PEP-dependent or not. However, using previous estimates of stroma volume in spinach chloroplasts we calculate that stromal ppGpp concentrations in induced SYN plants can reach up to about 30 µM (Gerhardt et al., 1987) [50]. This is more than an order of magnitude lower than inhibitory concentrations obtained for PEP in vitro. GK on the other hand is likely to be significantly inhibited at these concentrations, favouring the idea that a *B. subtilis* like mechanism may inhibit transcription. Notably, GTP is the initiating nucleotide for the principal P1 and minor PC promoters of the chloroplast rRNA operon containing the 16S and 23S rRNAs in *Arabidopsis* and this phenomenon is widespread in other plants including the monocots (Suzuki et al., 2003, Swiatecka-Hagenbruch et al., 2007) [51, 52].

Figure 13:
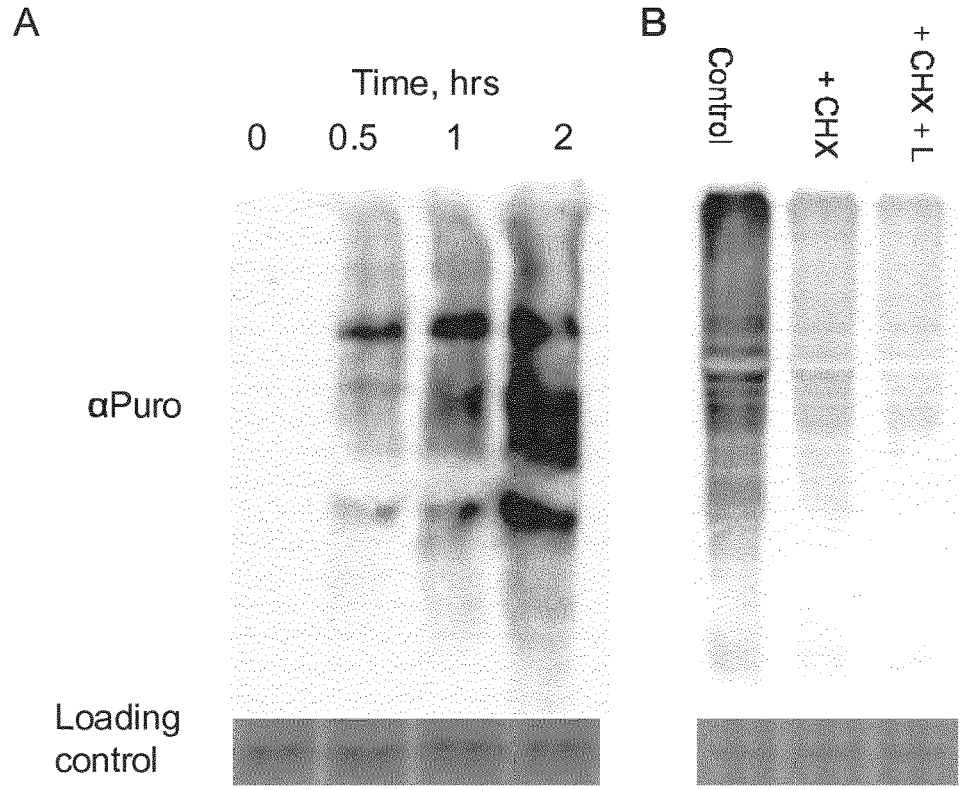
FIG. 13 represents proof of concept for puromycin labeling in plants. Puromycin is incorporated into cytosolic and chloroplastic proteins in a time dependent manner, and is inhibited by translation inhibitors. (A) Immunoblots of total *Arabidopsis* seedling proteins using a monoclonal anti-puromycin antibody (αPuro). 12-day old *Arabidopsis* seedlings were labeled with 50 μg/ml puromycin for the indicated time intervals before extraction of proteins, and equal quantities of protein were separated by SDS PAGE. Note the absence of a background signal in the unlabeled sample (0 hrs). (B) Immunoblots of equal quantities of chloroplast total protein from 12 day old seedlings labelled with puromycin for 1 hr. Incorporation of puromycin is inhibited by the pretreatment with the cytosolic translation inhibitor cycloheximide (CHX, 100 μg/ml) and is further inhibited by the chloroplast translation inhibitor lincomycin (L, 1 mM). Note that although cycloheximide blocks cytosolic translation, it also introduces a significant background signal that is caused by the puromycylation of cycloheximide arrested nascent peptide chains (David et al., 2012) [69]. This background is visible in the sample from seedlings treated with cycloheximide and lincomycin. Loading and transfer controls are RBCL stained with Ponceau red.

Example 6: ppGpp Accumulation does not have a Rapid and Direct Effect on Chloroplast Translation In bacteria ppGpp directly inhibits translation through interaction with translation initiation and elongation factors (Dalebroux and Swanson, 2012) [6]. Chloroplasts contain a bacterial-like translation machinery, and ppGpp has also been shown to inhibit chloroplast translation in in vitro assays (Nomura et al., 2012) [13]. We therefore tested whether ppGpp directly represses chloroplast translation in vivo in SYN plants. Despite the inhibition of transcription by ppGpp there is only a small reduction in rRNA levels 24 hours after SYN induction, and thus a near wild type translational capacity should be present (FIGS. 3E and 4A). Therefore, total chloroplast translational rates were quantified 24 hours after induction using metabolic labeling with puromycin, an aminoacyl transfer RNA analog that can be incorporated into nascent polypeptide chains (Schmidt et al., 2009) [53]. We were first able to show that puromycin is taken up by plants in a time dependent manner and is efficiently incorporated into nascent cytosolic and chloroplastic proteins (FIG. 13). Next we analyzed total chloroplast translation rates in plants expressing SYN and ΔSYN (FIG. 4E-F). No significant reduction in total chloroplast translation could be observed in plants expressing SYN at 24 hours after induction compared to plants expressing ΔSYN (FIG. 4E-F). However, chloroplast translation was significantly reduced by the application of the translation inhibitor lincomycin. The PSII RC subunit was an even more sensitive reporter of translation probably due to its high turnover rates (FIG. 4G-H). PsbA translation was similar in induced SYN and ΔSYN plants at 24 hrs after induction, and then dropped sharply only in induced SYN plants after 72 hrs.

The effect of lincomycin on PsbA translation was strong at both 24 hrs and 72 hrs after treatment. These results show that ppGpp accumulation does not have a large direct effect on chloroplast translation under our conditions. This could be explained by a lower sensitivity of the translational machinery to ppGpp, a possibility that is supported by the existing in vitro data that suggests an 1050 of >400 µM (Nomura et al., 2012) [13].

Example 7: RSH Mutants have Altered Chlorophyll Fluorescence and ppGpp Levels

We next sought to understand the role of RSH enzymes in controlling ppGpp levels in planta, and their function during plant growth and development. The four *Arabidopsis* RSH proteins (RSH1, RSH2, RSH3 and CRSH) are likely to be the principal mediators of ppGpp homeostasis because they possess well known ppGpp synthase and hydrolase domains (FIG. 8), and because RSH2, RSH3 and CRSH show ppGpp biosynthetic activity in *E. coli* assays (Mizusawa et al., 2008, Masuda et al., 2008) [17, 18]. We also show here that RSH2 and RSH3 overexpression results in ppGpp accumulation in planta (FIG. 1E), and a recent study also confirms these findings for RSH3 (Maekawa et al., 2015) [40].

We therefore isolated single insertion mutants for each RSH1, RSH2, RSH3 and CRSH (referred to here as rsh1-1, rsh2-1, rsh3-1 and crsh-1) (FIG. 14A). The TDNA insertions in rsh1-1, rsh2-1 and rsh3-1 are upstream of the regions encoding the ppGpp metabolizing domains and result in a complete loss of mature mRNA. We could also detect no or little ectopic transcription in the regions downstream of the TDNA insertions (FIG. 14B). The TDNA insertion in crsh-1 is downstream of the regions encoding the ppGpp metabolizing domains, and there is only a partial reduction in mature CRSH transcript levels. Therefore we used an artificial micro RNA (amiRNA) to knock down CRSH expression to very low levels (crsh-ami, FIG. 14C). No clear visible phenotypes could be observed in rsh1-1, rsh2-1, rsh3-1, crsh-1 and crsh-ami. In particular, we did not observe any altered flower development or fertility defects for crsh-ami despite a previous study showing altered flower development and reduced fertility in a transgenic line where CRSH was silenced by co-suppression (Masuda et al., 2008) [18]. This difference in results may be explained by different levels of CRSH silencing, or by the presence of a linked mutation or off-target silencing that reduced fertility in the original CRSH co-suppression line. Furthermore, overexpression of the RSH1 ppGpp hydrolase or induction of the MESH ppGpp hydrolase before and throughout flowering did not cause any detectable changes in flower development or fertilization. Thus it is not currently clear whether CRSH regulates fertilization by modulating ppGpp levels. Due to likely redundancy for ppGpp biosynthesis the RSH single mutants were crossed to make all the double mutant (DM) and triple mutant (TM) combinations as well as the quadruple mutants (QM for rsh1-1 rsh2-1 rsh3-1 crsh-1, and QMai and QMaii for rsh1-1 rsh2-1 rsh3-1 with independent crsh-ami insertions).

Figure 1:
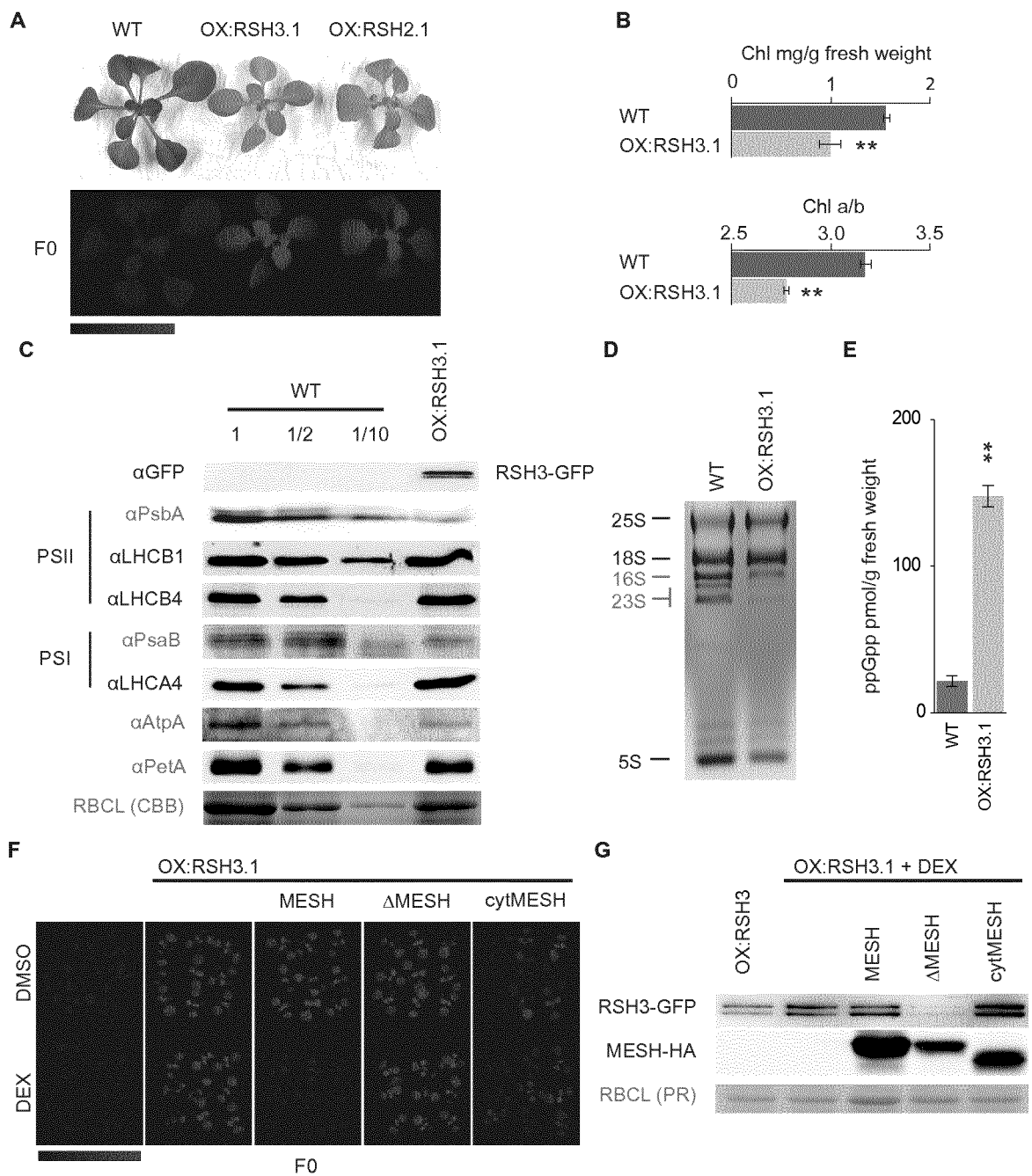
FIG. 1 represents that RSH3 overexpression reduces chloroplast function. (A) Plants overexpressing RSH3 (OX:RSH3.1) and RSH2 (OX:RSH2.1) are small and pale (above), and have a high basal chlorophyll fluorescence, F0 (below). Plants shown were grown on plates for 16 days after stratification (DAS). F0 false color scale bar, 50-350 units. (B) The leaves of OX:RSH3.1 plants have significantly lower chlorophyll levels and chlorophyll a/b ratios than the wildtype (n=4, 12 DAS). (C) Immunoblots on equal quantities or dilutions of total protein from wildtype and OX:RSH3.1 seedlings 12 DAS using the indicated antibodies against signature chloroplast proteins. Chloroplast-encoded proteins are indicated by green text. CBB, Coomassie Brilliant Blue. (D) Total RNA from wildtype and OX:RSH3.1 plants showing cytosolic (black) and chloroplastic rRNA (green). (E) ppGpp was extracted from the leaves of soil grown plants 32 DAS and quantified by ultra performance liquid chromatography-mass spectrometry (UPLC-MS), P=0.00013, n=3. (F) The F0 in wildtype plants, OX:RSH3.1 plants and OX:RSH3.1 plants crossed with inducible MESH plants 12 DAS. Plants were grown on media containing the carrier (DMSO) or 1 µM dexamethasone (DEX). MESH, catalytically active chloroplastic enzyme; ΔMESH, catalytically inactive chloroplastic enzyme; and cytMESH, an active MESH targeted to the cytoplasm. cytMESH plants were segregating for OX:RSH3.1. (G) Immunoblots showing the accumulation of RSH3 and MESH proteins in total extracts from the same plants as analyzed for F0 in (F). For cytMESH only plants overexpressing RSH3 were selected for protein extraction. PR, Ponceau Red. Significance was tested using the two-way student t-test, **P<0.01. Error bars, SEM.
Figure 5:
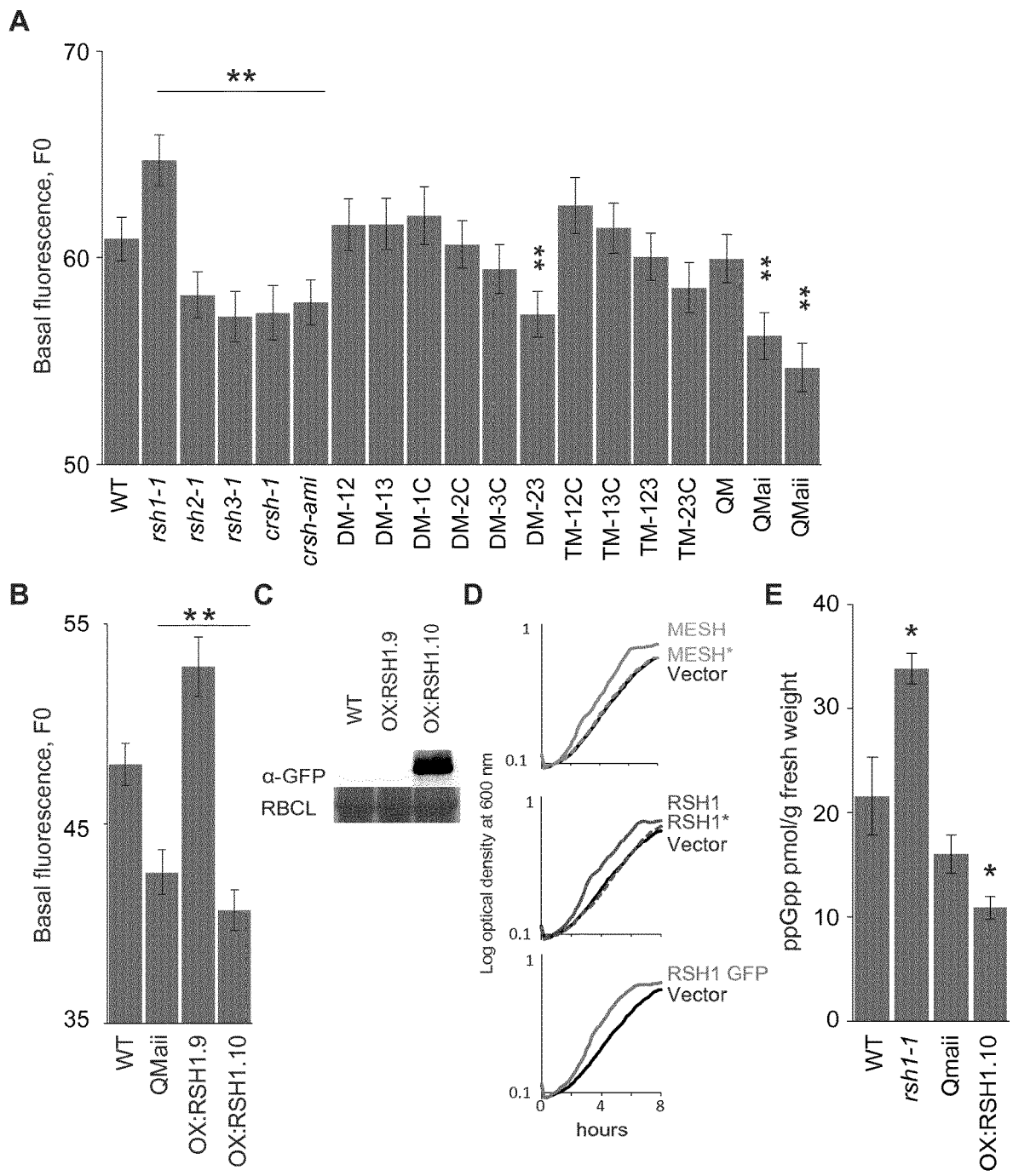
FIG. 5 represents that RSH enzymes mediate ppGpp equilibrium during vegetative growth. (A) Basal chlorophyll fluorescence (F0) was measured in the seedlings of a panel of 18 RSH mutants grown on plates for 12 DAS. crsh-ami, plants where CRSH is silenced by an artificial microRNA; DM-xy, double mutant for RSHx and RSHy; TM-xyz, triple mutant for RSHx, RSHy and RSHz; QM, quadruple mutant with crsh-1 mutation; QMai and QMaii, quadruple mutants where CRSH is silenced by independent crsh-ami alleles. The F0 phenotype of selected mutants was reconfirmed multiple times with similar results. OX:RSH1 plants were analyzed for (B) F0 and (C) RSH1-GFP protein accumulation by immunoblotting. The ppGpp hydrolase activity of different RSH enzymes was tested by expression in a slow-growing $E.$ $coli$ strain that overaccumulates ppGpp. (D) Bacterial growth curves were obtained by measuring optical density every 10 minutes over 8 hrs (average of four experimental replicates). The expression of the ppGpp hydrolase MESH resulted in a significant acceleration of growth (doubling time, TD 1.84 hrs±0.003 SEM for MESH versus 2.33 hrs±0.04 SEM for the vector only control, P<0.0001, two-way Student t-test). RSH1 and RSH1-GFP also significantly accelerated growth of the mutant indicating that they also act as ppGpp hydrolases (RSH1 TD 1.79 hrs±0.013 SEM, RSH1-GFP TD 1.67 hrs±0.011 SEM, P<0.0001 versus vector only control, two-way Student t-test). Mutation of the ppGpp hydrolase domains (MESH* and RSH1*) restored a slow growth phenotype indistinguishable from that of the vector only control. CRSH showed no activity in the same test, and RSH2 and RSH3 transformants could not be obtained to test, presumably due to overproduction of ppGpp. (E) Quantification of ppGpp in different mutant lines. ppGpp was extracted from the leaves of soil grown plants 35 DAS and quantified UPLC-MS, *P<0.05, two-way Student t-test, n=3. Large scale extractions confirmed that ppGpp levels were significantly lower in than the WT in QMaii and OX:RSH1.10 (FIG. 15). Unless stated otherwise data were analyzed by ANOVA with post hoc Dunnett tests versus the wild-type controls, *P<0.05, **P<0.01. For F0 tests n=60-72 individual plants. Error bars, SEM.

We reasoned that alterations in the ppGpp levels in the different RSH mutants could affect the stoichiometry of PSII in a manner that would be detectable as changes in chlorophyll fluorescence, F0, as we observed in OX:RSH2, OX:RSH3 and SYN plants (FIG. 1-2). We therefore measured the F0 in each of the 18 RSH mutants (FIG. 5A). Strikingly, we discovered that the single mutants for genes encoding the ppGpp biosynthetic enzymes RSH2, RSH3 and CRSH have a significantly lower F0 than the wildtype control, and that this effect increased when the mutations were combined in the quadruple mutants (QMai and QMaii). A low F0 is consistent with low ppGpp levels: a reduction in ppGpp would be expected to derepress plastid gene expression and thus increase the proportion of chloroplast-encoded PSII RC subunits relative to nucleus-encoded LHCII. Higher proportions of PSII RC are known to increase the efficiency of excitation transfer to photochemistry, and therefore to directly diminish the proportion of excitation energy that is released as fluorescence (Engelmann et al., 2005) [54]. Interestingly, we found that rsh1-1 has a higher F0 than the wildtype, a similar phenotype to SYN and OX:RSH3 plants that over-accumulate ppGpp. RSH1 lacks a functional ppGpp synthase domain and has a conserved ppGpp hydrolase domain, although ppGpp hydrolysis activity has not previously been demonstrated (FIG. 8) (Mizusawa et al., 2008) [17]. The fluorescence data therefore supports the idea that RSH1 may act as a ppGpp hydrolase, and that loss of RSH1 in rsh1-1 results in greater ppGpp accumulation and the consequent repression of PSII RC expression. Critically, and as would be expected for a mutation in a ppGpp hydrolase, the rsh1-1 mutant phenotype is epistatic to mutations in the ppGpp synthases. Mutations in RSH2, RSH3 and CRSH are sufficient to completely suppress rsh1-1 in QMai and QMaii (FIG. 5A). These fluorescence experiments were repeated multiple times and we found that F0 is a robust readout for the presumed action of ppGpp in the chloroplast under physiological conditions. F0 measurements on OX:RSH1 plants provide additional evidence that RSH1 acts as a ppGpp hydrolase. OX:RSH1.10, an overexpression line that accumulates high levels of RSH1-GFP, has a significantly lower F0 than the wildtype control (FIG. 5B). In contrast OX:RSH1.9, a line where expression of RSH1 appears to be silenced by co-suppression, has a higher F0 (FIG. 5B, C). To provide evidence that is completely independent of chlorophyll fluorescence measurements we also tested the hydrolase functions of RSH enzymes by expression in a slow growing *E. coli* mutant that over accumulates ppGpp (FIG. 5D) (My et al., 2013) [39]. The known ppGpp hydrolase MESH1 was capable of rescuing the slow growth phenotype. Expression of RSH1 was also able to rescue the mutant, demonstrating that RSH1 can indeed function as a ppGpp hydrolase. Furthermore, expression of the same RSH1-GFP fusion protein as that expressed in OX:RSH1.10 plants demonstrated that this protein was also capable of rescuing the slow growth phenotype of the *E. coli* mutant.

Figure 15:
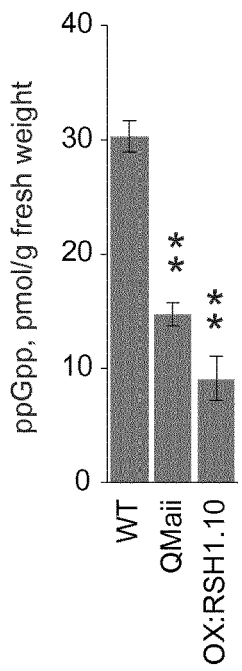
FIG. 15 represents that ppGpp levels in QMaii and OX:RSH1.10 were determined using a large scale extraction. ppGpp was extracted from the leaves of plants grown on plates for 12 DAS and quantified by UPLC-MS, **P<0.01, two-way Student t-test versus WT, n=4 experimental replicates.

We next sought to confirm our evidence for altered ppGpp levels by direct measurements of ppGpp. In agreement with our data a significant increase in ppGpp could be detected for rsh1-1, and a significant decrease in ppGpp could be detected for OX:RSH1.10 (FIG. 5E). Lower levels were also detected in QMaii, although the significance was borderline. However, by scaling up the extraction procedure by a factor of five and analyzing more concentrated extracts we could confirm that ppGpp levels were indeed significantly lower than the WT in both QMaii and OX:RSH1.10 (FIG. 15). Together these results indicate that RSH1 is antagonistic to RSH2 and RSH3, and that together the RSH enzymes appear to maintain ppGpp levels in equilibrium. Other enzymes may also be involved in maintaining this equilibrium, and indeed the absence of a run-away increase in ppGpp levels in rsh1-1 plants may be due to the presence of specific hydrolases such as the moiety X (Nudix) phosphohydrolase NUDX26 (Ito et al., 2012) [55].

Figure 6:
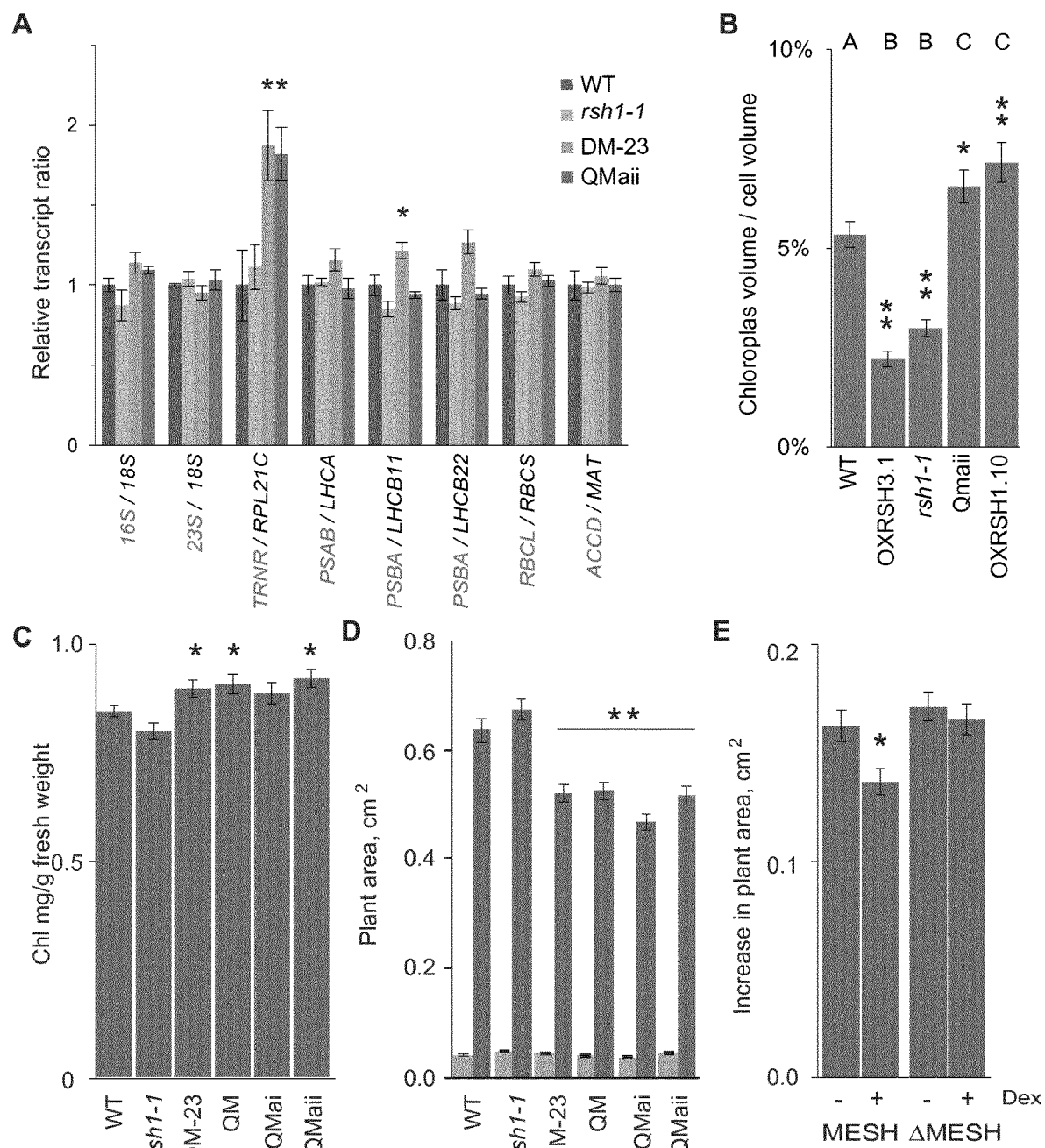
FIG. 6 represents that RSH enzymes are required for regulating chloroplast function, volume and plant growth. (A) Ratios of chloroplast (green) to nuclear encoded (black) transcripts in different RSH mutants. qRT PCR for was performed on cDNA extracted from seedlings grown on plates for 12 DAS. Significance was calculated using ANOVA with post hoc Dunnett tests versus the wild-type controls, n=5 experimental replicates. (B) Total chloroplast volume per cell was calculated in protoplasts isolated from fully expanded leaves of plants grown on soil at 39 DAS. Representative protoplast images are shown in FIG. 16B. Statistical significance was calculated using Kruskal-Wallis with the Dunn test post hoc, and the resulting groups are indicated above each bar. 30 protoplasts were analyzed for OX:RSH3.1 and 47-59 for the other lines. Similar results were also obtained using an independent approach on intact cells (FIG. 16C). (C) Chlorophyll levels were measured in selected RSH mutants grown on soil at 24 DAS. DM-23 and the QMs have a higher chlorophyll content than the wild-type, two-way Student's t-test, n=8 plants. (D) Plant surface area for wild type and mutant seedlings grown on plates at 6 (light green) and 12 days (dark green) after stratification. Except for rsh1-1, which was larger (P<0.0001), there were no significant differences between the mutants and wildtype at 6 DAS. Similar results were also obtained for plants grown in soil (FIG. 16D). Significance was calculated using ANOVA with post hoc Dunnett tests versus the wild-type controls, n=50 plants per line. (E) At 8 DAS MESH and ΔMESH plants were transferred onto media containing DMSO (control) or 1 µM dexamethasone (induced) and the increase in plant area was measured 4 days after transfer. The two-way Student t-test was used to compare non-induced and induced plants, n=36 plants.*P<0.05, **P<0.01, error bars, SEM.
Figure 16:
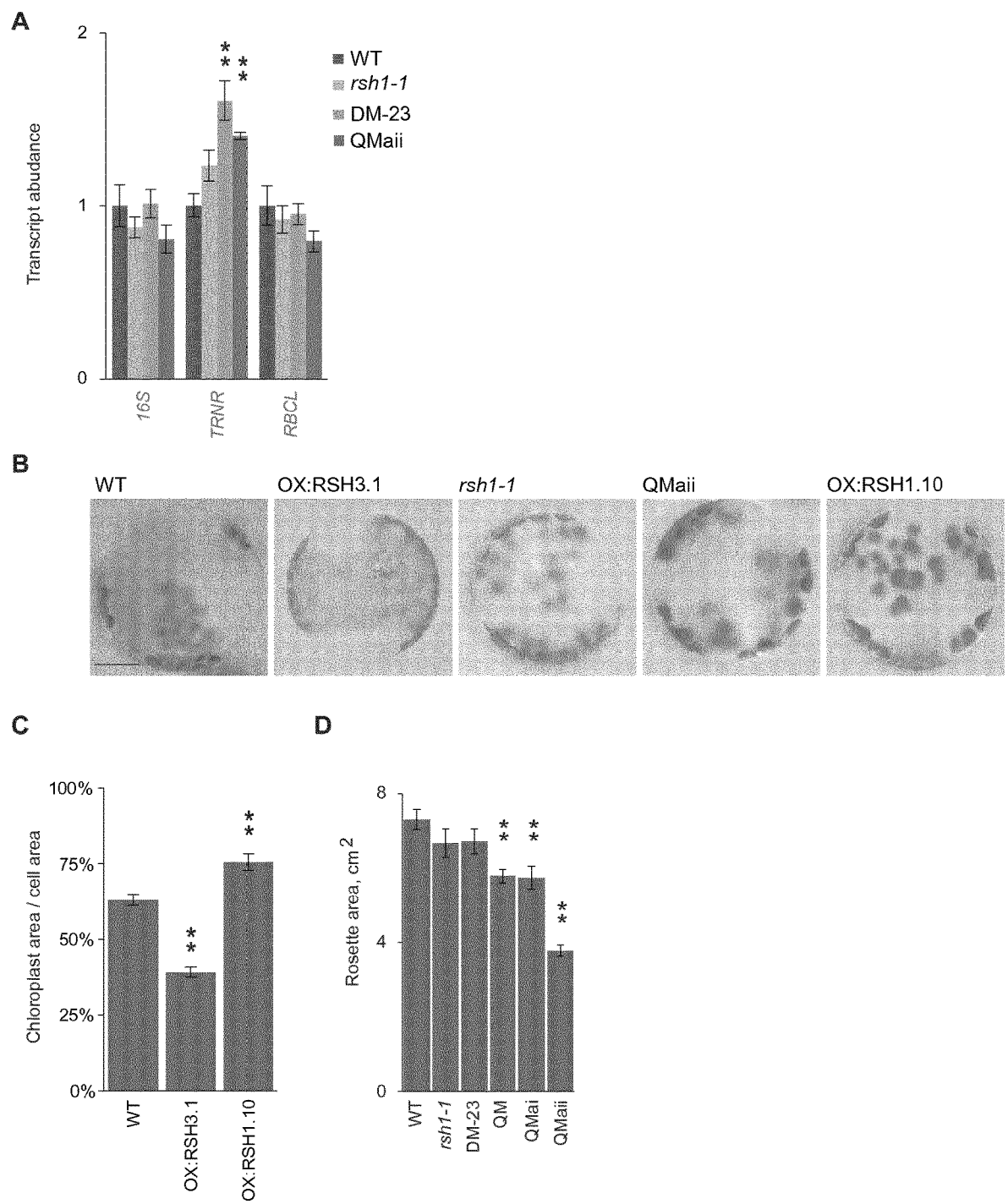
FIG. 16 represents phenotypes of RSH mutants during vegetative growth. (A) qRT PCR for chloroplast transcripts in wildtype and mutant plants 12 DAS. Data were analyzed by ANOVA with post hoc Dunnett tests versus the wildtype control, n=5. Expression was normalized to 18S, APT1, PP2A and ULP7 reference transcripts. (B) Images of representative protoplasts from fully expanded leaves of plants grown on soil at 35 DAS (scale bar, 20 μm). Analysis of these protoplast populations is presented in FIG. 6B. (C) Chloroplast plan area per cell area was analyzed in intact cells 28 DAS as described previously (Pyke and Leech, 1991) [36]. Data were analyzed by the Kruskal-Wallis test with the Dunn test post hoc. (D) The average rosette area for selected mutants after 24 days growth on soil under long day conditions. Data were analyzed by ANOVA with post hoc Dunnett tests versus the wildtype controls, n=16 plants; **P<0.01; error bars, SEM.

Example 8: Chloroplast Function and Vegetative Growth are Affected in RSH Mutants As we show above that, in addition to perturbing the stoichiometry of PSII, ectopic ppGpp accumulation inhibits chloroplast gene expression by reducing steady state levels of chloroplast transcripts, and reduces chloroplast size (FIGS. 1-3). If ppGpp acts on chloroplast transcription during vegetative growth we might expect to see alterations in the ratio between chloroplast-encoded and nuclear-encoded transcripts for chloroplast complexes and pathways in plants with lower ppGpp levels. We therefore quantified the expression ratios for a range of such transcript pairs including those for chloroplast and cytosolic ribosomal RNA (16S/18S, 23S/18S), the arginine tRNA TRNR and RPL21C that encodes a subunit of the chloroplast ribosome, transcripts encoding the RC and LHC subunits of PSI and PSII (PSAB/LHCA1, PSBA/LHCB11, and PSBA/LHCB22), transcripts encoding the small and large subunits of RuBisCO (RBCL/RBCS), and transcripts encoding the acetyl-CoA carboxylase β subunit and malonyl/acetyltransferase of fatty acid biosynthesis (ACCD/MAT) (FIG. 6A). Consistent with the idea that ppGpp regulates chloroplast transcription during vegetative growth we found evidence for significant increases in the TRNR/RPL21C and PSBA/LHCB11 ratios for lines with lower ppGpp levels (DM-23 and QMaii). The increase in TRNR was robust as it could also be observed when normalized against nuclear-encoded reference genes (FIG. 16A). Interestingly TRNR was also the most affected transcript in SYN lines at the steady-state and transcription levels (FIG. 4A, B). The absence of detectable changes for the remaining genes suggests that the altered ppGpp levels in the RSH mutants may cause effects that are too small for quantification by qRT PCR (<25%), or alternatively that feedback mechanisms might regulate nuclear gene expression to maintain an expression ratio at close to WT levels.

We next examined chloroplast size and number in protoplasts isolated from different RSH mutants and overexpression lines (FIG. 6B, FIG. 16B). Strikingly we found that chloroplast volume per cell was closely correlated to measured ppGpp levels. To exclude potential artefacts due to the protoplast isolation procedure this result was also confirmed in intact cells using a different procedure (Pyke and Leech, 1991) [36] (FIG. 16C). Also in support of these results we found that plants with mutations in the ppGpp biosynthetic enzymes (DM-23, QMai and QMaii) have small but significantly higher chlorophyll content than wild-type or rsh1-1 plants (FIG. 6C).

Figure 17:
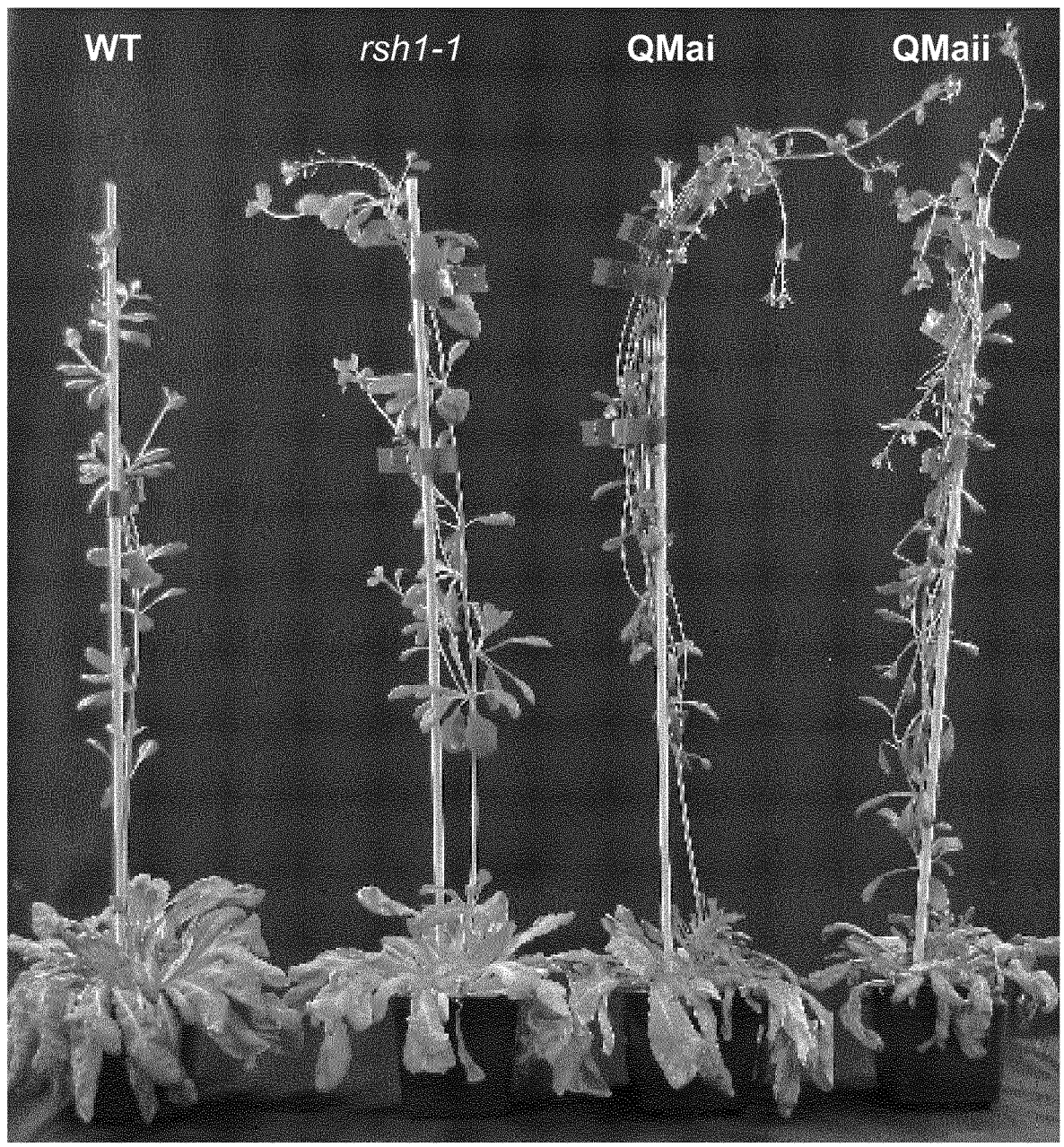
FIG. 17 represents that RSH mutants show visible growth phenotypes under short day conditions. After flowering under short day conditions rsh1-1 plants rapidly become pale and show large numbers of senescent leaves compared to WT plants. In contrast, QMai and QMaii plants have small rosettes and darker leaves. The plants shown are 95 days old.

Further analysis of selected mutants showed that plants lacking multiple RSH ppGpp synthase genes are significantly smaller than wildtype plants when grown in phytagel or in the soil (FIG. 6C and FIG. 16D). Plants expressing the ppGpp hydrolase MESH were also smaller (FIG. 6D). The reduced size was not due to altered developmental timing because leaf emergence and flowering time were not different in the mutants. These differences were even more marked in flowering plants that had been grown under short day conditions for 95 days. In these plants rsh1-1 is visibly paler and DM-23 and QMaii plants darker (FIG. 17).

Together these results strongly suggest that the ppGpp hydrolase RSH1 acts antagonistically with the ppGpp synthase activities of RSH2, RSH3 and CRSH to control ppGpp levels during vegetative growth. The differences in F0 and steady state chloroplast transcript ratios in the different RSH mutants suggest that the small quantities of ppGpp found in growing plants are sufficient to regulate the expression of at least a subset of chloroplast genes and consequently to alter the stoichiometry of nucleus and chloroplast-encoded proteins within the PSII supercomplex and other chloroplast complexes. The presence of functional ppGpp synthases and hydrolases is also important for controlling chloroplast volume per cell as well as vegetative growth.

Example 9: ppGpp Regulates Senescence and Nutrient Remobilisation

Figure 7:
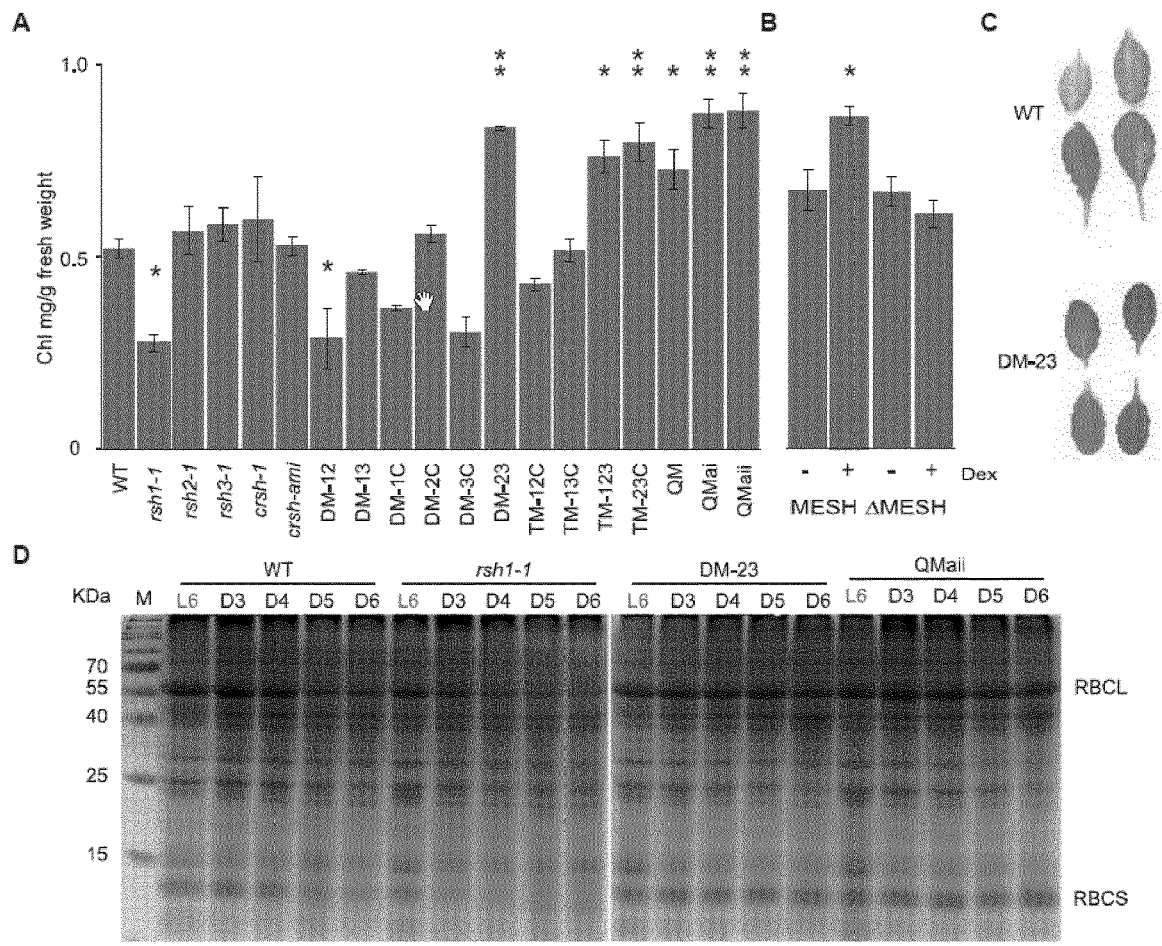
FIG. 7 represents that the antagonistic activity of RSH enzymes is critical for senescence and nutrient remobilisation. Senescence was induced by incubating detached leaves in the darkness and chlorophyll levels were measured after five days in (A) a panel of 18 RSH mutants and (B) induced and non-induced MESH plants, n=3 plants. MESH plants were induced by spraying plants with 10 µM dexamethasone (DEX) or the vehicle (DMSO) 48 hrs before the dark-induced senescence assay. Plants were grown for 48 days under short day conditions, and chlorophyll levels were not significantly different between untreated lines. (C) A photograph of leaves from single plants 5 days after the senescence treatment in (A). (D) Equal quantities of total protein were separated by SDS-PAGE and visualized by Coomassie Brilliant Blue after extraction from the leaves of selected lines after 3 (D3), 4 (D4), 5 (D5) and 6 days (D6) of darkness. Non-treated leaves on the plant were used as a control (L6). Relative pixel densities for RBCL and RBCS are shown below the gel image, for each line pixel density is normalized to the L6 control. Data were analyzed by ANOVA with post hoc Dunnett tests versus the wild-type controls, **P<0.01; error bars, SEM.
Figure 18:
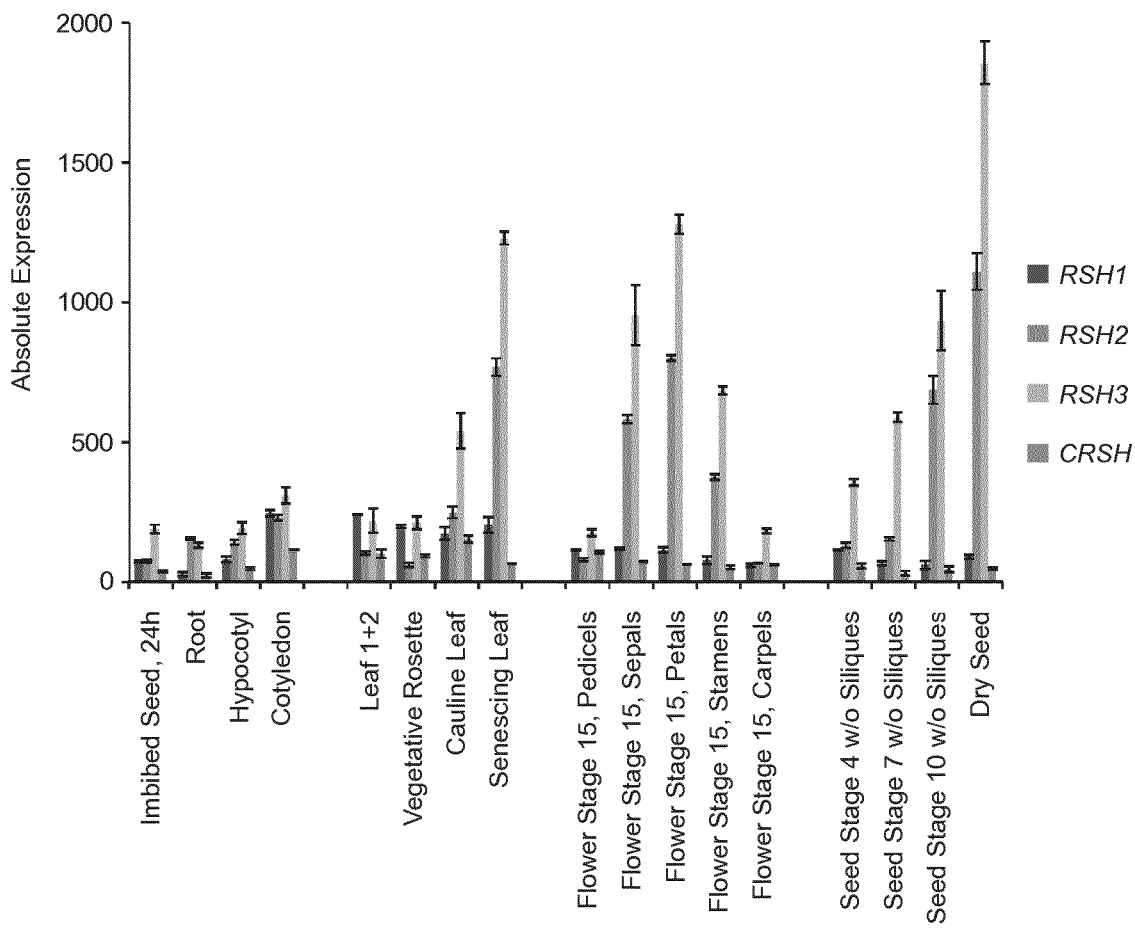
FIG. 18 represents that RSH2 and RSH3 are strongly expressed during senescence and late plant development. Microarray expression profiles of *Arabidopsis* RSH genes in different plant organs and at different stages of development; error bars, SEM; n=3. Data were retrieved from Genevestigator (Zimmermann et al., 2004) [70].
Figure 19:
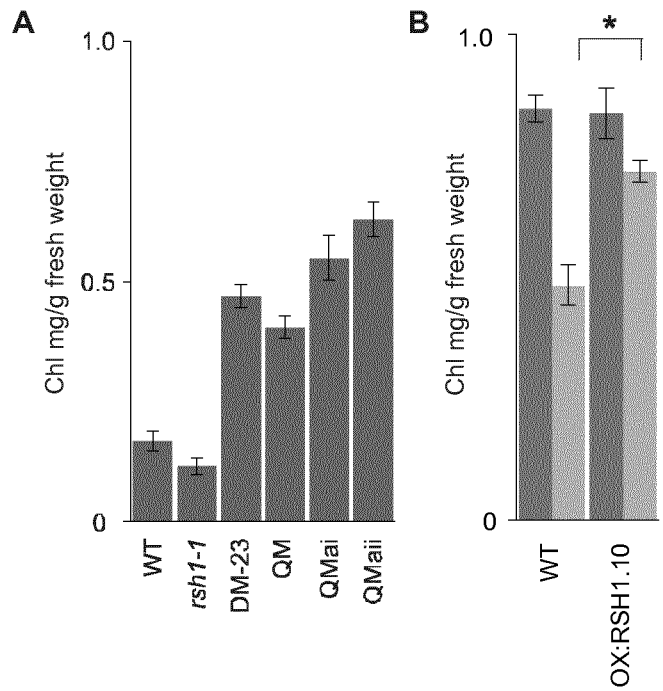
FIG. 19 represents additional dark-induced senescence phenotypes. (A) CRSH may also contribute to the progression of dark-induced senescence. Chlorophyll levels in the leaves of wildtype and selected mutant lines following senescence induction. Prior to senescence induction plants used were grown under long day conditions for 30 days, and had just initiated flowering. This later developmental timepoint results in a faster progression of senescence than in FIG. 7A. Chlorophyll loss was significantly greater in the wildtype than in DM-23, QM, QMai and QMaii (P<0.0001, n=3). In addition the stay green phenotype of QMaii was significantly stronger than that of DM-23 suggesting that CRSH may also contribute during senescence despite its low level of expression, P<0.05, n=3, Data were analyzed by ANOVA. (B) OX:RSH1 plants show a stay-green phenotype. Chlorophyll content in 27 day old WT and OX:RSH1.10 plants under normal growth conditions (dark green) or after senescence induction in the dark for three days (light green), *P=0.01 WT versus OX:RSH1.10 after 3 days in the dark, n=3, two-way Student t-test; error bars, SEM.
Figure 20:
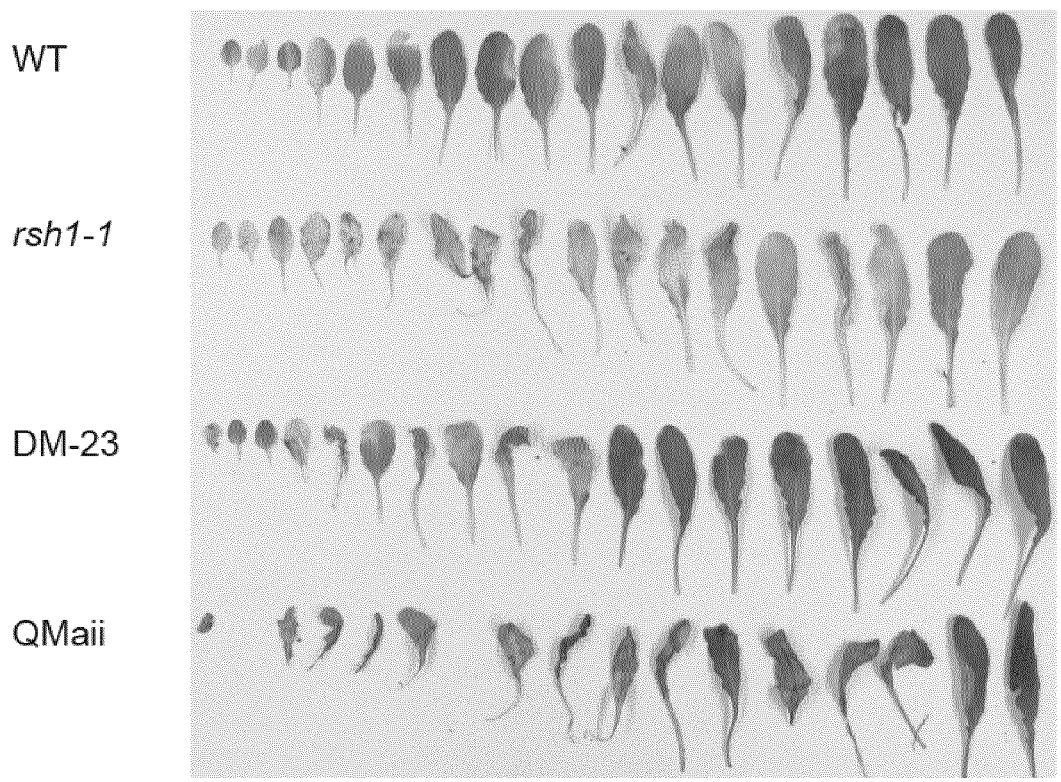
FIG. 20 represents that natural senescence is affected in RSH mutants. Leaves were recovered from the base of the rosette of 95 day old plants grown under short day conditions and arranged in order of age from the oldest on the left. Gaps were left for missing leaves. Natural senescence is visible in the wild type, and appears enhanced in rsh1-1 and reduced in DM-23. QMaii leaves display an unusual death phenotype where they crumple and dry out while remaining green.
Figure 21:
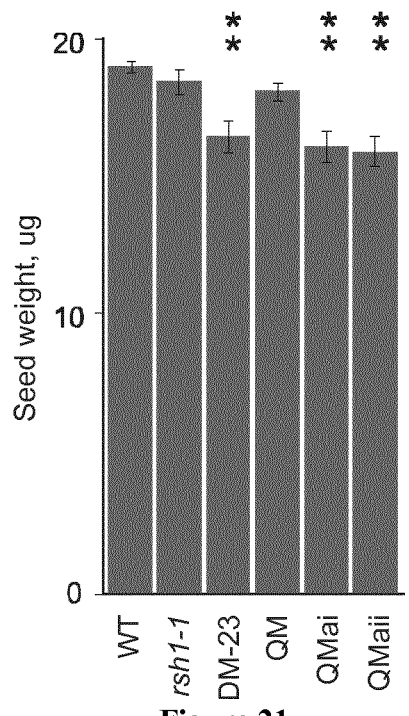
FIG. 21 represents that RSH mutants have altered seed weight suggesting defects in nutrient remobilization or seed development. 300-500 hundred seeds per plant were counted and weighed, 7 or more plants per line were used. Data were analyzed by ANOVA with post hoc Dunnett tests versus the wildtype controls, **P<0.001; error bars, SEM.
Figure 22:
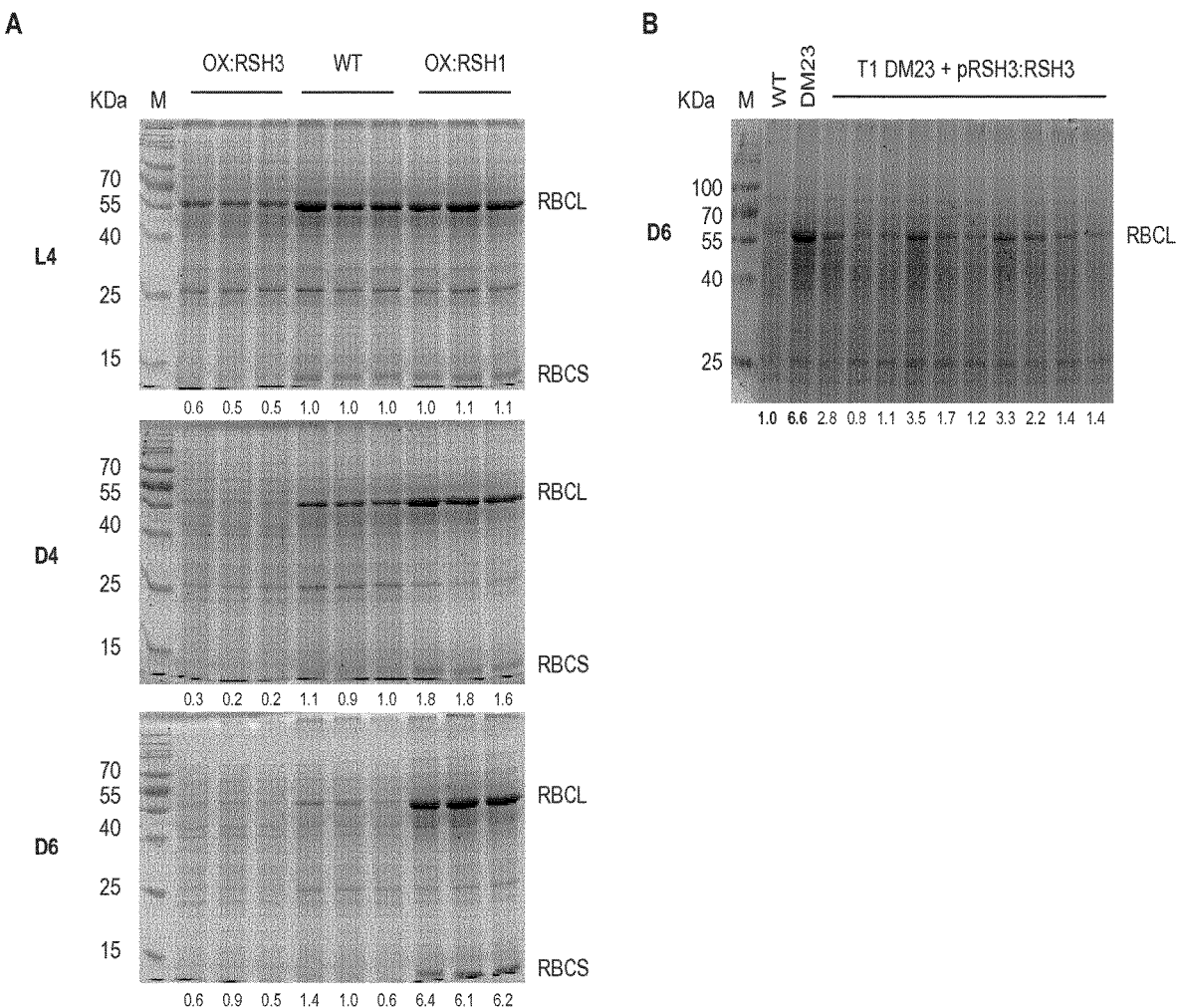
FIG. 22 represents that RuBisCO degradation is regulated by ppGpp during dark-induced senescence. (A) Equal quantities of total protein from WT, OX:RSH3 and OX:RSH1 plants were separated by SDS-PAGE and visualized by Coomassie Brilliant Blue after extraction from the leaves of selected lines after 4 days (D4) and 6 days (D6) of darkness. Plants had grown for 21 DAS at the start of treatment. Non-treated leaves were used as a control on day 4 (L4). Extractions from three different plants are shown for each line. (B) The leaves of WT, DM-23 and independent first generation (T1) DM-23 lines transformed with the genomic RSH3 (pRSH3:RSH3) were analyzed as above after 6 days (D6) of darkness. Below each lane pixel densities for RBCL are shown, normalized to the wild type control on the same gel.
Figure 23:
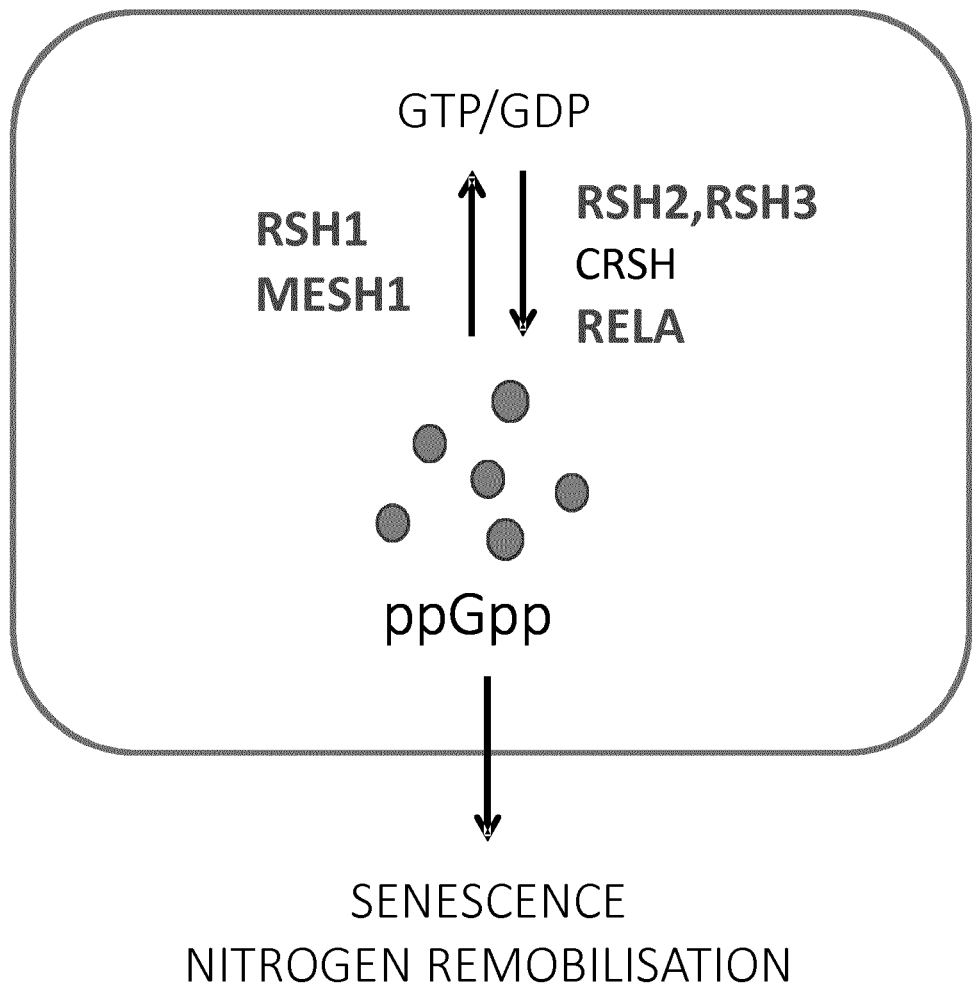
FIG. 23 represents the antagonistic activity of RSH enzymes on ppGpp homeostasis that is critical for senescence and nutrient remobilization.

The expression of RSH2 and RSH3 has been shown to increase in ageing leaves in several studies (Schmid et al., 2005, Mizusawa et al., 2008; Breeze et al., 2011) [56, 17, 57] (FIG. 18). This suggests that there may be specific roles for ppGpp during leaf senescence, when nutrients are recycled and re-directed to the developing seeds (Lim et al., 2007) [58]. We therefore tested the 18 RSH mutants using a widely used dark-induced senescence assay on detached leaves that reproduces many of the phenotypes of developmental senescence and shows a large overlap in gene expression (Buchanan-Wollaston et al., 2005) [59]. We found a striking delayed senescence (or stay-green) phenotype in all the mutants containing insertions in both RSH2 and RSH3 (FIGS. 7A and 7C). CRSH may also contribute to some extent because in QMai and QMaii plants where CRSH is silenced there was a significantly stronger stay-green phenotype than DM-23 when analyzed at later developmental time-points (FIG. 19A). These phenotypes are likely to be due to a reduction in ppGpp biosynthetic capacity by the mutations in the RSH genes. Induction of MESH expression 24 hours before the senescence assay also caused a stay-green phenotype, indicating that removal of ppGpp alone is sufficient (FIG. 7B). In agreement with our identification of RSH1 as a ppGpp hydrolase we also observed an accelerated senescence phenotype in rsh1-1 (FIG. 7A), and a delayed senescence phenotype in OX:RSH1.10 (FIG. 19B). Furthermore, the accelerated senescence phenotype of rsh1-1 is epistatic to mutations in both RSH2 and RSH3. The RSH1 ppGpp hydrolase therefore appears to be required to constrain an increase in ppGpp that may be driven by the transcriptional upregulation of RSH2 and RSH3 expression during senescence. However, ppGpp accumulation alone is not sufficient to trigger senescence because OX:RSH3 plants and induced SYN plants do not show obvious senescence symptoms in vegetative tissues (FIG. 1A), although they do show accelerated senescence during the seed filling stage. The induced senescence phenotypes of the RSH mutants are also relevant during natural plant growth. We saw differences in natural senescence in plants grown under long day conditions that became very strong under short days conditions (FIG. 17). QMaii plants were particularly striking because rather than becoming pale old leaves crumpled and died while still green (FIG. 20). A similar phenotype was also observed in OX:RSH1.10 plants. Senescence is necessary for the remobilization of nutrients and their reallocation to developing fruit or other parts of the plant. We found that the seeds of DM-23 and QM mutant plants were significantly lighter than the seeds of wildtype plants (FIG. 21), suggesting that nutrient reallocation is defective during senescence and/or that ppGpp additionally plays a role during seed development. Supporting the idea that nutrient allocation is defective we also observed a striking retention of the RuBisCO small and large subunits during senescence for mutants deficient in ppGpp biosynthetic enzymes such as DM-23 and QMaii (FIG. 7D). As we observed for chlorophyll, RuBisCO retention in these lines can be directly linked to ppGpp levels because overexpression of RSH3 accelerated and overexpression of RSH1 greatly slowed the degradation of RuBisCO during the dark-induced senescence assay (FIG. 22A). The retention of RuBisCO in DM-23 could also be reversed by complementation with RSH3 indicating that during senescence RSH2 and RSH3 are redundant for RuBisCO degradation as they are for chlorophyll degradation (FIG. 22B). Together these data show that the antagonistic activity of RSH ppGpp synthases and hydrolases is required for chlorophyll degradation and nutrient remobilization during senescence.

REFERENCES Listing

1. REYES-PRIETO, A., WEBER, A. P. & BHATTACHARYA, D. 2007. The origin and establishment of the plastid in algae and plants. Annu. Rev. Genet., 41, 147-68.
2. GREEN, B. R. 2011. Chloroplast genomes of photosynthetic eukaryotes. Plant J., 66, 34-44.
3. JARVIS, P. & LOPEZ-JUEZ, E. 2013. Biogenesis and homeostasis of chloroplasts and other plastids. Nat. Rev. Mol. Cell Biol., 14, 787-802.
4. PUTHIYAVEETIL, S., KAVANAGH, T. A., CAIN, P., SULLIVAN, J. A., NEWELL, C. A., GRAY, J. C., ROBINSON, C., VAN DER GIEZEN, M., ROGERS, M. B. & ALLEN, J. F. 2008. The ancestral symbiont sensor kinase CSK links photosynthesis with gene expression in chloroplasts. Proc. Natl. Acad. Sci. USA, 105, 10061-6.
5. MASUDA, S. 2012. The Stringent Response in Phototrophs. In: NAJAFPOUR, M. (ed.) Advances in Photosynthesis—Fundamental Aspects. InTech.
6. DALEBROUX, Z. D. & SWANSON, M. S. 2012. ppGpp: magic beyond RNA polymerase. Nat. Rev. Microbiol., 10, 203-12.
7. VAN DER BIEZEN, E. A., SUN, J., COLEMAN, M. J., BIBB, M. J. & JONES, J. D. 2000. Arabidopsis RelA/SpoT homologs implicate (p)ppGpp in plant signaling. Proc. Natl. Acad. Sci. USA, 97, 3747-52.
8. ATKINSON, G. C., TENSON, T. & HAURYLIUK, V. 2011. The RelA/SpoT homolog (RSH) superfamily: distribution and functional evolution of ppGpp synthetases and hydrolases across the tree of life. PLoS One, 6, e23479.
9. TOZAWA, Y. & NOMURA, Y. 2011. Signalling by the global regulatory molecule ppGpp in bacteria and chloroplasts of land plants. Plant Biol., 13, 699-709.
10. TAKAHASHI, K., KASAI, K. & OCHI, K. 2004. Identification of the bacterial alarmone guanosine 5'-diphosphate 3'-diphosphate (ppGpp) in plants. Proc. Natl. Acad. Sci. USA, 101, 4320-4.
11. IHARA, Y., OHTA, H. & MASUDA, S. 2015. A highly sensitive quantification method for the accumulation of alarmone ppGpp in Arabidopsis thaliana using UPLC-ESI-qMS/MS. J Plant Res, 128, 511-8.
12. SATO, M., TAKAHASHI, K., OCHIAI, Y., HOSAKA, T., OCHI, K. & NABETA, K. 2009. Bacterial alarmone, guanosine 5'-diphosphate 3'-diphosphate (ppGpp), predominantly binds the beta' subunit of plastid-encoded plastid RNA polymerase in chloroplasts. Chembiochem, 10, 1227-33.
13. NOMURA, Y., TAKABAYASHI, T., KURODA, H., YUKAWA, Y., SATTASUK, K., AKITA, M., NOZAWA, A. & TOZAWA, Y. 2012. ppGpp inhibits peptide elongation cycle of chloroplast translation system in vitro. Plant Mol. Biol., 78, 185-96.
14. NOMURA, Y., IZUMI, A., FUKUNAGA, Y., KUSUMI, K., IBA, K., WATANABE, S., NAKAHIRA, Y., WEBER, A. P., NOZAWA, A. & TOZAWA, Y. 2014. Diversity in Guanosine 3',5'-Bisdiphosphate (ppGpp) Sensitivity Among Guanylate Kinases of Bacteria and Plants. J Biol Chem.
15. KASAI, K., USAMI, S., YAMADA, T., ENDO, Y., OCHI, K. & TOZAWA, Y. 2002. A RelA-SpoT homolog (Cr-RSH) identified in Chlamydomonas reinhardtii generates stringent factor in vivo and localizes to chloroplasts in vitro. Nucleic Acids Res, 30, 4985-92.
16. TOZAWA, Y., NOZAWA, A., KANNO, T., NARISAWA, T., MASUDA, S., KASAI, K. & NANAMIYA, H. 2007. Calcium-activated (p)ppGpp synthetase in chloroplasts of land plants. J Biol Chem, 282, 35536-45.
17. MIZUSAWA, K., MASUDA, S. & OHTA, H. 2008. Expression profiling of four RelA/SpoT-like proteins, homologues of bacterial stringent factors, in Arabidopsis thaliana. Planta, 228, 553-62.
18. MASUDA, S., MIZUSAWA, K., NARISAWA, T., TOZAWA, Y., OHTA, H. & TAKAMIYA, K. 2008. The bacterial stringent response, conserved in chloroplasts, controls plant fertilization. Plant Cell Physiol., 49, 135-41.
19. CHEN, J., BANG, W. Y., LEE, Y., KIM, S., LEE, K. W., KIM, S. W., SON, Y. S., KIM, D. W., AKHTER, S. & BAHK, J. D. 2014. AtObgC-AtRSH1 interaction may play a vital role in stress response signal transduction in Arabidopsis. Plant Physiol. Biochem., 74, 176-84.
20. YAMBURENKO, M. V., ZUBO, Y. O. & BORNER, T. 2015. Abscisic acid affects transcription of chloroplast genes via protein phosphatase 2C-dependent activation of nuclear genes: repression by guanosine-3'-5'-bisdiphosphate and activation by sigma factor 5. Plant J, 82, 1030-41.
21. EARLEY, K. W., HAAG, J. R., PONTES, O., OPPER, K., JUEHNE, T., SONG, K. & PIKAARD, C. S. 2006. Gateway-compatible vectors for plant functional genomics and proteomics. Plant J., 45, 616-29.
22. FIELD, B. & OSBOURN, A. E. 2008. Metabolic diversification—independent assembly of operon-like gene clusters in different plants. Science, 320, 543-7.
23. SCHREIBER, G., METZGER, S., AIZENMAN, E., ROZA, S., CASHEL, M. & GLASER, G. 1991. Overexpression of the relA gene in Escherichia coli. J. Biol. Chem., 266, 3760-7.
24. LEE, K. H., KIM, D. H., LEE, S. W., KIM, Z. H. & HWANG, I. 2002. In vivo import experiments in protoplasts reveal the importance of the overall context but not specific amino acid residues of the transit peptide during import into chloroplasts. Mol. Cells, 14, 388-97.
25. HOGG, T., MECHOLD, U., MALKE, H., CASHEL, M. & HILGENFELD, R. 2004. Conformational antagonism between opposing active sites in a bifunctional RelA/SpoT homolog modulates (p)ppGpp metabolism during the stringent response [corrected]. Cell, 117, 57-68.
26. CRAFT, J., SAMALOVA, M., BAROUX, C., TOWNLEY, H., MARTINEZ, A., JEPSON, I., TSIANTIS, M. & MOORE, I. 2005. New pOp/LhG4 vectors for stringent glucocorticoid-dependent transgene expression in Arabidopsis. Plant J., 41, 899-918.
27. LIU, Y. G. & CHEN, Y. 2007. High-efficiency thermal asymmetric interlaced PCR for amplification of unknown flanking sequences. Biotechniques, 43, 649-50, 652, 654 passim.
28. SUN, D., LEE, G., LEE, J. H., KIM, H. Y., RHEE, H. W., PARK, S. Y., KIM, K. J., KIM, Y., KIM, B. Y., 28. HONG, J. I., PARK, C., CHOY, H. E., KIM, J. H., JEON, Y. H. & CHUNG, J. 2010. A metazoan ortholog of SpoT hydrolyzes ppGpp and functions in starvation responses. *Nat. Struct. Mol. Biol.*, 17, 1188-94.
29. SCHWAB, R., OSSOWSKI, S., RIESTER, M., WARTHMANN, N. & WEIGEL, D. 2006. Highly specific gene silencing by artificial microRNAs in *Arabidopsis. Plant Cell*, 18, 1121-33.
30. GUZMAN, L. M., BELIN, D., CARSON, M. J. & BECKWITH, J. 1995. Tight regulation, modulation, and high-level expression by vectors containing the arabinose PBAD promoter. *J Bacteriol*, 177, 4121-30.
31. ZHAO, S. & FERNALD, R. D. 2005. Comprehensive algorithm for quantitative real-time polymerase chain reaction. *J Comput Biol*, 12, 1047-64
32. ROWAN, B. A. & BENDICH, A. J. 2011. Isolation, quantification, and analysis of chloroplast DNA. *Methods Mol. Biol.*, 774, 151-70.
33. PESARESI, P. 2011. Studying translation in *Arabidopsis* chloroplasts. *Methods Mol Biol*, 774, 209-24.
34. CROCE, R., CANINO, G., ROS, F. & BASSI, R. 2002. Chromophore organization in the higher-plant photosystem II antenna protein CP26. *Biochemistry*, 41, 7334-43.
35. YOO, S. D., CHO, Y. H. & SHEEN, J. 2007. *Arabidopsis* mesophyll protoplasts: a versatile cell system for transient gene expression analysis. *Nat. Protoc.*, 2, 1565-72.
36. PYKE, K. A. & LEECH, R. M. 1991. Rapid Image Analysis Screening Procedure for Identifying Chloroplast Number Mutants in Mesophyll Cells of *Arabidopsis thaliana* (L.) Heynh. *Plant Physiol*, 96, 1193-5.
37. WAHL, A., MY, L., DUMOULIN, R., STURGIS, J. N. & BOUVERET, E. 2011. Antagonistic regulation of dgkA and plsB genes of phospholipid synthesis by multiple stress responses in *Escherichia coli*. *Mol Microbiol*, 80, 1260-75.
38. BATTESTI, A. & BOUVERET, E. 2006. Acyl carrier protein/SpoT interaction, the switch linking SpoT-dependent stress response to fatty acid metabolism. *Mol Microbiol*, 62, 1048-63.
39. MY, L., REKOSKE, B., LEMKE, J. J., VIALA, J. P., GOURSE, R. L. & BOUVERET, E. 2013. Transcription of the *Escherichia coli* fatty acid synthesis operon fabHDG is directly activated by FadR and inhibited by ppGpp. *J Bacteriol*, 195, 3784-95.
40. MAEKAWA, M., HONOKI, R., IHARA, Y., SATO, R., OIKAWA, A., KANNO, Y., OHTA, H., SEO, M., SAITO, K. & MASUDA, S. 2015. Impact of the plastidial stringent response in plant growth and stress responses. *Nature Plants*, 1, 15167.
41. BELGIO, E., JOHNSON, M. P., JURIC, S. & RUBAN, A. V. 2012. Higher plant photosystem II light-harvesting antenna, not the reaction center, determines the excited-state lifetime-both the maximum and the nonphotochemically quenched. *Biophys. J.*, 102, 2761-71.
42. ROBERTSON, E. J., PYKE, K. A. & LEECH, R. M. 1995. arch, an extreme chloroplast division mutant of *Arabidopsis* also alters proplastid proliferation and morphology in shoot and root apices. *J Cell Sci*, 108 (Pt 9), 2937-44.
43. DIRAY-ARCE, J., LIU, B., CUPP, J. D., HUNT, T. & NIELSEN, B. L. 2013. The *Arabidopsis* At1g30680 gene encodes a homologue to the phage T7 gp4 protein that has both DNA primase and DNA helicase activities. *BMC Plant Biol.*, 13, 36.
44. KRIEL A, BITTNER A N, KIM S H, LIU K, TEHRANCHI A K, ZOU W Y, RENDON S, CHEN R, TU B P, WANG J D. Direct regulation of GTP homeostasis by (p)ppGpp: a critical component of viability and stress resistance. Mol Cell. 2012 48:231-241
45. KRASNY, L. & GOURSE, R. L. 2004. An alternative strategy for bacterial ribosome synthesis: *Bacillus subtilis* rRNA transcription regulation. *EMBO J*, 23, 4473-83.
46. BORNER, T., ALEYNIKOVA, A. Y., ZUBO, Y. O. & KUSNETSOV, V. V. 2015. Chloroplast RNA polymerases: Role in chloroplast biogenesis. *Biochim Biophys Acta*, 1847, 761-9.
47. SIDAWAY-LEE, K., COSTA, M. J., RAND, D. A., FINKENSTADT, B. & PENFIELD, S. 2014. Direct measurement of transcription rates reveals multiple mechanisms for configuration of the *Arabidopsis* ambient temperature response. *Genome Biol*, 15, R45.
48. CAHOON, A. B., HARRIS, F. M. & STERN, D. B. 2004. Analysis of developing maize plastids reveals two mRNA stability classes correlating with RNA polymerase type. *EMBO Rep*, 5, 801-6.
49. RAPP, J. C., BAUMGARTNER, B. J. & MULLET, J. 1992. Quantitative analysis of transcription and RNA levels of 15 barley chloroplast genes. Transcription rates and mRNA levels vary over 300-fold; predicted mRNA stabilities vary 30-fold. *J Biol Chem*, 267, 21404-11.
50. GERHARDT, R., STITT, M. & HELDT, H. W. 1987. Subcellular Metabolite Levels in Spinach Leaves: Regulation of Sucrose Synthesis during Diurnal Alterations in Photosynthetic Partitioning. *Plant Physiol*, 83, 399-407.
51. SUZUKI, J. Y., SRIRAMAN, P., SVAB, Z. & MALIGA, P. 2003. Unique architecture of the plastid ribosomal RNA operon promoter recognized by the multisubunit RNA polymerase in tobacco and other higher plants. *Plant Cell*, 15, 195-205.
52. SWIATECKA-HAGENBRUCH, M., LIERE, K. & BORNER, T. 2007. High diversity of plastidial promoters in *Arabidopsis thaliana*. *Mol Genet Genomics*, 277, 725-34.
53. SCHMIDT, E. K., CLAVARINO, G., CEPPI, M. & PIERRE, P. 2009. SUnSET, a nonradioactive method to monitor protein synthesis. *Nat. Methods*, 6, 275-7.
54. ENGELMANN, E. C., ZUCCHELLI, G., GARLASCHI, F. M., CASAZZA, A. P. & JENNINGS, R. C. 2005. The effect of outer antenna complexes on the photochemical trapping rate in barley thylakoid Photosystem II. *Biochim Biophys Acta*, 1706, 276-86.
55. ITO, D., KATO, T., MARUTA, T., TAMOI, M., YOSHIMURA, K. & SHIGEOKA, S. 2012. Enzymatic and molecular characterization of *Arabidopsis* ppGpp pyrophosphohydrolase, AtNUDX26. *Biosci Biotechnol Biochem*, 76, 2236-41.
56. SCHMID, M., DAVISON, T. S., HENZ, S. R., PAPE, U. J., DEMAR, M., VINGRON, M., SCHOLKOPF, B., WEIGEL, D. & LOHMANN, J. U. 2005. A gene expression map of *Arabidopsis thaliana* development. *Nat Genet*, 37, 501-6.
57. BREEZE, E., HARRISON, E., MCHATTIE, S., HUGHES, L., HICKMAN, R., HILL, C., KIDDLE, S., KIM, Y. S., PENFOLD, C. A., JENKINS, D., ZHANG, C., MORRIS, K., JENNER, C., JACKSON, S., THOMAS, B., TABRETT, A., LEGAIE, R., MOORE, J. D., WILD, D. L., OTT, S., RAND, D., BEYNON, J., DENBY, K., MEAD, A. & BUCHANAN-WOLLASTON, V. 2011. High-resolution temporal profiling of transcripts during *Arabidopsis* leaf senescence reveals a distinct chronology of processes and regulation. *Plant Cell*, 23, 873-94.
58. LIM, P. O., KIM, H. J. & NAM, H. G. 2007. Leaf senescence. *Annu Rev Plant Biol*, 58, 115-36.

59. BUCHANAN-WOLLASTON, V., PAGE, T., HARRISON, E., BREEZE, E., LIM, P. O., NAM, H. G., LIN, J. F., WU, S. H., SWIDZINSKI, J., ISHIZAKI, K. & LEAVER, C. J. 2005. Comparative transcriptome analysis reveals significant differences in gene expression and signalling pathways between developmental and dark/starvation-induced senescence in *Arabidopsis*. *Plant J*, 42, 567-85.
60. LIERE, K., WEIHE, A. & BORNER, T. 2011. The transcription machineries of plant mitochondria and chloroplasts: Composition, function, and regulation. *J. Plant Physiol.*, 168, 1345-60.
61. ROCHAIX, J. D. 2013. Redox regulation of thylakoid protein kinases and photosynthetic gene expression. *Antioxid. Redox Signal.*, 18, 2184-201.
62. PFANNSCHMIDT, T. & MUNNÉ-BOSCH, S. 2013. Plastid Signaling During the Plant Life Cycle. In: BISWAL, B., KRUPINSKA, K. & BISWAL, U. C. (eds.) *Plastid Development in Leaves during Growth and Senescence*. Springer Netherlands.
63. TILLER, N. & BOCK, R. 2014. The Translational Apparatus of Plastids and Its Role in Plant Development. *Mol. Plant*.
64. KINDGREN, P., KREMNEV, D., BLANCO, N. E., DE DIOS BARAJAS LOPEZ, J., FERNANDEZ, A. P., TELLGREN-ROTH, C., KLEINE, T., SMALL, I. & STRAND, A. 2012. The plastid redox insensitive 2 mutant of *Arabidopsis* is impaired in PEP activity and high light-dependent plastid redox signalling to the nucleus. *Plant J.*, 70, 279-91.
65. FELLER, U., ANDERS, I. & MAE, T. 2008. Rubiscolytics: fate of Rubisco after its enzymatic function in a cell is terminated. *J Exp Bot*, 59, 1615-24.
66. ISHIDA, H., IZUMI, M., WADA, S. & MAKINO, A. 2014. Roles of autophagy in chloroplast recycling. *Biochim Biophys Acta*, 1837, 512-21.
67. POTRYKUS, K. & CASHEL, M. 2008. (p)ppGpp: still magical? *Annu. Rev. Microbiol.*, 62, 35-51.
68. BANG, W. Y., CHEN, J., JEONG, I. S., KIM, S. W., KIM, C. W., JUNG, H. S., LEE, K. H., KWEON, H. S., YOKO, I., SHIINA, T. & BAHK, J. D. 2012. Functional characterization of ObgC in ribosome biogenesis during chloroplast development. *Plant J.*, 71, 122-34.
69. DAVID, A., DOLAN, B. P., HICKMAN, H. D., KNOWLTON, J. J., CLAVARINO, G., PIERRE, P., BENNINK, J. R. & YEWDELL, J. W. 2012. Nuclear translation visualized by ribosome-bound nascent chain puromycylation. *J Cell Biol*, 197, 45-57.
70. ZIMMERMANN, P., HIRSCH-HOFFMANN, M., HENNIG, L. & GRUISSEM, W. 2004. GENEVESTIGATOR. *Arabidopsis* microarray database and analysis toolbox. *Plant Physiol.*, 136, 2621-32.

The invention claimed is:

1. A method for accelerating nitrogen remobilization and/or senescence in a photosynthetic eukaryotic plant or alga, said method comprising:
  (i) transforming a photosynthetic eukaryotic plant or alga with a DNA construct comprising a nucleic acid sequence encoding an antisense of a nucleic acid molecule encoding an RSH1 hydrolase from a plant or alga; and
  (ii) selecting the transformed plant or alga exhibiting an increased amount of ppGpp accumulation as compared to an unmodified plant or alga, and
    (a) accelerated nitrogen remobilization as compared to an unmodified plant or alga, and/or
    (b) accelerated senescence as compared to an unmodified plant or alga.

2. A method for producing a genetically modified photosynthetic eukaryotic plant or alga, the method comprising:
  (i) transforming a plant or alga with a DNA construct comprising a nucleic acid sequence encoding an antisense of a nucleic acid molecule encoding an RSH1 hydrolase from a plant or alga; or
  (ii) mutating the native RSH1 gene of the plant or alga thus inactivating the guanosine tetraphosphate (ppGpp) hydrolase domain of the native RSH1 gene; and
  (iii) selecting the transformed or mutated plant or alga exhibiting increased amounts of ppGpp accumulation, as compared to an unmodified plant or alga, and wherein the selected transformed or mutated plant or alga exhibits accelerated nitrogen remobilization and/or accelerated senescence, as compared to an unmodified plant or alga.

* * * * *